(12) United States Patent
McGlade et al.

(10) Patent No.: US 7,507,801 B2
(45) Date of Patent: Mar. 24, 2009

(54) ADAPTER GENE

(75) Inventors: Jane McGlade, Toronto (CA); Michael Loreto, Toronto (CA)

(73) Assignee: The Hospital for Sick Children, Toronto (CA)

( * ) Notice: Subject to any disclaimer, the term of this patent is extended or adjusted under 35 U.S.C. 154(b) by 615 days.

(21) Appl. No.: 10/432,746

(22) PCT Filed: Nov. 26, 2001

(86) PCT No.: PCT/CA01/01662

§ 371 (c)(1),
(2), (4) Date: Nov. 3, 2003

(87) PCT Pub. No.: WO02/42452

PCT Pub. Date: Mar. 30, 2002

(65) Prior Publication Data

US 2004/0171537 A1    Sep. 2, 2004

(30) Foreign Application Priority Data

Nov. 27, 2000  (CA) .................................. 2324663

(51) Int. Cl.
C07H 21/02    (2006.01)
(52) U.S. Cl. .................................... 536/23.1
(58) Field of Classification Search ................ 536/23.1
See application file for complete search history.

(56) References Cited

FOREIGN PATENT DOCUMENTS

WO    WO 00/58473    * 10/2000

OTHER PUBLICATIONS

Tockman et al (Cancer Res., 1992, 52:2711s-2718s).*
Gura (Science, 1997, 278:1041-1042.).*
The 1997/1998 Stratagene catalog (p. 118, 1997/1998).*
1997/1998 Stratagene Catalog (p. 118).*
Holland et al., "Functional Cloning of Src-like Adapter Protein-2 (SLAP-2), a Novel Inhibitor of Antigen Receptor Signalling", (2001) J Exp. Med., Tokyo, V. 184, pp. 1263-1276.
Swissprot Database, Kawabata et al., "Hypothetical protein FLJ21992 (Src-like adapter protein 2) (Modulator of antigen receptor signaling MARS).", (2001) accession No. Q9H6Q3, XP002209802, abstract.
EMBL Database , Holland et al., "*Homo sapiens* Src-like adapter protein-2 mRNA, complete cds." (2001), accession No. AF326353, XP002209803, abstract.
EMBL Database, Sugano et al., "*Homo sapiens* cDNA: FLJ21992 fis, clone HEP06554", (2000), accession No. AK025645, XP002209804, abstract.
EMBL Database, Marra et al., "mj43c04.yl Soares, mouse embryo NbME13.5 14.5 Mus musculus cDNA clone Image:478854 5' similar to TR:Q13239 Q13239 Putative SRC-Like Adapter Protein;, mRNA sequence", (1999), accession No. AI510095, XP002209805, abstract.

Tang et al., "SLAP, a dimeric adapter protein, plays a functional role in T cell receptor signaling", (1999), P.N.A.S. USA, V.96, pp. 9775-9780.
Loreto et al., "Functional cooperation between c-Cb1 and Src-like adaptor protein 2 in the negative regulation of T-cell receptor signaling.", (2002), Mol. and Cell. Biol., V.22, pp. 4241-4255, XP001098735.
Cantrell, D. (1996) T cell antigen receptor signal transduction pathways, Annu. Rev. Immunol. 14, 259-274.
Latour, S. & Veillette, A. (2001) Proximal protein tyrosine kinases in immunoreceptor signaling, Curr Opin Immunol. 13, 299-306.
Van Leeuwen, J. E. & Samelson, L. E. (1999) T cell antigen-receptor signal transduction, Curr Opin Immunol. 11, 242-8.
Clements, J. L., Boerth, N.J., Lee, J. R. & Koretzky, G.A. (1999) Integration of T cell receptor-dependent signaling pathways by adapter proteins, Annu Rev Immunol. 17, 89-108.
Rudd, C.E. (1999) Adaptors and molecular scaffolds in immune cell signaling, Cell. 96, 5-8.
Zhang, W., Sloan-Lancaster, J., Kitchen, J., Trible, R. P. & Samelson, L. E. (1998) LAT: the ZAP-70 tyrosine kinase substrate that links T cell receptor to cellular activation, Cell. 92, 83-92.
Liu, S.K., Fang, N., Koretzky, G.A. & McGlade, C. J. (1999) The hematopoietic-specific adaptor protein gads functions in T-cell signaling via interactions with the SLP-76 and LAT adaptors, Curr. Biol. 9, 67-75.
Weiss, A. & Littman, D. R. (1994) Signal transduction by lymphocyte antigen receptors, Cell. 76, 263-274.
Rudd, C. E. & Schneider, H. (2000) Lymphocyte signaling: Cb1 sets the threshold for autoimmunity, Curr Biol. 10, R344-7.
Leo, A. & Schraven, B. (2001) Adapters in lymphocyte signaling, Curr Opin Immunol. 13, 307-16.
Brdicka, T., Pavlistova, D., Leo, A., Bruyns, E., Korinek, V., Angelisova, P., Scherer, J., Shevchenko, A., Hilgert, I., Cerny, J., Drbal, K., Kuramitsu, Y., Kornacker, B., Horejsi, V. & Schraven, B. (2000) Phosphoprotein associated with glycosphingolipid-enriched microdomains (PAG), a novel ubiquitously expressed transmembrane adaptor protein, binds the protein tyrosine kinase csk and is involved in regulation of T cell activation, J Exp Med. 191, 1591-604.
Pfrepper, K. I., Marie-Cardine, A., Simeoni, L., Kuramitsu, Y., Leo, A., Spicka, J., Hilgert, I., Scherer, J & Schraven, B. (2001) Structural and functional dissection of the cytoplasmic domain of the transmembrane adaptor protein SIT (SHP2-interacting transmembrane adaptor protein), Eur JImmunol. 31, 1825-36.

(Continued)

*Primary Examiner*—Sean E Aeder
(74) *Attorney, Agent, or Firm*—Myers Bigel Sibley & Sajovec, P.A.

(57)    ABSTRACT

The present invention relates to the identification and cloning of a novel gene, MARS (Modulator of Antigen Receptor Signaling), which is a putative tumor suppressor gene. The present invention also relates to the relation of the MARS gene to human cancers and its use in the diagnosis and prognosis of human cancer. The invention also relates to the therapy of human cancers which have a mutation in the MARS gene, or lack the MARS gene, including gene therapy, protein replacement therapy and protein mimetics. Finally, the invention relates to the screening of drugs for cancer therapy.

8 Claims, 16 Drawing Sheets

OTHER PUBLICATIONS

Chow, L. M., Fournel, M., Davidson, D. & Veillette, A. (1993) Negative regulation of T-cell receptor signaling by tyrosine protein kinase p50csk, Nature. 365, 156-60.

Okada, M., Nada, S., Yamanashi, Y., Yamamoto, T. & Nakagawa, H. (1991) CSK: a protein-tyrosine kinase involved in regulation of src family kinases, J Biol Chem . 266, 24249-52.

Lemay, S., Davidson, D., Latour, S. & Veillette, A. (2000) Dok-3, a novel adapter molecule involved in the negative regulation of immunoreceptor signaling, Mol Cell Biol. 20, 2743-54.

Thien, C. B. & Langdon, W. Y. (2001) Cbl: many adaptations to regulate protein tyrosine kinases, Nat Rev Mol Cell Biol. 2, 294-307.

Lupher, M. L., Jr., Rao, N., Eck., M. J. & Band, H. (1999) The Cbl protooncoprotein: a negative regulator of immune receptor signal transduction, Immunol Today. 20, 375-82.

Zheng, N., Wang, P., Jeffrey, P. D. & Pavietich, N. P. (2000) structure of a c-Cbl-UbcH7 complex: RING domain function in ubiquitin-protein ligases, Cell. 102, 53 3-9.

Joazeiro, C. A., Wing, S. S., Huang, H., Leverson, J. D., Hunter, T. & Liu, Y. C. (1999) The tyrosine kinase negative regulator c-Cbl as a RING-type, E2-dependent ubiquitin-protein ligase, Science, 286, 309-312.

Donovan JA, Wange RL, Langdon WY & Samelson LE. (1994) The protein product of the c-cbl protooncogene is the I 20-kDa tyrosine-phosphorylated protein in Jurkat cells activated via the T cell antigen receptor, J Biol. Chem. 269, 2292 1-22924.

Fournel, M., Davidson, D., Weil, R. & Veillette, A. (1996) Association of tyrosine protein kinase Zap-70 with the protooncogene product p12Oc-cb1 in T lymphocytes., I Exp. Med. 183, 301-306.

Meng, W., Sawasdikosol, S., Burakoff, S. J. & Eck, M. J. (1999) Structure of the amino-terminal domain of Cbl complexed to its binding site on ZAP-70 kinase, Nature. 398, 84-90.

Lupher, M. L., Jr., Songyang, Z., Shoelson, S. E., Cantley, L. C. & Band , H. (1997) The Cbl phosphotyrosine-binding domain selects a D(N/D)XpY motif and binds to the Tyr292 negative regulatory phosphorylation site of ZAP-70, JBiol Chem. 272, 33140-4.

Lupher, M. L., Jr., Rao, N., Lill, N. L. Andoniou, C. E., Miyake, S., Clark, E. A., Druker, B. & Band, H. (1998) Cbl-mediated negative regulation of the Syk tyrosine kinase. A critical role for Cbl phosphotyrosine-binding domain binding to Syk phosphotyrosine 323, JBiol Chem. 273, 35273-81.

Murphy, M. A., Schnall, R. G., Venter, D. J., Barnett, L., Bertoncello, I., Thien, C. B., Langdon, W. Y. & Bowtell, D. D. (1998) Tissue hyperplasia and enhanced T-cell signaling via ZAP-70 in c-Cbl-deficient mice, Mol. Cell. Biol. 18, 4872-4882.

Rao, N., Lupher, M. L., Jr., Ota, S., Reedquist, K. A., Druker, B. J. & Band, H. (2000) The linker phosphorylation site Tyr292 mediates the negative regulatory effect of Cbl on ZAP-70 in T cells, JImmunol. 164, 4616-4626.

Ota, S., Hazeki, K., Rao, N., Lupher, M. L., Jr., Andoniou, C. E., Druker, B. & Band, H. (2000) The RING finger domain of Cbl is essential for negative regulation of Syk tyrosine kinase, JBiol Chem. 275, 414-22.

Van Leeuwen, J. B., Paik, P. K. & Samelson, L. E. (1999) The oncogenic 70Z Cbl mutation blocks the phosphotyrosine binding domain-dependent negative regulation of ZAP-70 by c-Cbl in Jurkat T cells, Mol Cell Biol. 19, 6652-64.

Wang, H. Y., Altman, Y., Fang, D., Elly, C., Dai, Y., Shao, & Liu, Y. C. (2001) Cbl Promotes Ubiquitination of the T Cell Receptor {zeta} through an Adaptor Function of Zap-70, J Biol Chem. 15, 15.

Thien, C. B., Bowtell, D. D. & Langdon, W. Y. (1999) Perturbed regulation of Zap-70 and sustained tyrosine phosphorylation of LAT and SLP-76 in c-Cbl-deficient thymocytes, J Immunol. 162, 7133-9.

Levkowitz, G., Waterman, H., Zamir, E., Kam, Z., Oved, S., Langdon, W. Y.; Beguinot, L., Geiger, B. & Yarden, Y. (1998) c-Cbl/Sli-1 regulates endocytic sorting and ubiquitination of the epidermal growth factor receptor, Genes Dev. 12, 3663-3674.

Lee, P. S., Wang, Y., Dominguez, M. G., Yeung, Y. G., Murphy, M.A., Bowtell, D. D. & Stanley, E. R. (1999) The Cbl protooncoprotion stimulates CSF-1 receptor multiubiquitination and endocytosis, and attenuates macrophage proliferation, Ambo 1 18, 3616-3628.

Miyake, S., Milan-Robinson, K. P., Lei, N. L., Dullard, P. & Band, H. (1999) Cbl-mediated negative regulation of Platelet-derived growth factor receptor-dependent cell proliferation. A critical role for Cbl tyrosine kinase-binding domain, J Biol Chem. 274, 16619-28.

Sosinowski, T., Pandey, A., Dixit, V. M. & Weiss, A. (2000) Src-like adaptor protein (SLAP) is a negative regulator of T cell receptor signaling, JExp Med. 191, 463-474.

Roche S, Alonso G, Kazlauskas A, Dixit Vm, Courtneidge Sa & Pandey A. (1998) Src-like adaptor protein (Slap) is a negative regulator of mitogenesis, Curr Biol. 8, 975-8.

Pandey A, Duan H & Dixit Vm. (1995) Characterization of a novel Src-like adapter protein that associates with the Eck receptor tyrosine kinase, JBiol Chem. 270, 19201-4.

Sosinowski, T., Killeen, N. & Weiss, A. (2001) The Src-like adaptor protein downregulates the T cell receptor on CD4+CD8+ thymocytes and regulates positive selection, Immunity. 15, 457-66.

Manes G, Bello P & Roche 5. (2000) Slap negatively regulates Src Mitogenic function but does not revert Src-induced cell morphology changes, Mol Cell Biol. 20, 3396-406.

Kratchmarova, I., Sosinowski, T., Weiss, A., Witter, K., Vincenz, C. and Pandy, A. (2001). Characterization of promoter region and genomic structure of the murine and human genes encoding Src like adapter protein. Gene, 262, 267-273.

Mhawech et al. "Myelodysplastic syndrome: review of the cytogenic and molecular data" *Critical Reviews in Oncology/Hematology* 40:229-238 (2001).

Liu et al. "Risk Factor Analysis in Myelodysplastic Syndrome Patients with del(20p): prognosis revisited" *Cancer Genetics and Cytogenetics* 171:9-16 (2006).

* cited by examiner

```
  1 ggcccaatctggtttctctgagaagcaaaggactgctgtactagtttcgtggagattgtctg 63 ctgacaaagaagcttgatcacagtacctcagcctactctgactcctttctggtgaccgat 123 cctccaggctgctggggcctgagatgccgactaccttaggacctgcaaaggcctgacctg 183 tcgggtcagtgtgcacattggctgactaccctcatcaaacgtctgatggcaaacctttcc 243 ctttccaggttcagtgtgcttgtgagcgtctgctgagtgatgggaagtttgtccagcaga
                                            M   G   S   L   S   R
303 gggaaaacctccagccccagcccagctcctctggtccagaccaggaacccgtgtccatg
     G   K   T   S   S   P   S   P   S   S   S   G   P   D   Q   E   P   V   S   M
363 caaccagaaagacacaaggtcacagctgtggccctgggcagtttcccagcaggtgaacag
     Q   P   E   R   H   K   V   T   A   V   A   L   G   S   F   P   A   G   E   Q
423 gccagactatctctgagactcggggagccgctgaccatcatctctgaggatggagattgg
     A   R   L   S   L   R   L   G   E   P   L   T   I   I   S   E   D   G   D   W
483 tggacagtccagtcggaagtctcaggcagagagtaccacatgcccagtgtgtatgtggct
     W   T   V   Q   S   E   V   S   G   R   E   Y   H   M   P   S   V   Y   V   A
543 aaagtcgcccacgggtggctgtacgagggcctgagccgggagaaagccgaggaactactc
     K   V   A   H   G   W   L   Y   E   G   L   S   R   E   K   A   E   E   L   L
603 ctgttacctgggaaccccggaggggccttcctcatccgggagagccagaccaggagaggc
     L   L   P   G   N   P   G   G   A   F   L   I   R   E   S   Q   T   R   R   G
663 tgctattccctgtccgtccgactcagccgccctgcatcttgggaccggatcagacactac
     C   Y   S   L   S   V   R   L   S   R   P   A   S   W   D   R   I   R   H   Y
723 aggatacagcgtcttgacaatggctggctgtacatctcacctcgcctcaccttcccctca
     R   I   Q   R   L   D   N   G   W   L   Y   I   S   P   R   L   T   F   P   S
783 ctccacgccttggtggagcattactctgagctagcagatggcatctgctgtcccctcagg
     L   H   A   L   V   E   H   Y   S   E   L   A   D   G   I   C   C   P   L   R
843 gagccgtgtgtcctgcagaagcttgggccactacctggcaaagatacacctccacctgtg
     E   P   C   V   L   Q   K   L   G   P   L   P   G   K   D   T   P   P   P   V
903 actgtgccaacatcatcactaaattggaaaaagctggaccgcagcctcctgtttctggaa
     T   V   P   T   S   S   L   N   W   K   K   L   D   R   S   L   L   F   E
963 gcacctgcgagtggggaggcatctctgctcagtgagggctccgagagtccctcagttcc
     A   P   A   S   G   E   A   S   L   L   S   E   G   L   R   E   S   L   S   S
1023 tacatcagcctggctgaggaccccttggatgatgcttagccctggaacacaaagagaaag
     Y   I   S   L   A   E   D   P   L   D   D   A
1083 ggaaccaagactgtggcaccgagagctccaactccgctgaccctgacaaagctccaggag 1143 gcaaggctgggagaacagagacggctggggtggggcacagacactcggggcctcacctgg 1203 gctttctgataagtcatgtatctcctaaggcctcaccctacctactacttctagtccat 1263 gtgcagtgcagttcaaagcagggctggcctctacagagaataaaatacttctgaggtcca 1323 aaaaaaaaaaaaaaaaaaaaaaaaa
```

Full length mouse cDNA

FIGURE 1A (b)

```
mMARS:   1 MGSLSSRGKTSSPSPSSSGPDQEPVSMQPERHKVTAVALGSFPAGEQARLSRLGEPLTIISEDGDWTVQSEVS  75
           S+S P + P+S              L +P+ + +   R GE L +IS++G WW   S +
mSLAP:   1 ---------MGNSMKSTSPPSERPLSSSEGLESDFLAVLTDYPSEDISPPIFRRGEKLRVISDEGGWWKAISLST 66 mMARS:  76 GREYHMPSVYVAKVAHGWLYEGLSREKAEELLLLPGNPGGAFLIRESQIRRGCYSLSVRLSRPASWDRIRHYRIQ 150
           GRE ++P + VA+V HGWL+EGL R+KAEELL LP   G+F+IRES+T++G YSLSVR       +++HYRI
mSLAP:  67 GRESYIPGICVARVYHGWLFEGLGRDKAEELLQLPDIKIGSFMIRESETKKGFYSLSVR------HRQVKHYRIF 135 mMARS: 151 RLINGWLYISPRLTFPSLHALVEHYSELADGICCPLREPCVLQKL-----GPLFGKDTPPPVTVPTSSLNWKKLD 220
           RL N W YISPRLTF L LV HYSE+ADG+CC L PC+ Q +     P P      PVT+ + +WK++
mSLAP: 136 RLPNNWYYISPRLTFQCLEDLVIHYSEVADGLCCVLTTPCLAQNIPAPTSHPSPCTSPGSPVTLRQKTFDWKRVS 210 mMARS: 221 R----SLLFLEAPASGEASLLSEGLRESLSSYISLAEDPLDDA--------------------------------- 259
           R      E P  + SL S GLRES++SY+SL  D    +
mSLAP: 211 RLQEGSEGAENPLRVDESLFSYGLRESIASYLSLTGDD-SSSFDRKKKSLSLMYTGSKRKSSFFSAPQYFED--- 281
```

FIGURE 1B (c)

mMARS

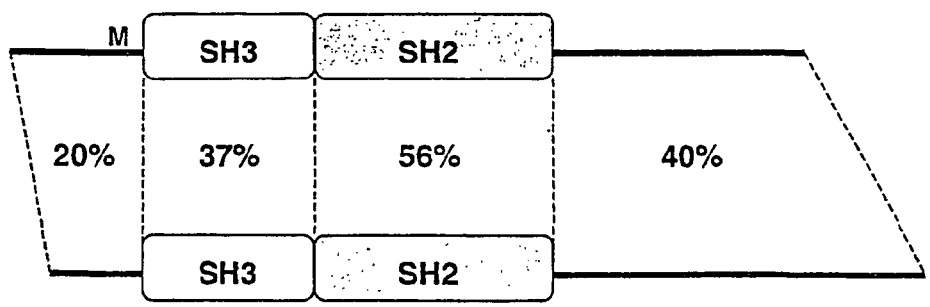

mSLAP figure

FIGURE 1C

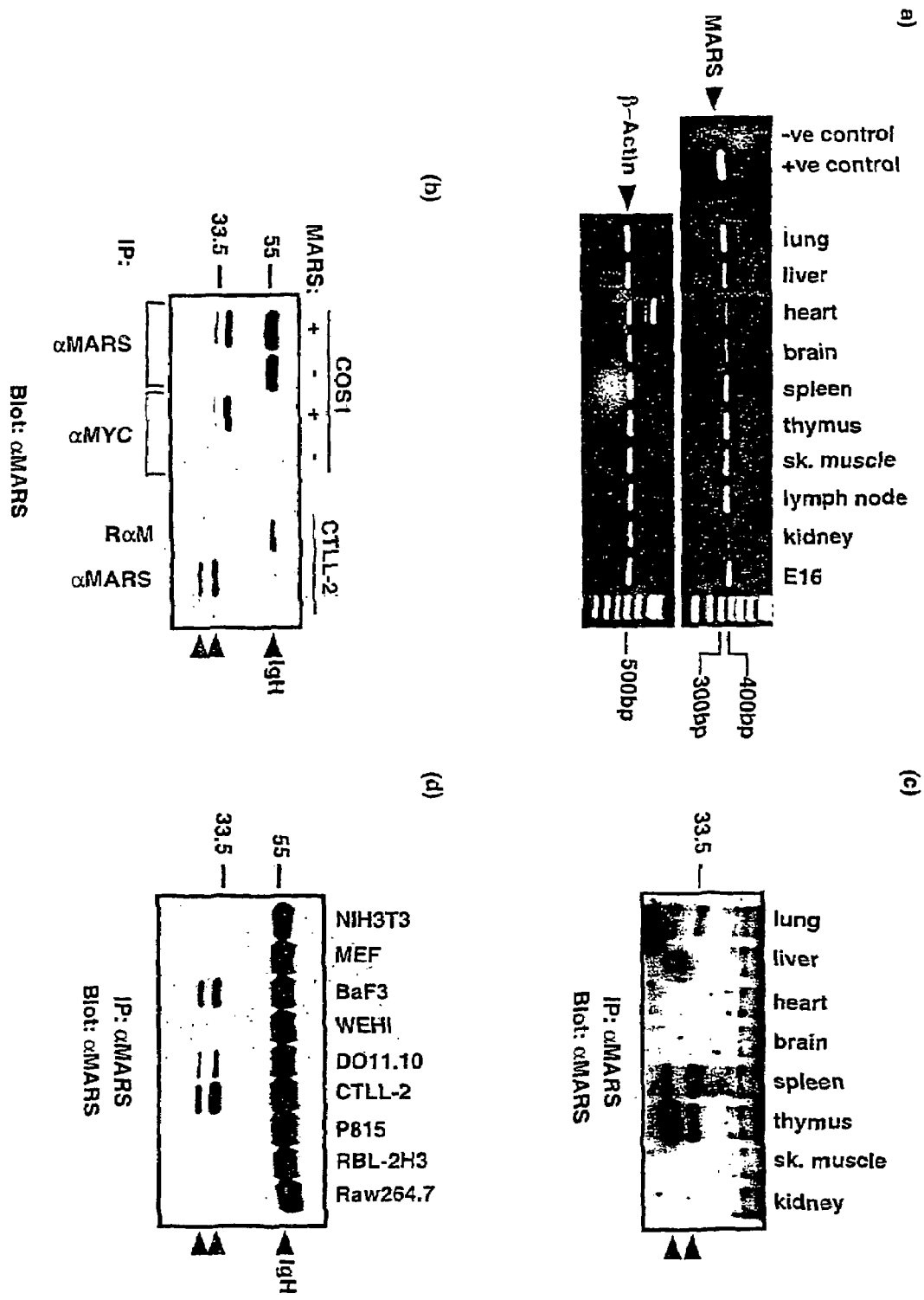
FIGURES 2A-D

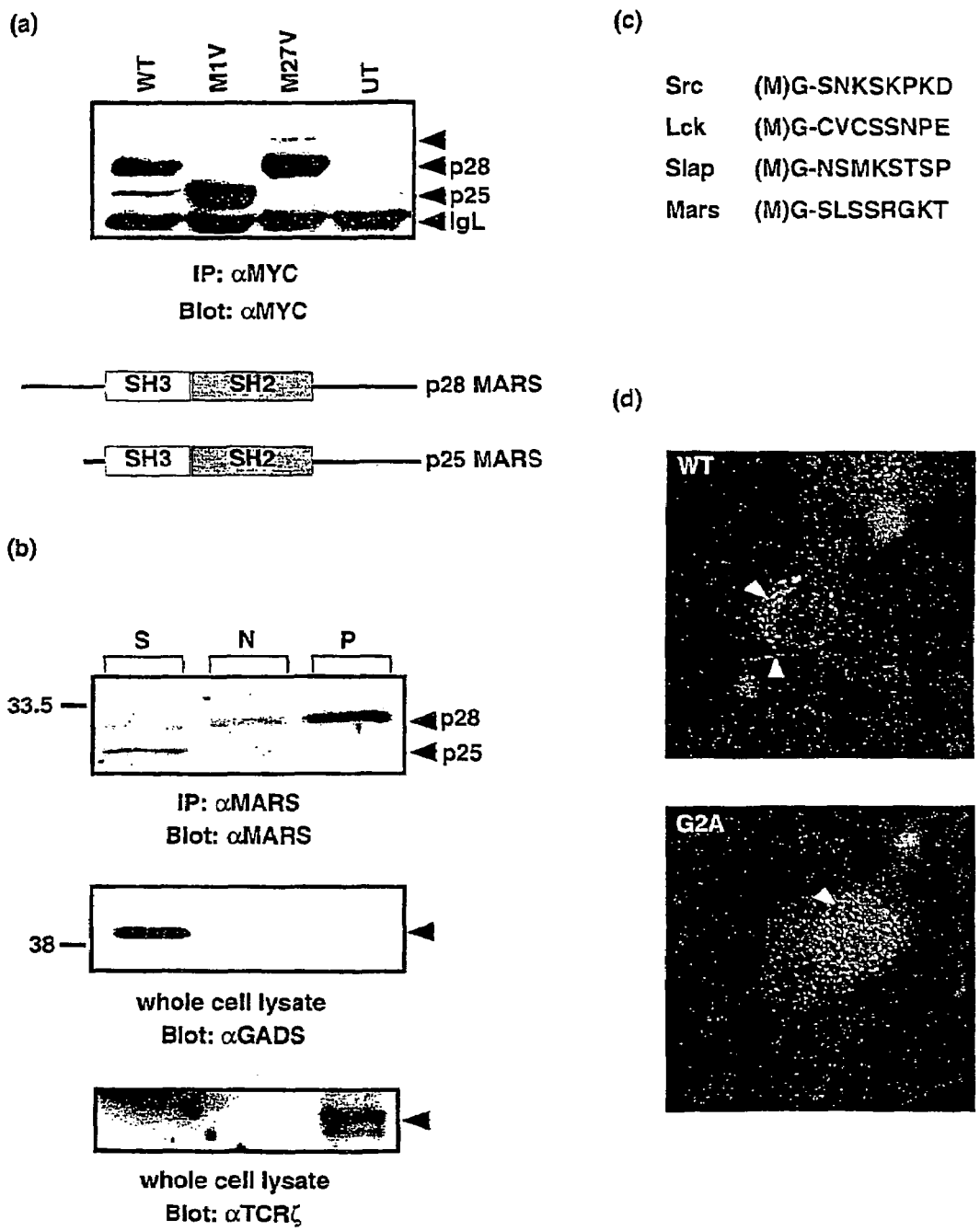
FIGURES 3A-D

```
  1  atgggaagtctgcccagcagaagaaaatctctgccaagcccaagcttgagttcctctgtc
     M  G  S  L  P  S  R  R  K  S  L  P  S  P  S  L  S  S  S  V
 61  caaggccagggaccngtgaccatggaagcagagagaagcaaggccacagccgtggccctg
     Q  G  Q  G  P  V  T  M  E  A  E  R  S  K  A  T  A  V  A  L
121  ggcagtttcccggcaggtggcccggccgagctgtcgctgagactcggggagccattgacc
     G  S  F  P  A  G  G  P  A  E  L  S  L  R  L  G  E  P  L  T
181  atcgtctctgaggatggagactggtggacggtgctgtctgaagtctcaggcagagagtat
     I  V  S  E  D  G  D  W  W  T  V  L  S  E  V  S  G  R  E  Y
241  aacatccccagcgtccacgtggccaaagtctcccatgggtggctgtatgagggcctgagc
     N  I  P  S  V  H  V  A  K  V  S  H  G  W  L  Y  E  G  L  S
301  agggagaaagcagaggaactgctgttgttacctgggaaccctggaggggccttcctcatc
     R  E  K  A  E  E  L  L  L  P  G  N  P  G  G  A  F  L  I
361  cgggagagccagaccaggagaggctcttactctctgtcagtccgcctcagccgccctgca
     R  E  S  Q  T  R  R  G  S  Y  S  L  S  V  R  L  S  R  P  A
421  tcctgggaccggatcagacactacaggatccactgccttgacaatggctggctgtacatc
     S  W  D  R  I  R  H  Y  R  I  H  C  L  D  N  G  W  L  Y  I
481  tcaccgcgcctcaccttcccctcactccaggccctggtggaccattactctgagctggcg
     S  P  R  L  T  F  P  S  L  Q  A  L  V  D  H  Y  S  E  L  A
541  gatgacatctgctgcctactcaaggagccctgtgtcctgcagagggctggcccgcttcct
     D  D  I  C  C  L  L  K  E  P  C  V  L  Q  R  A  G  P  L  P
601  ggcaaggatataccccctacctgtgactgtgcagaggacaccactcaactggaaagagctg
     G  K  D  I  P  L  P  V  T  V  Q  R  T  P  L  N  W  K  E  L
661  gacagctccctcctgtttctgaagctgccacaggggaggagtctcttctcagtgagggt
     D  S  S  L  L  F  S  E  A  A  T  G  E  E  S  L  L  S  E  G
721  ctccgggagtccctcagcttctacatcagcctgaatgacgaggctgtctctttggatgat
     L  R  E  S  L  S  F  Y  I  S  L  N  D  E  A  V  S  L  D  D
781  gcc
     A
```

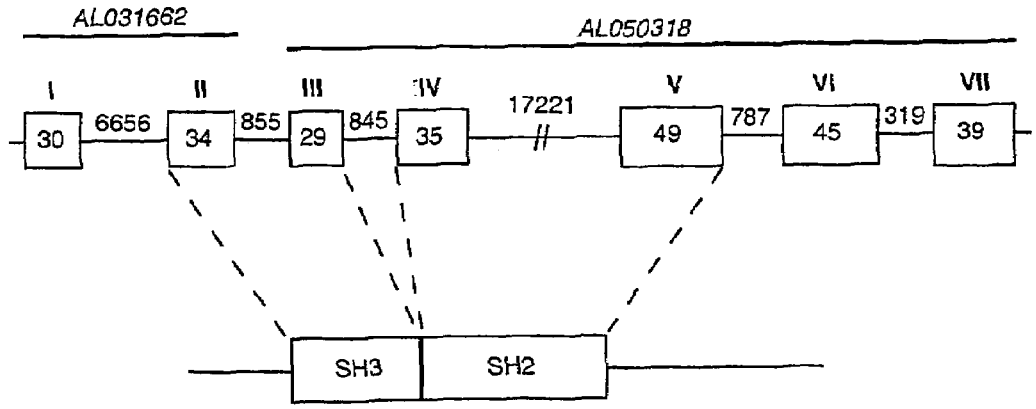

FIGURE 9B

| EXON | | 5' INTRON 3' | | | EXON |
|---|---|---|---|---|---|
| I | E A E<br>GAA GCA G | gtaggc......atctag | E<br>AG | R S<br>AGA AGC | II |
| II | V S E<br>GTC TCT GA | gtaagt......ctccag | E<br>G | D G<br>GAT GGA | III |
| III | S H G<br>TCC CAT GG | gtgagt......cgccag | G<br>G | W L<br>TGG CTG | IV |
| IV | R R G<br>AGG AGA G | gtgagt......cctcag | G<br>GC | S Y<br>TCT TAC | V |
| V | Y S E<br>TAC TCT G | gtatgg......cctcag | E<br>AG | L A<br>CTG GCG | VI |
| VI | L D S<br>CTG GAC AG | gtaaag......ccacag | S<br>C | S L<br>TCC CTC | VII |

```
huMARS: 121 RESQTRRGSYSLSVRLSRPASWDRIRHYRIHCLDNGWLYISPRLTFPSLQALVDHYSE-- 178
            RESQTRRGSYSLSVRLSRPASWDRIRHYRIHCLDNGWLYISPRLTFPSLQALVDHYSE
MARS-v: 121 RESQTRRGSYSLSVRLSRPASWDRIRHYRIHCLDNGWLYISPRLTFPSLQALVDHYSEGW 180 huMARS: 179 -----LADDICCLLKEPCVLQRAGPLPGKDIPLPVTVQRTPLNWKELDSSLLFSEAATGE 233
                 C   ++    L+RAG LP
MARS-v: 181 PAPWQGYTPTCDCAEDITQLERAGQLPPVF------------------------------ 210 huMARS: 234 ESLLSEGLRESLSFYISLNDEAVSLDDA-------------------------------- 261

MARS-v:    ------------------------------------------------------------
```

B

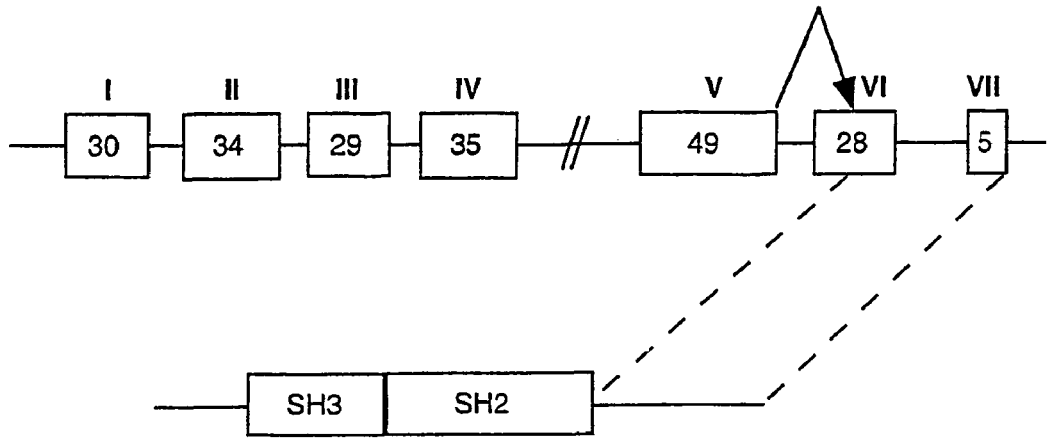

| EXON | | | 5` INTRON 3` | | | | EXON |
|---|---|---|---|---|---|---|---|
| | Y | S E | | E | G | W | |
| V | TAC | TCT G | gtatgg......ctgcag | AG | GGC | TGG | VI |
| | A | G Q | | L | P | P | |
| VI | GCT | GGA CAG | gtaaag......ccacag | CTC | CCT | CCT | VII |

# ADAPTER GENE

RELATED APPLICATION INFORMATION

This application claims the benefit under 35 U.S.C. § 371 from PCT Application No. PCT/CA01/01662, filed 26 Nov. 2001, the disclosure of which is incorporated by reference herein in its entirety, which claims the benefit of Canadian Application Serial No. 2,324,663, filed 27 Nov. 2000, the disclosure of which is incorporated by reference herein in its entirety.

FIELD OF THE INVENTION

The present invention relates to the identification and cloning of a novel gene, MARS (Modulator of Antigen Receptor Signaling), which is a putative tumor suppressor gene. The present invention also relates to the relation of the MARS gene to human cancers and its use in the diagnosis, prognosis and treatment of human cancer.

BACKGROUND OF THE INVENTION

Throughout this application, various references are cited in parentheses to describe more fully the state of the art to which this invention pertains. The disclosure of these references are hereby incorporated by reference into the present disclosure, and for convenience are listed in the appended list of references.

Engagement of the T-cell antigen receptor (TCR) is directly coupled to the activation of non-receptor protein tyrosine kinases of both the Src and SYK/ZAP-70 families, leading to the phosphorylation of intracellular signaling proteins (1, 2). Among the downstream substrates of these activated kinases are signal-transducing enzymes such as phopholipase Cγ1 (PLCγ1), and adaptor proteins such as SLP-76 and LAT (linker of activated T-cells) (3, 4). Adaptor proteins play a critical role in mediating the formation of multi-protein signaling complexes and allowing propagation of the TCR signal (5). Phosphorylated LAT recruits SH2 domain containing protein PLCγ, Grb2 and Gads, while phosphorylated SLP-76 forms complexes with Vav, Nck and p130SLAP (ADAP) (4, 6, 7). Formation of these multi-protein complexes initiates a cascade of signaling events downstream of the TCR resulting in the up-regulation of IL-2 expression via activation of nuclear transcription factors such as nuclear factor of activated T-cells (NF-AT), reorganization of the actin cytoskeleton and adhesion (8). T-cell receptor activation thus leads to T-cell proliferation which is important in immune responses.

Adaptor proteins, that negatively regulate TCR signaling, are essential for the maintenance of T-cell homeostasis, the prevention of aberrant lymphocyte activation, and for regulating the duration of immune responses (2, 9). Adaptor proteins also function in assembling inhibitory complexes that play a role in mediating this down-regulation (10). Transmembrane proteins such as SIT and PAG, for example, recruit the tyrosine kinase Csk, to the membrane (1.1, 12). Csk acts as a negative regulator of the Src family kinases, Lck and Fyn, by phosphorylating the negative regulatory site found in the tail of these enzymes (13, 14). Cytosolic adaptors of the Dok family down-regulate activated antigen receptor complexes through recruitment of inhibitory molecules RasGAP, Csk and SHIP (15).

c-Cbl, is an ubiquitously expressed protein, initially characterized as an adaptor, that functions as a negative regulator of both receptor and non-receptor tyrosine kinases (16, 17). In addition to its adaptor function, c-Cbl also possesses a RING finger domain and has E3 ubiquitin ligase activity, which promotes ubiquitination of activated tyrosine kinases (16, 18, 19). Following TCR activation, c-Cbl is recruited to the activated TCR complex and tyrosine phosphorylated (20). C-activation of TCR signaling also leads to c-Cbl association with the SYK family kinases, SYK and ZAP-70 (21-23). The association between c-Cbl and the SYK family kinases results in a decrease in the activity and protein levels of these kinases (24-26), resulting in an overall down-regulation of signaling from the TCR. The mechanism by which c-Cbl negatively regulates SYK and ZAP-70 is not fully understood, however, it has been proposed that c-Cbl ubiquitin ligase activity may be involved in this process since the RING finger domain is essential for its inhibitory activity (27, 28).

Through its association with Zap-70, c-Cbl has been demonstrated to ubiquitinate the zeta chain of the TCR (29). Therefore, c-Cbl-mediated ubiquitination of components of the TCR could result in either degradation via the proteosome or alternatively, could serve as a signal for trafficking of the activated TCR complex to the lysosome. In agreement with this hypothesis, thymocytes from mice deficient in c-Cbl, exhibit both constitutively elevated tyrosine phosphorylation levels, and have increased cell surface TCR (25, 30). Additional support for this model derives from the observation that c-Cbl ubiquitinates and promotes the internalization and subsequent degradation of receptor protein tyrosine kinases (RPTKs) such as the epidermal growth factor receptor (EGFR) (31), the colony-stimulating factor-1 receptor (CSF-1R) (32), and the platelet-derived growth factor receptor (PDGFR) (33).

Another adaptor protein that negatively regulates signaling from the activated TCR is the Src-like adaptor protein (SLAP) (34). Originally identified as a protein that interacts with the cytoplasmic domain of EphA2, SLAP has been shown to be an inhibitor of mitogenic signals downstream of the PDGFR (35, 36). Subsequently, SLAP was found to inhibit both NFAT and AP-1 activation when transiently over expressed In Jurkat T cells (34). While the mechanism by which SLAP mediates inhibitory effects remains to be elucidated, it has been demonstrated that targeted disruption of the SLAP gene in mice results in increased surface TCR expression on double positive thymocytes (37).

The applicant has cloned and characterized a novel adaptor gene, MARS (Modulator of Antigen Receptor Signaling), which is a putative tumor suppressor gene and which exhibits structural and sequence similarity to SLAP.

SUMMARY OF THE INVENTION

The present invention provides a novel MARS gene, nucleic acid encoding therefor and amino acid sequences and protein structures and related functions. Furthermore, novel human splice variants of MARS are also identified and provided. As such, the nucleic acid and amino acid sequences of the invention can be used to develop therapies and screening methods for a variety of disorders including but not limited to: myeloid malignancies such as acute myelogenous leukemia, myelodysplastic syndrome, polycythemia vera and juvenile chronic myelogenous leukemia; autoimmune disorders; immunosuppression; and malignancies related to the de-regulation of tyrosine kinases such as chronic myelogenous leukemia, chronic myelomonocytic leukemia and breast cancer. The nucleic acids and amino acid sequences of the invention also have use in the modulation of tumour properties mediated by tyrosine kinases such as angiogenesis and metastasis.

The invention is directed, in one embodiment, to the cloning and characterization of a novel murine hematopoietic adaptor protein gene designated MARS (Modulator of Antigen Receptor Signaling), which possesses sequence and structural similarity to SLAP and the Src family tyrosine kinases. The murine MARS protein consists of an N-terminal myristoylation sequence that is responsible for targeting MARS to cellular membranes, a Src homology 3 (SH3) domain and a Src homology 2 (SH2) domain, as well as a unique C-terminal region. The expression of the MARS protein appears to be unique to hematopoietic tissues and cell lines. In T-cells, both in vitro and in vivo interaction between MARS and c-Cbl has been observed, and this interaction has been mapped to the MARS C-terminus. Similar to SLAP, MARS negatively regulates TCR signaling and the inhibition of TCR signaling by MARS is dependent upon its interaction with c-Cbl.

The invention is directed in a further embodiment, to the cloning and characterization of human MARS. Human MARS is also expressed predominantly in hematopoietic cells and interacts with both c-Cbl and ZAP-70 in activated T-cells. MARS inhibits NFAT activation, may induce degradation of ZAP-70 and SYK, and reduces CD3 surface levels in a manner dependent upon its interaction with c-Cbl.

Overall, it is demonstrated that MARS negatively regulates TCR signaling by facilitating the c-Cbl-mediated ubiquitination and downregulation of the activated TCR complex by promoting internalization and degradation of activated receptor complexes. Thus MARS functions as a tumour suppressor gene in that it helps to regulate undesirable TCR-mediated signaling relating to myeloproliferative disorders of hematopoietic tissues/cells.

A full length mouse cDNA has been cloned and sequenced (SEQ ID NO:1, 1348 bp) and encodes a MARS protein of 259 amino acids (SEQ ID NO:3). The mouse coding region is 777 bp (SEQ ID NO:2). A human cDNA has also been cloned and sequenced (SEQ ID NO:4, 786 bp) and encodes a MARS protein of 261 amino acids (SEQ ID NO:5). A second human cDNA clone represents the coding region and partial UTR (SEQ ID NO:6, 737 bp) and encodes a splice variant (MARS-v), MARS short isoform of 210 amino acids (SEQ ID NO:7). SEQ ID NOS:1 through 7 are presented in Tables 1 to 7, respectively.

According to an aspect of the present invention is a MARS gene consisting of 7 coding exons localized on the long arm of chromosome 20, a region commonly deleted in myeloproliferative disorders and acute myeloid leukemia.

According to another aspect of the present invention is a MARS gene localized on the long arm of chromosome 20 consisting of 7 coding exons and 6 introns, wherein exons 2 and 3 encode a SH3 domain and exons 4 and 5 encode a SH2 domain. The 7 exons span approximately 28 Kb.

According to a further aspect of the present invention is a nucleic acid sequence encoding a MARS protein, said nucleic acid sequence selected from the group consisting of;
  a) a nucleic acid sequence encoding a coding region of the MARS gene;
  b) a nucleic acid sequence encoding a MARS gene sequence;
  c) a nucleic acid sequence encoding a MARS cDNA sequence;
  d) a nucleic acid sequence sharing at least 85% sequence identity with a), b) or c);
  e) a nucleic acid sequence which hybridizes under moderate to high stringency with a), b) c) or d);
  f) a nucleic acid complementary to any one of a) to e);
  g) a nucleic acid degeneracy equivalent to any one of a) to f); and
  h) a nucleic acid fragment of any one of a) to g) exhibiting MARS gene biological activity.

According to a further aspect of the invention is a nucleic acid sequence encoding a variant shortened MARS protein, said nucleic acid sequence selected from the group consisting of;
  a) a nucleic acid sequence of SEQ ID NO:6
  b) a nucleic acid sequence sharing at least 85% sequence identity with a);
  c) a nucleic acid sequence which hybridizes under moderate to high stringency with a) or b);
  d) a nucleic acid complementary to any one of a) to c);
  e) a nucleic acid degeneracy equivalent to any one of a) to d); and
  f) a nucleic acid fragment of any one of a) to e) exhibiting variant MARS gene biological activity.

As discussed herein, "variant" MARS gene biological activity is that activity exemplified by the protein encoded by SEQ ID NO:6, as well as sequences complementary thereto, degeneracy equivalents thereof and fragments thereof.

According to another aspect of the invention is a nucleic acid sequence selected from the group consisting of SEQ ID NO:1, SEQ ID NO:2, SEQ ID NO:4 and SEQ ID NO:6.

The invention provides isolated polynucleotides comprising nucleotide sequences encoding mammalian MARS proteins, including sequences encoding mouse and human MARS proteins and further including sequences encoding human MARS protein splice variants.

The invention also provides polynucleotides complementary to the nucleotide sequences described herein and polynucleotides which hybridize to the nucleotide sequences described herein under moderate to high stringency and polynucleotides which are degeneracy equivalents of these sequences. All such polynucleotides are encompassed within the invention and may be used in the various methods of the present invention.

The term "complementary" is used herein to refer to the sequences of polynucleotides which are capable of forming Watson and Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. Preferably, a "complementary" sequence is a sequence which an A at each position where there is a T on the opposite strand, a T at each position where there is an A on the opposite strand, a G at each position where there is a C on the opposite strand and a C at each position where there is a G on the opposite strand. Thus one skilled in the art would readily be able to determine such complementary or anti-complementary nucleic acid sequences.

Also as part of the invention are nucleic acid sequences which hybridize to one of the aforementioned nucleic acid sequences under moderate to high stringent conditions. "Stringent conditions" as used herein refers to parameters with which the art is familiar and such parameters are discussed, for example, in the latest editions of Molecular Cloning: A Laboratory Manual, J. Sambrook, et al., eds., Cold Spring Harbor Laboratory Press, Cold Spring Harbor, N.Y., or Current Protocols in Molecular Biology, F. M. Ausubel, et al., eds., John Wiley & Sons Inc., New York.

It is noted that the nucleic acid molecules described herein represent a preferred embodiment of the invention. The invention also encompasses degenerate nucleic acids that differ from the aforementioned sequences. Due to degeneracy in the genetic code, variations in the DNA sequence will result in translation of identical peptides. It is thus understood that numerous choices of nucleotides may be made that will lead to a sequence capable of directing production of the peptides or functional analogs thereof of the present invention. As a result, degenerative nucleotide substitutions are included in the scope of the invention.

In accordance with another embodiment, the invention provides alterations of the isolated MARS sequences, including the variant MARS sequence, that may be used, for example, for expression and functional studies of the encoded protein in various hematopoietic cell lines, tissues and in transgenic animal models. The MARS nucleic acid sequences can be altered using procedures such as restriction enzyme digestion, DNA polymerase fill-in, exonuclease deletion, terminal deoxynucleotide transferase extension, ligation of synthetic or cloned DNA sequences and site-directed in vitro mutagenesis, including site-directed sequence alteration using specific oligonucleotides together with PCR. The MARS nucleic acid sequence may also be altered using site-specific recombination for example.

The invention further provides probes and primers for MARS genes and nucleic acid sequences including sequences of at least 10, 15 or 20 consecutive nucleotides from the disclosed nucleotide sequences.

Probes for MARS nucleic acid sequences may be derived from the sequences of the MARS gene, its cDNA, functionally equivalent sequences, or the complements thereof. The probes may be of any suitable length, which span all of a portion of the MARS gene region, and which allow specific hybridization to the MARS gene. If the target sequence contains a sequence identical to that of the probe, the probes may be short, e.g., in the range of about 8-30 base pairs, since the hybrid will be relatively stable under even stringent conditions. If some degree of mismatch is expected with the probe, i.e., if it is suspected that the probe will hybridize to a variant region, a longer probe maybe employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 Kb, usually fewer than about 1.0 Kb, from a polynucleotide sequence encoding MARS are preferred as probes. This definition therefore includes probes of sizes 8 nucleotides through 2000 nucleotides. Thus, this definition includes probes of 8, 12, 15, 20, 25, 40, 60, 80, 100, 200, 300, 400, 500 nucleotides, or probes having any number of nucleotides within these values (e.g., 9, 10, 11, 16, 23, 30, 38, 50, 72, 121, etc. nucleotides), or probes having any number of nucleotides between 8 and the number shown in any one of SEQ ID NO:1, SEQ ID NO:2, SEQ ID NO:4 and SEQ ID NO:6. The probes may also be used to determine whether mRNA encoding MARS is present in a cell or tissue.

Similar considerations and nucleotide lengths are also applicable to primers which may be used for the amplification of all or part of the MARS gene. Thus, a definition for primers includes primers of 8, 12, 15, 20, 25, 40, 60, 80, 100, 200, 300, 400, 500 nucleotides, or primers having any number of nucleotides within these values (e.g., 9, 10, 11, 16, 23, 30, 38, 50, 72, 121, etc, nucleotides), or primers having more than 500 nucleotides, or any number of nucleotides between 500 to 9000. The primers may also be used to determine whether mRNA encoding MARS is present in a cell or tissue. The present invention includes all novel primers having at least 8 nucleotides derived from the MARS gene locus for amplifying the MARS gene, its complement or functionally equivalent nucleic acid sequences. The present invention does not include primers which exist in the prior art. That is, the present invention includes all primers having at least 8 nucleotides with the proviso that it does not include primers existing in the prior art.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g. methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the MARS gene. The recombinant construct may be capable of replicating autonomously in a host cell. Alternatively, the recombinant construct may become integrated into the chrosomosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

The invention includes isolated nucleic acids that comprise a nucleic acid sequence having at least 70% identity, more preferably at least 75% identity, and still more preferably at least 80%, 85%, 90% and 95% to any one of the sequences of SEQ ID NO:1, SEQ ID NO:2, SEQ ID NO:4 and SEQ ID NO:6. One skilled in the art would readily comprehend that nucleic acid sequence identity is the percentage of nucleotides in a candidate sequence that are identical with the nucleotides in the subject sequence when aligning the sequences. One skilled in the art would also readily be able to determine the parameters for aligning such sequences and use any appropriate algorithms and computer software in order to achieve the maximal alignment of sequences over their entire length. To the nucleotide sequences disclosed herein, "similarity" being determined by the % matching of the respective nucleotide sequences when compared by sequence comparison algorithms such as BLAST and FASTA.

The invention also provides substantially purified mammalian MARS proteins, including substantially purified mouse and human MARS proteins, and further including human MARS splice variants such as MARS short isoform described herein. The invention further provides functional fragments of the MARS proteins disclosed herein. The invention further provides antigenic determinants of the MARS proteins disclosed herein, including sequences of at least 5, 10 or 20 consecutive amino acids from the disclosed protein sequences.

According to an aspect of the present invention is an amino acid sequence selected from the group consisting of SEQ ID NO:3, SEQ ID NO:5, and SEQ ID NO:7.

Using the polynucleotide and protein sequences disclosed herein, one of ordinary skill in the art is now enabled to identify allelic variants and heterospecific homologues of the MARS genes and proteins described herein. Alielic variants of the genes described herein include normal variants of the nucleotide sequences described herein and also mutant versions of the MARS genes described herein. Heterospecific homologues may be from mammalian species other than those described herein or from non-mammalian species such as invertebrate species.

The invention further includes proteins which have at least 75%, preferably at least 80% and more preferably at least 90% or 95% amino acid identity to the amino acid sequences disclosed herein when compared by sequence comparison programs such as BLAST and FASTA.

The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native MARS sequence, preferably in excess of about 90%, and more preferably at least about 95% homologous. Also included are proteins encoded by DNAs which hybridize under high or low stringency conditions to MARS encoding nucleic acids and closely related polypeptides proteins retrieve by antisera to the MARS protein.

The MARS polypeptide maybe that shown in SEQ ID NO:3, SEQ ID NO:5 or SEQ ID NO:7 which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the MARS polypeptide. Such polypeptides may have an amino acid sequence which differs from that set forth in SEQ ID NO:3, SEQ ID NO:5 or SEQ ID NO:7 by one or more of addition, substitution, deletion or insertion of one or more amino acids. Preferred polypeptides have MARS function.

Substitutional variants or "analogs" typically contain the exchange of one amino acid for another at one or more sites within the protein, and may be designed to modulate one or more properties of the polypeptide, such as stability against proteolytic cleavage, without the loss of other functions or 0.10 properties. The present invention also relates to functionally equivalent variants of the peptides. "Functionally equivalent variants" or "analogs" includes peptides with partial sequence homology, peptides having one or more specific conservative and/or non-conservative amino acid changes, peptide conjugates, chimeric proteins, fusion proteins and peptide encoding nucleic acids. The functionally equivalent variants maintain the biological activity of the native peptide. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well know in the art and typically include substitutions within the following groups: glycine, alanine; valine; isoleucine; leucine; aspartic acid, glutamic acid; asparagine, glutamine; serine, threonine; lysine, arginine, tyrosine and phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with a MARS polypeptide. Since it is the interactive capacity and nature of a protein which defines that protein's biological functional activity, certain amino acid substitutions can be made in a protein sequence, and its underlying DNA coding sequence, and nevertheless obtain a protein with line properties. In making such changes, the hydropathic index of amino acids may be considered. The importance of the hydrophobic amino acid index in confering interactive biological function on a protein is generally understood in the art (Kyte and Doolittle, 1982). Alternatively, the substitution of like amino acids can be made effectively on the basis of hydrophilicity. The importance of hydrophilicity in confering interactive biological function of a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

The invention also provides for peptide mimetics of MARS protein or peptide sequence. The term "peptide mimetic" or "mimetic" is intended to refer to a substance which has the essential biological activity of the MARS polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of natural MARS polypeptide.

The invention further provides nucleic acid constructs, vectors and host cells containing the isolated nucleic acids described above. Vectors may enable the expression of MARS proteins when the MARS encoding sequence is operably linked to a suitable promoter sequence. The invention includes host cells transformed with such vectors, whereby production of a selected MARS protein is enabled, by suitable culturing of the host cell and harvesting of the expressed MARS protein.

"Operably linked" refers to a juxtaposition wherein the components so described are in a relationship permitting them to function in their intended manner. For instance, a promoter is operably linked to a coding sequence if the promoter affects its transcription or expression.

The invention further provides methods of detecting a polynucleotide comprising a portion of the MARS gene or its expression product in a sample. Such methods may further comprise the step of amplifying the portion of the MARS gene and may further include a step of providing a set of polynucleotides which are primers for amplification of said portion of the MARS gene. The method is useful for the diagnosis of the predisposition to cancer or the diagnosis or prognosis of cancer especially hematopoietic cancers. Useful diagnostic techniques include but are not limited to FISH, direct DNA sequencing, PFCE analysis, southern blot analysis, single stranded conformation analysis (SSCA), Rnase protection assay, allele-specific oligonucleotide (ASO), dot blot analysis and PCR-SSCP.

The invention also provides kits for detecting in a sample a polynucleotide comprising a portion of the MARS gene. The kits comprising a portion of the MARS gene as a polynucleotide complementary to a portion of the MARS gene, and instructions for use. Alternatively, kits may comprise one or more MARS antibodies for detecting a portion of the MARS protein.

The invention further provides methods of preparing a polynucleotide comprising polymerizing nucleotides to yield a sequence comprised of at least eight consecutive nucleotides of the MARS sequence, SEQ ID NO:1, SEQ ID NO:2, SEQ ID NO:4 or SEQ ID NO:6, and methods of preparing a polypeptide comprising polymerizing amino acids to yield a sequence comprising at least five amino acids encoded by the MARS gene.

In addition, the present invention provides methods of screening drugs (i.e. small molecule inhibitors and/or activators) for cancer therapy to identify suitable drugs for restoring or up-regulating MARS gene product function.

The present invention also provides the means necessary for production of gene-based therapies directed at cancer cells, especially hematopoietic cancerous cells. The therapeutic agents may take the form of polynucleotides comprising all or a portion of the MARS nucleic acid sequence placed in appropriate vectors or delivered to target cells in more direct ways such that the function of the MARS protein is reconstituted. Therapeutic agents may also take the form of polypeptides based on either a portion of, or the entire protein sequence of MARS. These may functionally replace the activity of MARS in vivo. Ex vivo, therapies are also encompassed Within the invention. Isolated patient lymphocytes may be treated ex vivo with a suitable gene-based therapy and then reintroduced to the patient.

In an aspect of the invention, is a method of for the treatment of myeloid malignancies, the method comprising:
a) transfecting lymphocytes ex vivo with a nucleic acid encoding a functional MARS protein; and
c) infusing the patient with the stimulated cells.

In accordance with a further embodiment, transformed cell lines may be created, either prokaryotic or eukaryotic, transformed with the nucleic acids described or enabled herein. Suitable recombinant techniques to create such cell lines are well known to those of skill in the art and are described, for example, in Sambrook et al. ((1989) "Molecular Cloning; A Laboratory Manual", $2^{nd}$ ed., Cold Spring Harbor Laboratory Press, Cold Spring Harbor, N.Y.).

Such cell lines are useful, for example, for producing MARS protein or any desired functional domain or fragment thereof. Such in vitro expression enables production of a MARS protein in quantity, the expressed protein being purified by conventional protein purification methods.

The MARS protein may be isolated and purified by methods selected on the basis of properties revealed by its sequence. Purification can be achieved by protein purification procedures such as chromatography methods (gel-filtration, ion-exchange and immunoaffinity), by high-performance liquid chromatography (HPLC, RP-HPLC, ion-exchange HPLC, size-exclusion HPLC, high-performance chromatofocusing and hydrophobic interaction chromatography) or by precipitation (immunoprecipitation). Polyacrylamide gel electrophoresis can also be used to isolate the MARS proteins based on the molecular weight of the protein, charge properties and hydrophobicity.

Similar procedures to those mentioned can be used to purify the protein from cells transfected with vectors containing a MARS gene (e.g. baculovirus systems, yeast expression systems and eukaryotic expression systems).

The purified proteins can be used in further biochemical analyses to establish secondary and tertiary structure which may aid in the design of pharmaceuticals to interact with the protein (or a binding partner), alter the protein charge configuration or charge interaction with other proteins or alter its function.

The MARS proteins can also be purified from the creation of fusion proteins which are expressed and recovered from prokaryotic or eukaryotic cells. The fusion proteins can be purified by affinity chromatography based upon the fusion vector sequence. The MARS protein can then be further purified from the fusion protein by enzymatic cleavage of the fusion protein.

"Protein modifications or fragments" are provided by the present invention for MARS polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands, which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See, e.g., Sambrook et al., 1989 or Ausubel et al., 1992. MARS chimeric proteins and peptides are also within the scope of the invention.

Any of the MARS proteins, peptides, mimetics or modified forms thereof, may be used in pharmaceutical compositions to treat lymphoproliferative disorders.

Besides substantially full-length polypeptides, the present invention provides for biologically active immunological fragments of the polypeptides. Immunological activities include both immunogenic function in a target immune system, as well as sharing of immunological epitopes for binding, serving as either a competitor or substitute antigen for an epitope of the MARS protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8-10 such amino acids. Methods of determining the spatial conformation of such amino acids are known in the art.

The invention further enables the production of antibodies, monoclonal and polyclonal, which bind selectively to a MARS protein or to a fragment, antigenic determinant or functional domain thereof. These antibodies are useful, for example, for immunoaffinity purification of MARS proteins and for detection of MARS proteins in cells or tissues.

With the knowledge of the amino acid sequences for the long and short (variant) MARS proteins, there is provided antibodies which recognize epitopes within these proteins and which can be raised to provide information on the characteristics of the protein as well as for any mutant form of these proteins. The generation of antibodies enables the visualization of the protein in mammalian cells and tissues using techniques such as but not limited to western blotting, as known to those in the art. Antibodies to the MARS proteins also allow for the use of immunocytochemistry and immunofluorescence techniques in which the proteins are visualized directly in cells and tissues. This is most helpful in order to establish the subcellular location of the protein and the tissue specificity of the protein, as described herein.

In general, methods for the preparation of antibodies are well known. In order to prepare polyclonal antibodies, fusion proteins containing defined portions or all of the MARS proteins or any of their alternative transcripts can be synthesized in bacteria by expression of corresponding DNA sequences in a suitable cloning vehicle. The protein can then be purified, coupled to a carrier protein and mixed with Freund's adjuvant (or other suitable adjuvant, to help stimulate the antigenic response by the rabbits) and injected into rabbits or other laboratory animals. Alternatively, protein can be isolated from cultured cells expressing the protein. Following booster injections at bi-weekly intervals, the rabbits or other laboratory animals are then bled and the sera isolated. The sera can be used directly or purified prior to use, by affinity chromatography. The sera can then be used to probe protein extracts run on a polyacrylamide gel to identify the MARS proteins, alternative transcripts or any mutant thereof. Alternatively, synthetic peptides can be made to the antigenic portions of these proteins and used to innoculate the animals.

Methods to produce monoclonal antibodies which specifically recognize mammalian MARS proteins or portions-thereof, are known in the art. In general, cells actively expressing the protein are cultured or isolated from tissues and the cell extracts isolated. The extracts or recombinant protein extracts, containing the MARS protein, are injected in Freund's adjuvant into mice. After being injected 9 times over a three week period, the mice spleens are removed and resuspended in phosphate buffered saline (PBS). The spleen cells serve as a source of lymphocytes, some of which are producing antibody of the appropriate specificity. These are then fused with a permanently growing myeloma (preferably non-MARS expressing) partner cell, and the products of the fusion are plated into a number of tissue culture wells in the presence of a selective agent such as HAT. The wells are then screened to identify those containing cells making useful antibody by ELISA. These are then freshly plated. After a period of growth, these wells are again screened to identify antibody-producing cells. Several cloning procedures are carried out until over 90% of the wells contain single clones which are positive for antibody production. From this procedure a stable lines of clones is established which produce the antibody. The monoclonal antibody can then be purified by affinity chromatography using Protein A or Protein G Sepharose.

Generally, the invention relates to the therapy of any cancer or autoimmune conditions where there is inappropriate T-cell activation.

The invention also relates to the therapy of human cancers which result from a mutation in the MARS gene or the lack of a functioning MARS gene, including gene therapy, protein replacement therapy and protein mimetics. The invention further relates to the screening of drugs for cancer therapy. Finally, the invention relates to the screening of the MARS gene for its presence, mutations, which are useful for diagnosing the predisposition to certain immunoproliferative disorders.

The invention further provides a method for detecting a mutation in a MARS gene associated with tumor formation comprising obtaining a nucleic acid sample from a subject having a tumor, sequencing a MARS gene from the sample and comparing that sequence with the normal MARS sequence.

The invention further provides a method for detecting a variant MARS nucleic acid sequence associated with tumor formation comprising obtaining a nucleic acid sample from a subject having a tumor, sequencing a MARS gene from the sample and comparing that sequence with the variant MARS sequence.

The invention also provides screening kits for detecting a loss of MARS function in leukemia. In one aspect, is a kit for screening for an alteration in MARS gene in a human subject which comprises at least one antibody which specifically binds to a wild-type MARS polypeptide but not a variant MARS polypeptide or which specifically binds to an epitope of a variant MARS polypeptide.

The invention further enables methods for identifying proteins or other compounds which bind to or interact with a MARS protein. The identification of such binding partners provides new targets for pharmaceutical intervention and provides methods for screening candidate compounds for their ability to modulate the activity of a MARS protein.

One of skill in the art is now enabled to screen tissue homogenates or cell lysates for proteins or other compounds which bind to a MARS protein. Once identified, such compounds may themselves provide new pharmaceutical agents or may serve as lead compounds for the development of further pharmaceutical agents. Methods of screening for binding partners of a novel protein are well known to those in the art and include techniques such as affinity chromatography, immunoprecipitation using antibodies specific for a MARS protein, the BIAcore system of Pharmacia and the yeast two-hybrid system.

The invention provides a method for identifying compounds which can modulate the expression of a MARS gene comprising contacting a cell with a candidate compound wherein said cell includes a regulatory region of a MARS gene operably joined to a coding region; and detecting a change in expression of said coding region.

The invention further provides a method for identifying compounds which can selectively bind to a MARS protein comprising the steps of providing a preparation including at least one MARS protein or or portion thereof;

contacting said preparation with a sample including at least one candidate compound; and detecting binding of said MARS protein or portion thereof to said candidate compound.

The invention further provides a method for identifying compounds which can modulate activity of a MARS protein comprising the steps of contacting a cell expressing a normal or mutant MARS protein with at least one candidate compound; and detecting a change in a marker of said activity.

In general, various assay screening methods may be used to identify any type of molecule that inhibits or activates MARS.

The invention further provides methods for reducing tyrosine kinase activity of hematopoietic cells/tissues, for reducing the expression of CD3ε on cell surfaces of hematopoietic cells or for downregulating the activity of the TCR complex.

The present invention also provides for the production of transgenic animals in which MARS-encoding sequences are expressed or in which MARS genes have been inactivated. Such transgenic animal models are useful for the study of the mechanisms involved in myeloproliferative disorders associated with lack of, reduced or altered MARS expression and/or function. Transgenic animal models also provide a model system to study and develop effective therapies for disorders involving the MARS gene and its function. In the present invention transgenic animal models of autoimmunity and leukemia are particularly useful for the study and identification of effective therapies.

Animal species suitable for use include, but are not limited to, mice, rats, hamsters, guinea pigs, rabbits, cats, dogs, pigs, goats and sheep.

To create a transgenic animal, a nucleotide sequence encoding at least a functional domain of a heterologous or homologous, normal, mutant or variant MARS protein is introduced recombinantly into the genome of the animal. Such animals provide animal models for further investigation of the function of the MARS protein.

In a further embodiment, knock out animals may be produced, in which one or both endogenous MARS genes have been partially or completely deleted by techniques described in the scientific literature, such as homologous recombination or gene targeting of exogenous sequences. These animals provide a model for study of the effects of loss of function of the MARS gene and also provide a tool for drug screening, by studying the effect candidate drug compounds on a deficit observed in the knock out animal. In view of the role of the MARS gene as a putative tumor suppressor, knock out animals provide a useful animal model of myeloproliferative disorders.

The creation of transgenic animals or of knock out animals can be carried out by techniques which are now well known to those of skill in the art. For example, to create such models using mice, techniques are described, for example in Hogan et al. ((1986), "Manipulating the Mouse Embryo", Cold Spring Harbor Laboratory Press, Cold Spring Harbor, N.Y.).

SUMMARY OF THE DRAWINGS

The present invention will be further understood from the following description with reference to the Figures, in which:

FIG. 1A shows the full-length murine MARS cDNA (SEQ ID NO:1) and translated amino acid sequence. Initiation methionines are indicated in bold-face type; a consensus polyadenylation signal sequence is indicated in bold-face type and underlined. 5H3 is underlined and the SH2 domain is indicated in bold italics. This sequence data has been submitted to Genbank, and is available under the accession number AF287467;

FIG. 1B shows the alignment of the amino acid sequences of murine MARS (SEQ ID NO:3) and SLAP. Conserved residues are indicated by letters and similar amino acids are denoted by '+';

FIG. 1C shows a schematic representation of the murine MARS and SLAP proteins. The percentage amino acid identities between the individual domains are indicated. 'M' designates the site of alternative translation initiation giving rise to a MARS translation isoform (refer to FIG. 3A);

FIG. 2A shows a northern blot illustrating the expression profile of MARS mRNA and protein in murine tissues and cell lines. RT-PCR analysis of MARS mRNA expression in murine tissues and the murine embryo. cDNA derived from the tissues of an 8-week-old mouse were PCR amplified with MARS-specific PCR primers (upper panel; 343 base pair product). Plasmid DNA containing the full-length MARS cDNA was used as a positive control and a negative control (no cDNA) was used to guard against contaminating cDNA in the PCR reagents. Amplification of the cDNAs with mouse α-Actin specific primers (490 base pair product) was used as a control for cDNA quantity and quality;

FIG. 2B shows a western blot illustrating generation of MARS specific antisera. Rabbit antisera generated against a GST fusion protein containing the murine MARS C-terminus (anti-MARS-C) was tested on transfected myc-tagged (crude antisera) and endogenous MARS proteins (affinity purified antibody; IgH=immunoglobulin heavy chain);

FIG. 2C shows a western blot illustrustring expression of MARS protein in murine tissues. 1 mg of total protein lysates isolated from the tissues of an 8-week-old mouse was immunoprecipitated and Western blotted with crude rabbit anti-mouse MARS-C polyclonal antibody;

FIG. 2D shows a western blot illustrating expression of MARS protein in murine cell lines. 1 mg of total protein lysates from various hematopoietic and non-hematopoietic cell lines was immunoprecipitated and Western blotted with affinity purified rabbit anti-mouse MARS-C polyclonal antibody;

FIG. 3A shows a western blot illustrating subcellular localization of MARS protein isoforms. (a) Identification of MARS alternative translation isoforms via mutagenesis. Methionine residues at positions 1 and 27 in the primary amino acid sequence were mutated to valine residues by PCR-based mutagenesis. Mutant proteins were expressed in COS cells and immunoprecipitated/immunoblotted with antimyc (9E10) antibody. (IgL=immunoglobulin light chain) Alternative translation initiation from the MARS transcript result in protein isoforms of approximately ~28 and ~25 kDa, respectively. The p28 isoform contains a myristoylation sequence at its N-terminus (*);

FIG. 3B shows a western blot illustrating subcellular localization of endogenous MARS protein in DO11.10 murine T-cells as determined by subcellular fractionation. Soluble (5), nuclear (N), and pellet (P) fractions were immunoprecipitated and immunoblotted with anti-MARS-C antibody (upper panel). Additionally, lysates were resolved by SDS-PAGE and immunoblotted with anti-GADS (middle panel) and anti-TCRzeta (lower panel) antibodies;

FIG. 3C shows the alignment of Src family (Src and Lck), SLAP and MARS N-terminal amino acid sequences indicating a consensus myristoylation sequence ($MGX_{14}S$);

FIG. 3D shows differential localization of wild type MARS (top panel) and G2A mutant MARS (bottom panel) proteins transiently expressed in Hela cells as assessed by immunostaining. Myc-tagged MARS proteins were immunostained with anti-myc (9E10) primary antibody in conjunction with an Alexa488-labelled anti-mouse secondary antibody (green fluorescence), while nuclei were stained with propidium iodide (red fluorescence). Stained cells were visualized by confocal microscopy as described in the Materials and Methods. Arrows indicate the areas of MARS protein localization;

FIG. 6(A) Inhibition of NFAT activation by MARS requires a functional SH2 domain, and the c-Cbl binding region. Jurkat E6.1 cells were co-transfected with empty vector or MARS expression constructs and an NFAT luciferase reporter construct. Relative NFAT activation was assessed in unstimulated (−) and anti-CD3 stimulated (+) cells as described. Cell lysates were immunoblotted with anti-myc (9E10) antibody to check relative expression levels of the MARS constructs. FIG. 6(B) Wild-type MARS augments Cbl-mediated inhibition of NFAT activation following TCR stimulation. Jurkat E6.1 cells were co-transfected with empty vector, Cbl, and MARS expression constructs, as well as an NFAT luciferase reporter construct. NFAT activation and expression levels of myctagged MARS proteins was assessed as described in (A). Expression of ectopically expressed HA-c-Cbl was detected by immunoblotting with anti-HA antibody;

FIG. 9A shows the nucleotide and amino acid sequence of the MARS human homologue;

FIG. 9B shows the genomic structure of the MARS human homologue. The numbering refers to coding exons (I-VII) and the numbers within the boxes denote the number of amino acids encoded by each of the exons. The number of base pairs for each of the respective introns is also indicated.

FIG. 9C shows intron-exon highlighting of the sequence context of the splice junctions of the human MARS gene and the adherence to the GT/AG rule for eukaryotic splicing. The numbering refers to the coding exons. The corresponding amino acid sequences are indicated by letters above the nucleotide sequences which start and complete each of the exons;

DETAILED DESCRIPTION OF THE INVENTION

Figure 4:
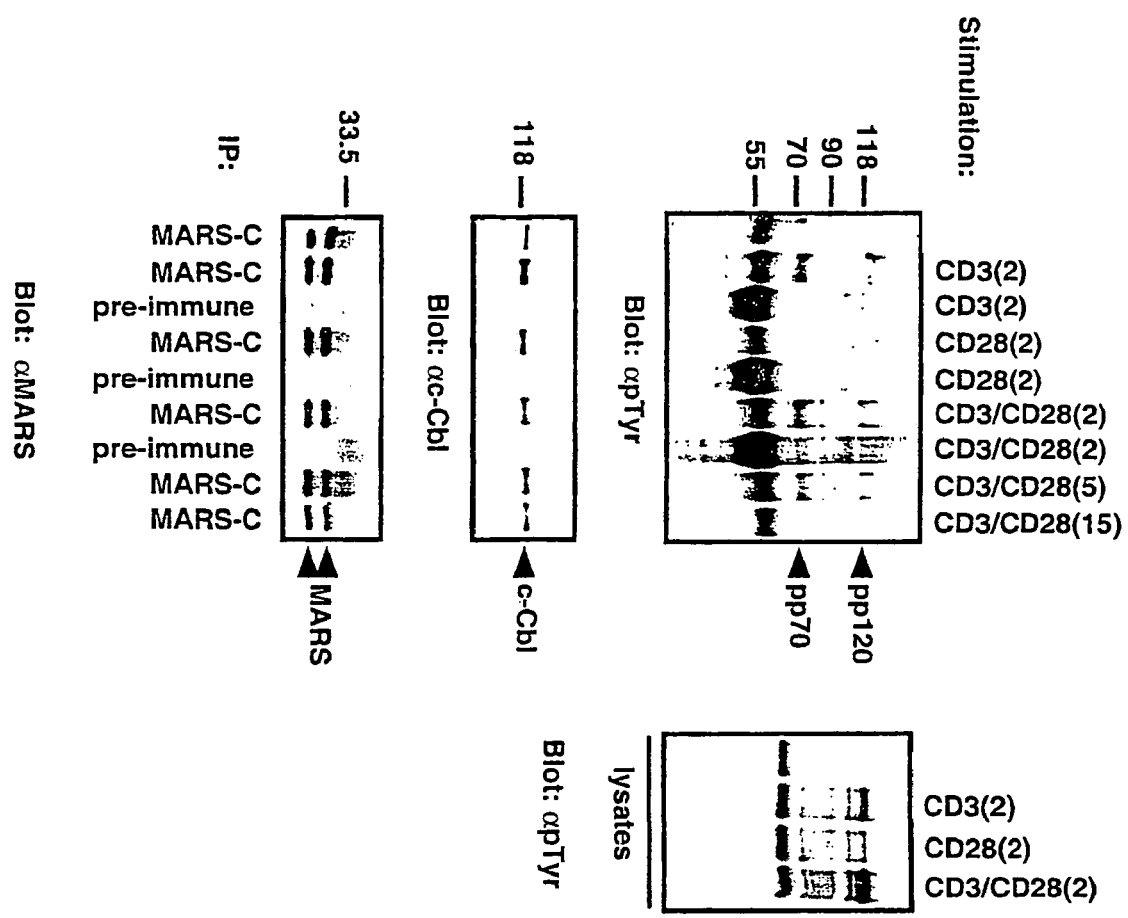
FIG. 4 shows western blots illustrating MARS associating in vivo with tyrosine phosphorylated proteins following T-cell receptor crosslinking. Thymocytes were isolated from 6-week-old mice and stimulated with either anti-CD3 alone, anti-CD28 alone, or costimulated with anti-CD3 and anti-CD28 antibodies for the indicated periods of time (as indicated in parentheses). Lysates from stimulated thymocytes ($5 \times 10^7$) were immunoprecipitated with affinity purified anti-MARS antibody and immunoblotted. Upper panel: anti-phosphothyrosine immunoblot; middle panel: anti-cCbl immunoblot; lower panel: blot was stripped and reprobed with affinity purified anti-MARS-C antibody.

The present invention is directed to a novel mammalian gene which encodes a novel adapter protein. The applicant has isolated and characterized a MARS (Modulator of Antigen Receptor Signaling) gene which exhibits structural and sequence similarity to SLAP. Both mouse and human MARS have been isolated and characterized as well as a MARS human splice variant. Both the mouse and human MARS proteins have been demonstrated to negatively regulate tyrosine kinase mediated signaling. The MARS human splice variant is demonstrated to have mutant activity, i.e., does not negatively regulate tyrosine mediated signaling.

A full length mouse cDNA has been cloned and sequenced (SEQ ID NO:1) and encodes a MARS protein of 259 amino acids (SEQ ID NO:3). The mouse coding region is 777 bp (SEQ ID NO:2). Two human cDNA's have been cloned and sequenced. The first cDNA clone (SEQ ID NO:4) encodes a MARS protein of 261 amino acids (SEQ ID NO:5). The second cDNA clone (SEQ ID NO:6) encodes a shorter splice variant, MARS short isoform, of 210 amino acids (SEQ ID NO:7).

The identification and characterization of the MARS nucleic acid and amino acid sequences, along with the characterization of MARS function, now enables the development of therapies for those conditions where there is inappropriate T-cell activation such as for example in myeloid malignancies and in autoimmune diseases.

A. Mouse MARS

Cloning of Murine MARS cDNA

The SH2 domain sequence of the hematopoietic adaptor molecule Gads (Grb2-related adaptor dowstream of Shc, (38) was used to do an in silico screen of high throughput genomic sequences (htgs) in the NCBI's Genbank sequence database, using the BLAST algorithm. A human genomic clone harbouring the partial sequence of a novel SH2 domain-containing protein that had weak similarity to the Gads SH2 was identified (Accession No. AL0503 18). The genomic clone was subsequently used to search the Genbank mouse EST database for related cDNAs. Two mouse ESTs encoding the 5' end of a novel cDNA were identified (Accession No. A1510095 and AA959151) and the full-length 1348 base pair cDNA was cloned by 3' RACE. The full-length mouse cDNA contains relatively short 5' and 3' UTRs, and an open-reading frame of 777 base pairs, which encodes a putative protein of 259 amino acids with a predicted molecular weight of 28.5 kDa (FIG. 1A). Based on functional characterization described in this manuscript, the new gene and its protein product was named MARS (Modulator of Antigen Receptor Signaling). MARS contains a serine-rich N-terminus with a myristylation sequence ($MGX_{14}S$) at the extreme N-terminus, SH3 and SH2 protein interaction domains, and a unique C-terminal domain. MARS is most similar to the Src-like adaptor protein (SLAP) (36), and the Src family of tyrosine kinases. MARS shares both sequence similarity and structural organization with SLAP and, therefore, represents the second member of a SLAP family of adaptors (FIG. 1B,C).

An expression profile of MARS mRNA was obtained by RT-PCR analysis of total RNA isolated from the tissues of an 8-week-old mouse and from embryos at day 16. The MARS transcript is widely expressed in adult tissues, and in the developing mouse embryo (e16) (FIG. 2A).

In order to profile MARS protein expression, antibodies were generated against a C-terminal epitope of MARS (anti-MARS-C). The antiserum was tested for its ability to recognize both transfected MARS-myc protein, as well as endogenous MARS in CTLL-2 cells (FIG. 2B). In both MARS-myc transfected COS-1 cells and untransfected CTLL-2 cells, the anti-MARS-C antiserum specifically detected a protein doublet, which migrated with slower mobility in the transfected COS cells, presumably as a result of the added epitope tag. The upper band observed in CTLL-2 cells migrated with an apparent molecular weight of 28 kDa, in keeping with the predicted molecular mass of 28.5 kDa, while the smaller form of MARS with an apparent molecular weight of 25 kDa arises from an internal translation initiation site (FIG. 3).

The expression of MARS protein in murine tissues and murine hematopoietic and non-hematopoietic cell lines was assessed by immunoprecipitation and western blot analysis (FIG. 2C, D). MARS was detected in extracts of both thymus and spleen, and at lower levels in lung. MARS protein was not detected in the other tissues surveyed including liver, heart and brain, indicating that MARS expression is restricted to hematopoietic cells (FIG. 2D). MARS was abundantly expressed in murine BaF3 cells (proB cells), DOI 1.10 and CTLL-2 cells (T-cells), but not cell lines of mast cell (RBL-2H3, p815), or macrophage (RAW264.7) origin, or in either of the two non-hematopoietic cell lines tested (NIH 3T3 and MEF cell lines) (FIG. 2D).

Identification and Differential Subcellular Localization of MARS Protein Isoforms Inspection of the MARS cDNA sequence revealed a putative alternative translation initiation site at methionine 27 (M27) of the MARS protein sequence, suggesting that the two prominent anti-MARS reactive protein species observed may represent alternative translation products of MARS. MARS mutants in which each of the methionine residues (M1 and M27) was mutated to valine were generated and transiently transfected into COS cells. The M1V mutant produced a protein that co-migrated with the 25 kDa form of MARS (p25) while the M27V product co-migrated with the 28 kDa species (p28) confirming that use of alternative translation initiation gives rise to two forms of MARS protein (FIG. 3A). The smaller 25 kDa MARS isoform lacks both the N-terminal myristoylation sequence and the serine-rich region present at the amino-terminus of the long isoform. p25 MARS is expressed at low levels relative to p28 in both transfected cells and endogenously in mouse cell lines. Interestingly, in murine tissues, the relative expression is reversed in the thymus, suggesting that utilization of the internal translation initiation site may be regulated (FIG. 2C). In transiently transfected COS cells, an additional higher molecular weight form of MARS was also observed that was associated with the expression of p28 (FIG. 3A). p28 MARS retains both the myristylation sequences and a serine rich region, and thus the slow migrating form of MARS may arise from post-translational modification. The slower migrating band is no longer detected following phosphatase treatment of MARS immunoprecipitates, nor was it detected by anti-phosphotyrosine antibodies, suggesting that phosphorylation on serine and threonine residues contributes to the formation of this species (data not shown).

The localization of endogenous MARS protein isoforms was assessed by subcellular fractionation of DO 11.10 T-cells (FIG. 3B). The p28 MARS isoform was found predominantly in the pellet fraction, indicative of association with cell membranes, presumably due to its N-terminal myristoylation. In contrast, the p25 isoform, which lacks the myristoylation sequence, was found predominantly in the soluble cytosolic fraction. The subcellular localization of MARS was also assessed by immunofluorescent staining of MARS transfected HeLa cells. Wild type MARS localized to both the plasma membrane as well as intracellular vesicles. In contrast, a mutant form of MARS, in which the glycine (G2) within the myristoylation sequence was changed to an alanine residue (G2A), no longer associated with cell membranes and appeared mislocalized to the nucleus, confirming that myristoylation of p28 MARS is important for its subcellular localization (FIG. 3D).

MARS Binds c-Cbl and Zap-70 Following T-Cell Receptor Cross Linking

Figure 5:
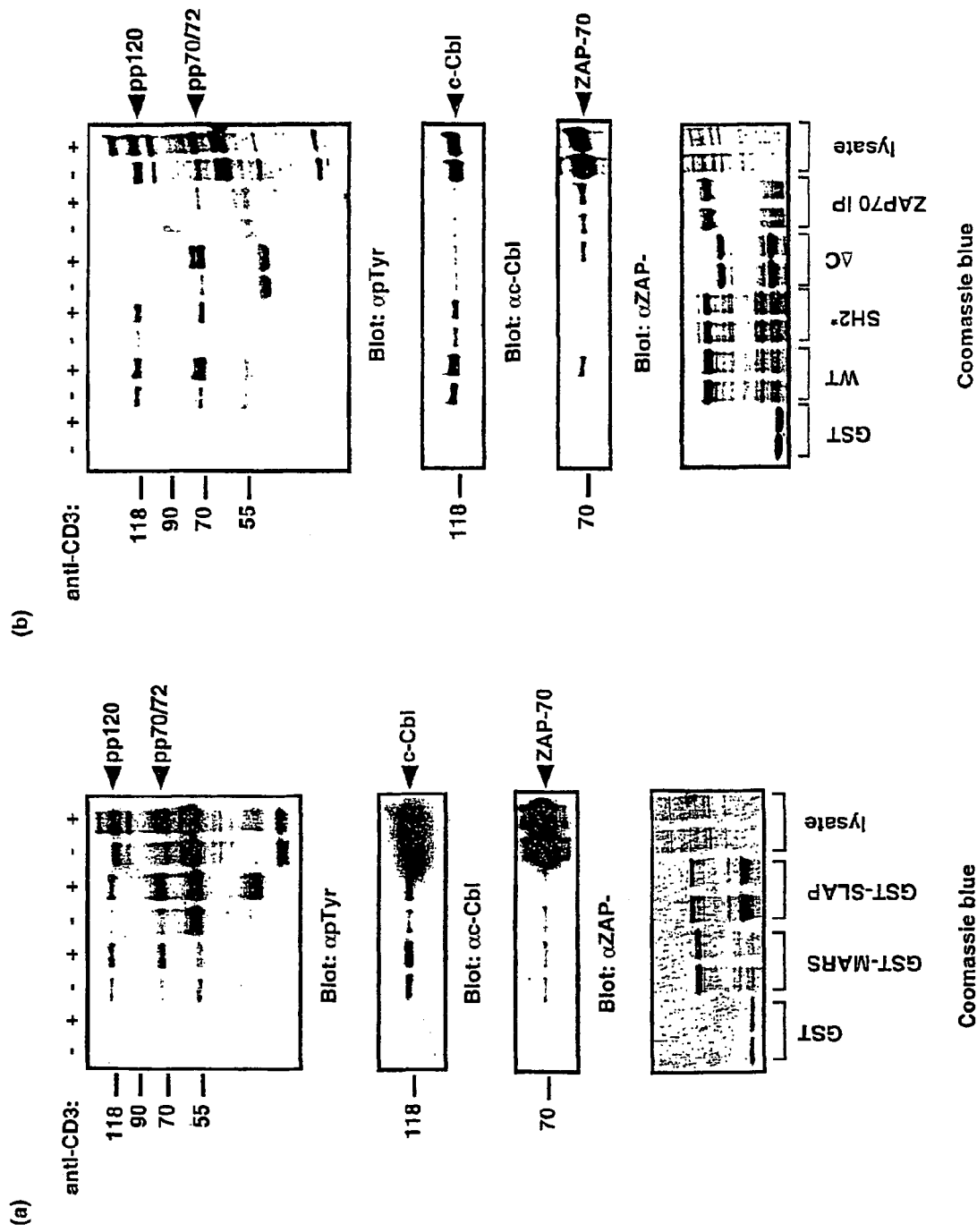
FIG. 5 shows immunoblots illustrating that MARS associates in vitro with tyrosine phosphorylated ZAP-70 and c-Cbl following TCR activation in Jurkat cells. (a) MARS and SLAP associate with a similar subset of T-cell phosphoproteins following TCR activation. MARS and SLAP GST fusion proteins were incubated with Jurkat cell lysates that were left unstimulated (−) or stimulated with antiCD3 antibody (+). Immunoblots were performed with the indicated antibodies. Membranes were stained with Coomassie blue dye to check relative expression levels of the fusions. (b) Mapping of the MARS interaction with Zap-70 and c-Cbl. Purified immobilized GST fusion proteins of wild type MARS or mutant MARS fusions with an inactivating mutation in the SH2 domain (SH2*) or a deletion of the carboxy terminus (AC) were incubated with Jurkat cell lysates that were left unstimulated (−) or stimulated with anti-CD3 antibody (+). Immunoblots were performed with the indicated antibodies. GST fusions were quantitated by staining the membrane with Coomassie blue dye.

Given the domain composition of MARS including the presence of an SH2 domain, and its endogenous expression in T-cells, its ability to interact with tyrosine-phosphorylated signaling proteins downstream of the activated TCR was investigated. Following stimulation of mouse primary thymocytes with anti-CD3 alone or costimulation with anti-CD3 and anti-CD28, anti-MARS-C antibody specifically immunoprecipitated tyrosine-phosphorylated proteins of approximately 70 and 120 kDa (FIG. 4). Subsequent immunoblotting identified the 120 kDa protein as c-Cbl. The interaction between MARS and c-Cbl was also observed in unstimulated cells. ZAP-70 has been reported to associate with c-Cbl, therefore the p72 phosphoprotein was tested to determine whether it represented ZAP-70 or the related family member. SYK. While unable to identify the co-precipitating 72 kDa phosphoprotein from primary thymocytes, experiments performed in Jurkat cells (FIG. 5) suggest that a similar set of bands migrating in the 70-72 kDa region contain ZAP-70. This suggests that the faint phosphotyrosine reactive bands migrating in the 70-72 kDa region in MARS immunoprecipitates may represent a very low level of activated ZAP-70 or SYK, or may in fact represent distinct proteins.

Recombinant GST-MARS interacted with a set of tyrosine phosphorylated proteins from anti-CD3 stimulated Jurkat cells similar to those observed binding to endogenous MARS in primary thymocytes (FIG. 5A). Furthermore, when the profile of T-cell phosphoproteins bound by GST-MARS and GST-SLAP were compared, both proteins interacted predominantly with phosphoproteins of approximately 70/72 KDa and 120 KDa, which were subsequently identified as ZAP-70 and c-Cbl, respectively (FIG. 5A). The interaction between MARS and c-Cbl was constitutive, but was increased following anti-CD3 stimulation. The observed interaction between SLAP and c-Cbl is in agreement with a previous report that identified SLAP as a c-Cbl interacting protein in a yeast-two-hybrid screen (39). Surprisingly, this interaction was not observed in two different studies of SLAP function in T-cells (34, 39).

To determine the regions of MARS required for interaction with c-Cbl and ZAP-70, GST-MARS fusion proteins containing mutations that disrupt the SH2 domain (SH2*), or that delete the carboxy-terminus of MARS (AC) were generated. The MARS mutants were tested for their ability to complex with tyrosine phosphorylated proteins from anti-CD3 stimulated Jurkat T-cells (FIG. 5B, top panel). Inactivation of the MARS SH2 domain specifically disrupted binding to the 70/72 kDa proteins, indicating that the interaction of MARS with these proteins is mediated by the SF12 domain. Notably, deletion of the MARS carboxy-terminus enhanced p72 binding or possibly its phosphorylation. Immunoblotting of the GST-MARS bound proteins with anti-ZAP-70 revealed that ZAP-70 is present in these complexes and corresponds to the lower (~70 kDa) band of the doublet (bottom panel). Although binding to ZAP-70 by the MARS SH2 mutant is significantly decreased, it is not completely abolished. This suggests that either MARS and ZAP-70 make additional contacts or perhaps that ZAP-70 is recruited indirectly through binding to c-Cbl. Reprobing of the membrane with anti-c-Cbl antibodies revealed that the carboxy-terminus of MARS contains the primary c-Cbl binding region (middle panel). The SH2 domain mutant appeared to bind slightly less c-Cbl, while c-Cbl did not bind to the C-terminal deletion mutant of MARS (FIG. 5B). Since ZAP-70 still bound the MARS AC mutant, and cCbl binding was only weakly affected by the SH2 mutation, these proteins likely bind MARS independently.

MARS Inhibits TCR-Mediated NFAT Activation

Figure 6:
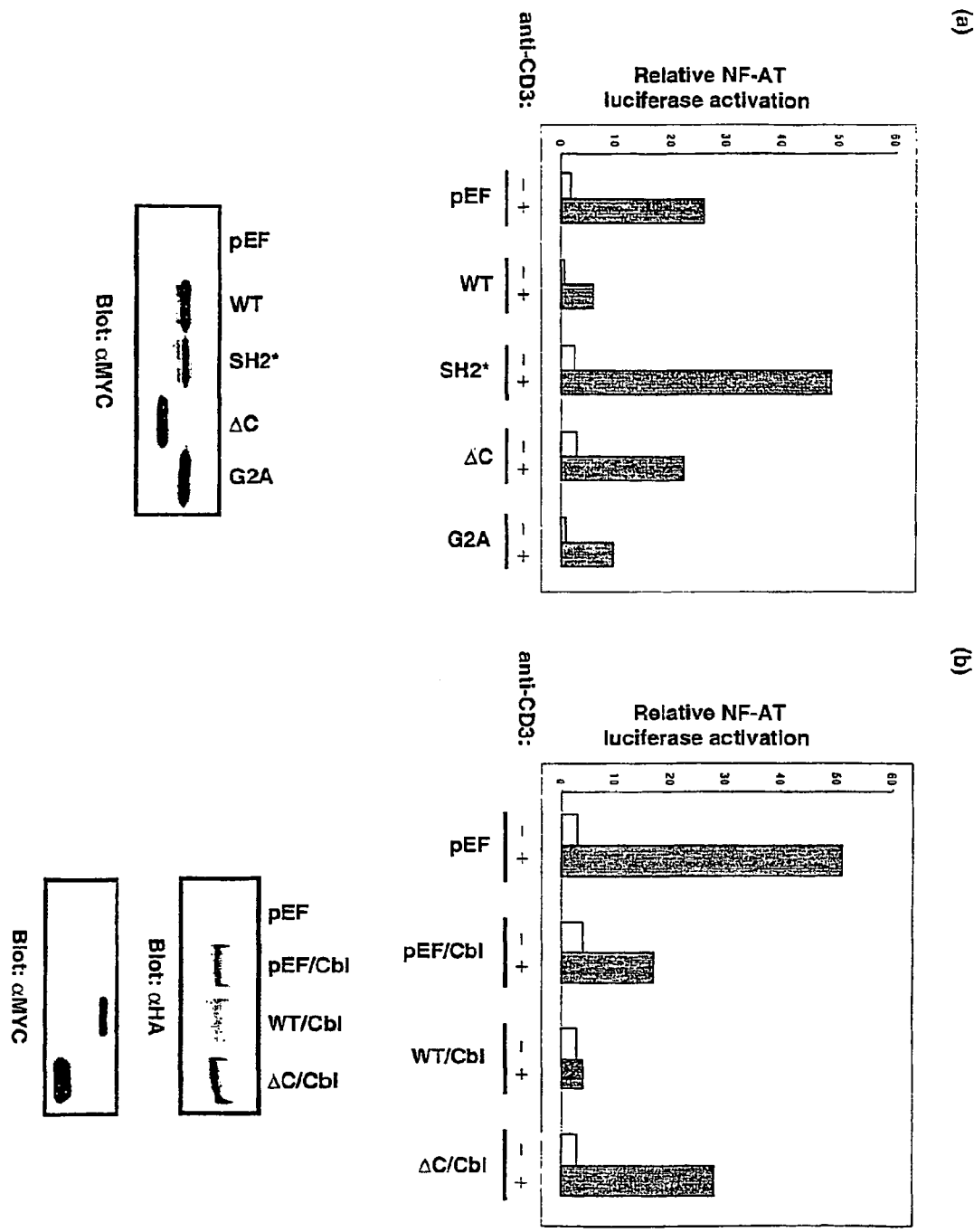
FIG. 6 shows immunoblots illustrating MARS is a negative regulator of signaling from the TCR.

Activation of the TCR triggers an intracellular signaling cascade that leads to the activation of specific nuclear transcription factors and subsequent transcriptional upregulation and expression of IL-2. NFAT is one of the transcription factors that is activated in response to TCR activation. To determine the effect of MARS on TCR signaling, NFAT activation was measured in the presence of over-expressed MARS or the MARS mutant proteins (G2A, SH2* and AC) described above, with a reporter gene consisting of the NFAT responsive IL-2 promoter fused to the luciferase cDNA. The transient over-expression of the wild-type MARS protein in Jurkat T-cells blocked the anti-CD3 triggered activation of NFAT (FIG. 6A). Both the myristoylation mutant (G2A) and AC mutant MARS proteins had intermediate inhibitory effects compared to the wild-type protein, indicating both c-Cbl binding and membrane localization are important for MARS function. In contrast, the SH2 mutant dramatically enhanced NFAT activation, suggesting that this mutant acts as a dominant negative blocking the inhibitory activity of endogenous MARS.

Over-expression of c-Cbl has also been shown to inhibit NFAT activation downstream of the activated TCR (26). Therefore, it was investigated whether MARS could influence c-Cbl-mediated down regulation of TCR signaling. As previously reported, expression of c-Cbl resulted in a significant decrease in NFAT activation in response to CD3 stimulation (FIG. 6B). Co-transfection of c-Cbl with wild-type MARS further enhanced this effect, completely blocking TCR-mediated NFAT activation. Conversely, the MARS AC mutant, which does not interact with c-Cbl, did not enhance c-Cbl inhibitory activity, and in fact appeared to partially rescue NFAT activation.

MARS Downregulates ZAP-70 and CD3E Expression Levels.

Figure 7:
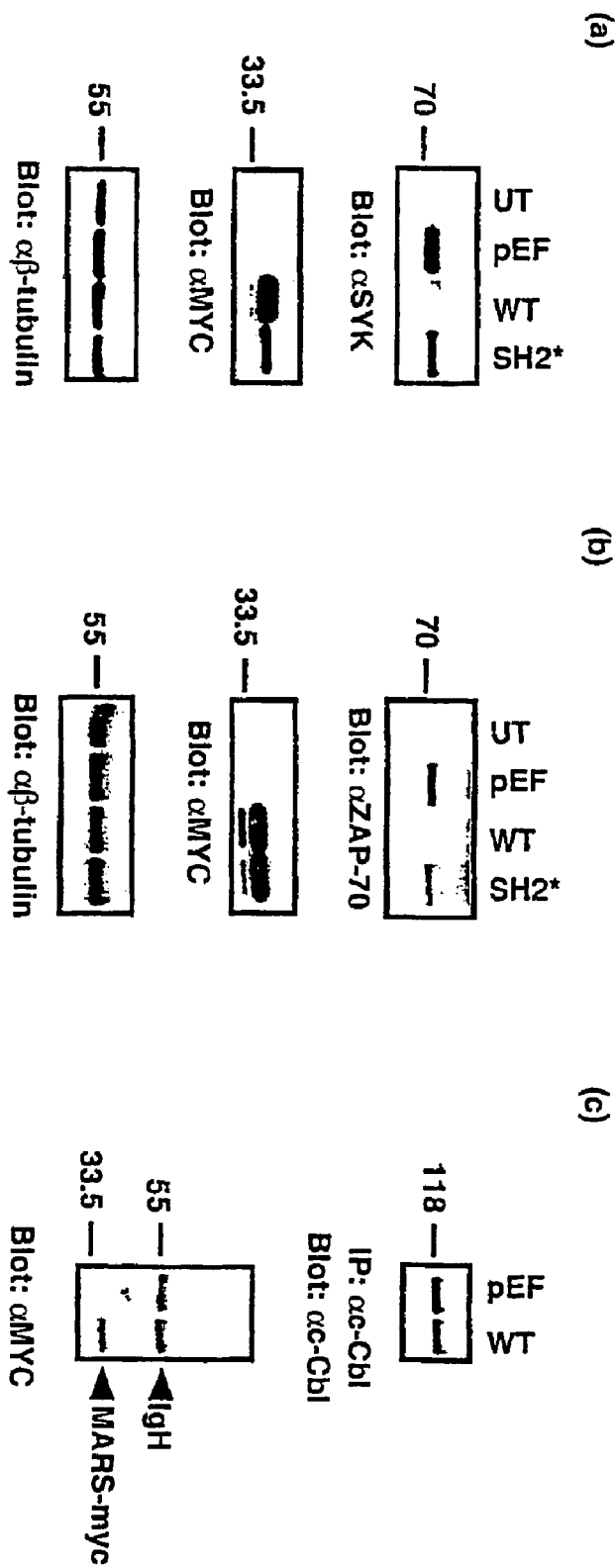
FIG. 7 shows immunoblots illustrating MARS expression promotes degradation of c-Cbl substrates SYK and ZAP-70. Mammalian expression constructs for (A) SYK or (B) ZAP-70 were cotransfected into COS7 cells with either empty vector or expression constructs encoding myc-tagged wild-type (WT) and SH2 mutant (SH2*) MARS proteins. Lysates from transfected cells were subjected to SDSPAGE and immunoblotted with either anti-SYK or anti-ZAP-70 antibodies (top panel), anti-myc (middle panel), and anti-13-tubulin (bottom panel). (C) Transfected MARS protein binds to endogenous c-Cbl in COS cells. Lysate from COS7 cells transfected with myc-tagged wild-type MARS was immunoprecipitated with anti-c-Cbl antibody. Membranes were immunoblotted with anti-c-Cbl (top panel) and anti-myc (bottom panel) antibodies.
Figure 8:
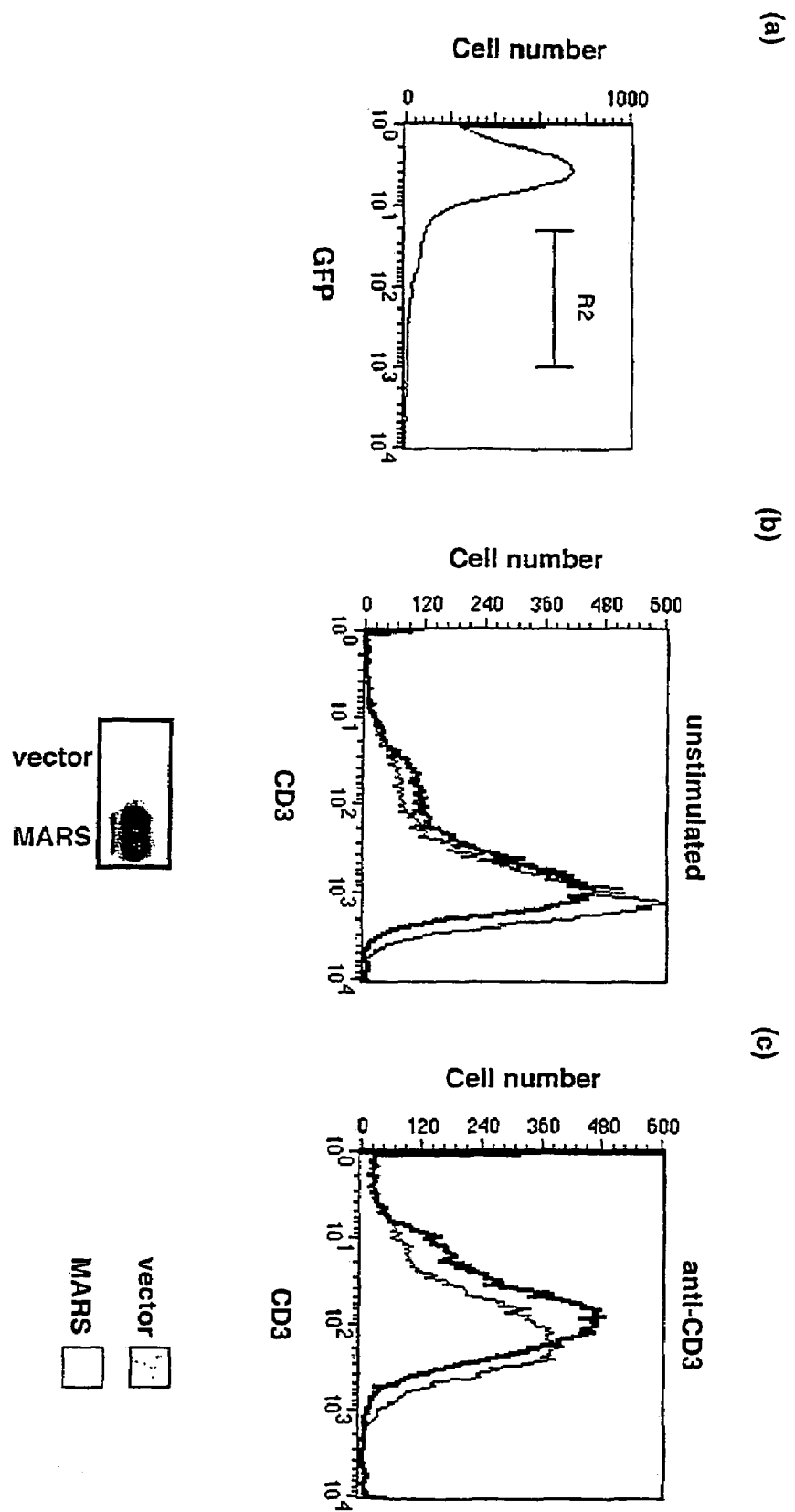
FIG. 8 shows MARS expression causes reduced surface expression of CD3 in Jurkat T-cells. Jurkat T cells were transiently transfected with either empty-IRES-GFP vector (shaded peak) or MARS-ires-GFP (no shading). After 16 hours cells were left either (a) unstimulated or (b) stimulated with anti-CD3 for 1 hr. Cells were stained with a PE-labeled anti-CD3 and analyzed by flow cytometry. Histograms for GFP positive cells (R2 gated) were created using CellQuest™ software. Representative data from one of five independent experiments is shown. Expression of murine MARS in transiently transfected Jurkat cells was confirmed by immunoprecipitation and Western blot analysis with affinity purified anti-MARS-C antibody.

The mechanism by which c-Cbl carries out its inhibitory function in T cells relies on its ability to associate with the negative regulatory Y292 site in ZAP-70 (26). c-Cbl expression inhibits activation and tyrosine phosphorylation of ZAP-70 and the related family member SYK, and in some cell types, c-Cbl reduces SYK and ZAP-70 protein levels (24, 26, 28). Similar to the effect of c-Cbl over-expression, it was found that co-transfection of MARS with either SYK or ZAP-70 caused a dramatic reduction in the levels of both proteins (FIG. 7A, B). This effect was specific to MARS, since equivalent expression of a MARS(SH2*) mutant, which does not bind efficiently to ZAP-70 and does not inhibit NFAT activation, also did not reduce the levels of SYK and ZAP-70 proteins. It was confirmed in this experiment that transfected MARS was bound to endogenous c-Cbl, as well as the related Cbl-b protein, suggesting that the effect of MARS on SYK and ZAP-70 is likely mediated through c-Cbl or Cbl-b (FIG. 7C and data not shown). The effect of MARS with proteasome inhibitors was not blocked (data not shown). This finding is consistent with MARS activity being mediated through c-Cbl since down-regulation of activated receptor tyrosine kinases by c-Cbl seems to be predominantly through lysosomal rather than proteasomal degradation.

c-Cbl promotes the down-regulation of activated transmembrane receptor tyrosine kinases by promoting their ubiquitination (31, 32, 40). It is currently unknown whether c-Cbl regulates the trafficking of the activated TCR in addition to its role as a regulator of ZAP-70. However, c-Cbl deficient thymocytes have increased levels of surface CD3, CD4 and CD69 suggesting that c-Cbl may also have an effect on receptor levels in T cells (25, 30). Since MARS inhibitory activity appeared to be closely linked with its association with c-Cbl, it was investigated whether MARS expression affected surface CD3 levels on Jurkat T cells. Transient expression of wild-type MARS consistently resulted in a 25-30% reduction in CD3e levels, as assessed by mean fluorescence, when compared with empty vector control transfected cells (FIG. 8). MARS expression caused a reduction in surface CD3 c levels in both unstimulated and stimulated Jurkat cells although the effect was more pronounced following TCR activation. These results suggest that MARS and c-Cbl could be part of a complex that regulates internalization and trafficking of the TCR-CD3 complex.

The cloning and characterisation of murine MARS, as a SF13 and SH2 domain-containing adaptor protein which, exhibits sequence and structural similarity to SLAP and to members of the Src family of tyrosine kinases. Two protein isoforms of MARS, p28 and p25, are products of alternative translation initiation and, are expressed in hematopoietic tissues and cell lines. MARS functions as an inhibitor of T cell receptor-mediated signaling and MARS activity is directly correlated with its binding to c-Cbl, a protein with E3 ubiquitin ligase activity. In keeping with this inhibitory function of MARS, it was determined that it promotes both degradation of ZAP-70 and SYK tyrosine kinases and down regulation of cell surface CD3E.

The present results demonstrate that a functional MARS SF12 domain, the MARS C-terminus, and the membrane association of MARS are all required for the full inhibitory effects of the MARS protein. The present results are both similar and contradictory to those reported for the related protein SLAP. SLAP over-expression in Jurkat T-cells was similarly shown to inhibit TCR-mediated NFAT, AP-1 and IL-2 promoter activity, although, only the SLAP SH2 and SF13 domains were found to be necessary, and the carboxy-terminus of SLAP was not required for SLAP's inhibitory activity (34). In fibroblasts, SLAP has also been shown to associate with the activated PDGFR via its SF12 domain and to negatively regulate PDGFR-mediated DNA synthesis. In this context, both the SLAP SH2 domain and C-terminal regions were important for SLAP's inhibitory effects (41).

MARS and SLAP share both sequence and structural similarity, except in the carboxy terminal region where the amino acid sequences of these two proteins diverge. Despite the low sequence similarity, the carboxy terminal region of both proteins mediates the interaction with cCbl. It has been demonstrated that the interaction between MARS or SLAP with c-Cbl is constitutive in T cells and, therefore is likely to be independent of the tyrosine phosphorylation status of c-Cbl. The precise nature of the MARS-Cbl interaction remains to be elucidated. SLAP interaction with c-Cbl has previously been characterized in vitro, and involves a phosphotyrosine independent interaction of the c-Cbl amino-terminal region, containing a four-helix bundle, EF hand and variant SF12 domain, with a hydrophobic sequence present in the carboxy-terminus of SLAP (39).

It has been demonstrated that tyrosine phosphorylated ZAP-70 binds to MARS through the MARS SH2 domain. The similarity that exists between the SH3/SH2 protein interaction modules in MARS and SLAP suggests that these proteins might associate with a similar set of proteins. Indeed, SLAP also associates with both the SYK and ZAP-70 tyrosine kinases through its SH2 domain (34, 39). While inactivation of the MARS SH2 domain does not completely ablate the interaction between MARS and ZAP-70, it greatly diminishes the association between these two proteins. As c-Cbl has also been shown to bind to Y292 on ZAP-70 via its TKB domain (23), the low amounts of ZAP-70 observed to associate with the MARS SH2 mutant might be indirectly recruited via c-Cbl. Alternatively, the partial binding of ZAP-70 might also involve the SH3 domain of MARS. In addition to the interaction with ZAP-70 an inducible association between MARS and an unidentified protein, p72, appears to be mediated exclusively by the MARS SH2 domain.

Over-expression of the wild-type MARS protein in Jurkat T-cells results in a marked reduction in the activation of NFAT following TCR activation. The AC mutant and, to a lesser degree, the myristoylation site mutant (G2A) of MARS, are impaired in their ability to inhibit NFAT activation, indicating that both the membrane localization of MARS, as well as its association with c-Cbl via its C-terminus, are required for the protein to be able to exert its full inhibitory effect. Interestingly, a mutant form of the MARS protein possessing an inactivating point mutation in the SH2 domain (SH2*) appears to act as a dominant negative, inhibiting endogenous MARS function, and enhancing NFAT activation. The MARS SH2 mutant fails to interact with the unidentified 72 kDa phosphoprotein, and is severely compromised in its ability to bind ZAP-70, but still binds to c-Cbl, suggesting that this mutant may engage c-Cbl in an inactive complex uncoupled from ZAP-70 and p72. The expression of MARS with c-Cbl can further decrease NFAT activation. This additive effect is dependent upon the presence of an intact c-Cbl binding region suggesting that MARS and c-Cbl act in the same complex.

The identification of c-Cbl as an E3 ubiquitin ligase has provided further insight into the mechanisms that control down-regulation of receptor-mediated signaling. c-Cbl has been implicated in the direct ubiquitination of activated growth factor receptors such as EGFR, CSF1R, and PDGFR (32, 33, 40, 42, 43) regulating both internalization as well as trafficking from the recycling compartment to multi-vesicular bodies (MVB5), the gateway to lysosomal destruction (44). c-Cbl is known to negatively regulate signaling from the TCR and recent evidence has led to speculation that the mechanism underlying this activity may be due in part to a ubiquitin dependent alterations in TCR trafficking. Recently, it has been shown that c-Cbl mediates ubiquitination of TCR-zeta via its interaction with ZAP-70 (29). Furthermore, c-Cbl deficient thymocytes have been reported to have upregulated CD3, CD4 and CD69 suggesting that c-Cbl may also have an inhibitory effect on receptor levels in T cells. The TCR:CD3 is constitutively internalized and recycled back to the cell surface (45, 46). However, following TCR activation, a decrease in cell surface CD3 expression accompanies the down-regulation of signaling from the TCR:CD3 complex. It has been proposed that following activation, the internalized activated receptor complex is sorted to the lysosomal pathway for degradation rather than recycling back to the cell surface (46). Together this evidence strongly suggests that c-Cbl regulates TCR down-regulation in a manner analogous to that reported for activated receptor tyrosine kinases. Interestingly, thymocytes from SLAP deficient mice were reported to have elevated levels of surface TCR (37). Similarly, it is now determined that over-expression of MARS decreases cell surface CD3c expression in Jurkat T-cells.

A number of adaptor proteins have been shown to bind to c-Cbl. Many of these, including CrkL, Grb2, Nck, and CAP associate through either SH2 or SH3 mediated interactions with the c-Cbl carboxy terminus. Since this region of c-Cbl is not required for its ability to down regulate activated receptor or cytoplasmic tyrosine kinases these interactions may be important for distinct aspects of c-Cbl function (47, 48). It is proposed that MARS and SLAP represent a distinct class of c-Cbl associated adaptors, which appear to function in co-operation with c-Cbl, enhancing its ability to negatively regulate receptor mediated signaling. This class may also include APS, which has been shown to facilitate c-Cbl mediated down regulation of the both the PDGF and Insulin receptors.

These adaptors may facilitate c-Cbl function via a number of mechanisms. In T cells, MARS may direct the localization of c-Cbl to the activated TCR complex or to specific membrane compartments such as lipid rafts or endocytic vesicles. Targetting of c-Cbl to specific subcellular locations could in turn regulate substrate selection. The p28 form of MARS is anchored to cell membranes by myristoylation. In transiently transfected Hela cells both plasma membrane and perinuclear staining in vesicular structures was observed resembling recycling endosomes. SLAP has also been localized to the perinuclear region and colocalized with an endosomal marker. Whether MARS or SLAP influence the membrane compartmentalization of c-Cbl remains unknown. In contrast to p28 MARS, it is demonstrated that p25 MARS, which lacks the N-terminal myristoylation sequence, is cytosolic. Interestingly, the relative expression levels of p25 and p28 MARS translation isoforms is variable. While the p28 isoform is consistently expressed at a higher level in cell lines, the expression of the p25 isoform is greater than p28 in the thymus. The consequences of fluctuations in the relative levels of expression of these two isoforms remain unknown, however, p25 MARS may target c-Cbl to a different subcellular location, or antagonize the function of p28.

In addition to a potential role in localizing c-Cbl to the activated TCR and in close proximity to its substrates, MARS could alternatively participate in substrate recognition by the formation of a ternary complex involving c-Cbl and a substrate molecule. Through its SH2 domain, c-Cbl associates with and down regulates the SYK family tyrosine kinases, SYK and ZAP-70. It is demonstrated that MARS is capable of associating independently with both ZAP-70 and c-Cbl following TCR stimulation. Subsequently, it is determined that MARS functions analogously to c-Cbl, causing the specific degradation of both ZAP-70 and SYK. The formation of a stabilized complex involving MARS, c-Cbl and ZAP-70 thus may promote the ubiquitination of ZAP-70 as well as components of the TCR, such as TCR-α internalized activated receptor complex is sorted to the lysosomal pathway for degradation rather than recycling back to the cell surface (46). Together this evidence strongly suggests that c-Cbl regulates TCR down-regulation in a manner analogous to that reported for activated receptor tyrosine kinases. Interestingly, thymocytes from SLAP deficient mice were reported to have elevated levels of surface TCR (37). Similarly, it is demonstrated that over-expression of MARS decreases cell surface CD3c expression in Jurkat T-cells.

A number of adaptor proteins have been shown to bind to c-Cbl. Many of these, including CrkL, Grb2, Nck, and CAP associate through either SH2 or SH3 mediated interactions with the c-Cbl carboxy terminus. Since this region of c-Cbl is not required for its ability to down regulate activated receptor or cytoplasmic tyrosine kinases these interactions may be important for distinct aspects of c-Cbl function (47, 48). It is proposed that MARS and SLAP represent a distinct class of c-Cbl associated adaptors, which appear to function in co-operation with c-Cbl, enhancing its ability to negatively regulate receptor mediated signaling. This class may also include APS, which has been shown to facilitate c-Cbl mediated down regulation of the both the PDGF and Insulin receptors.

These adaptors may facilitate c-Cbl function via a number of mechanisms. In T cells, MARS may direct the localization of c-Cbl to the activated TCR complex or to specific membrane compartments such as lipid rafts or endocytic vesicles. Targetting of c-Cbl to specific subcellular locations could in turn regulate substrate selection. The p28 form of MARS is anchored to cell membranes by myristoylation. In transiently transfected Hela cells both plasma membrane and perinuclear staining was observed in vesicular structures resembling recycling endosomes. SLAP has also been localized to the perinuclear region and colocalized with an endosomal marker. Whether MARS or SLAP influence the membrane compartmentalization of c-Cbl remains unknown. In contrast to p28 MARS, it is demonstrated that p25 MARS, which lacks the N-terminal myristoylation sequence, is cytosolic. Interestingly, the relative expression levels of p25 and p28 MARS translation isoforms is variable. While the p28 isoform is consistently expressed at a higher level in cell lines, the expression of the p25 isoform is greater than p28 in the thymus. The consequences of fluctuations in the relative levels of expression of these two isoforms remain unknown, however, p25 MARS could target c-Cbl to a different subcellular location, or antagonize the function of p28.

In addition to a potential role in localizing c-Cbl to the activated TCR and in close proximity to its substrates, MARS could alternatively participate in substrate recognition by the formation of a ternary complex involving c-Cbl and a substrate molecule. Through its SH2 domain, c-Cbl associates with and down regulates the SYK family tyrosine kinases, SYK and ZAP-70. It is demonstrated that MARS is capable of associating independently with both ZAP-70 and c-Cbl following TCR stimulation. Subsequently, it is now demonstrated that MARS functions analogously to c-Cbl, causing the specific degradation of both ZAP-70 and SYK. The formation of a stabilized complex involving MARS, c-Cbl and ZAP-70 thus may promote the ubiquitination of ZAP-70 as well as components of the TCR, such as TCR-α.

B. Human MARS

Concurrent with the cloning of the murine cDNA, the human MARS homologue was isolated and characterized. Employing the NCBI's BLAST algorithm, the murine MARS cDNA sequence was used to search human high throughput genomic DNA sequences (htgs) on the Genbank sequence database. Several overlapping genomic clones contained regions of the MARS coding sequence (FIG. 9B); Accession No. AL050318 (exons 3-7), AL031662 (exons 1 and 2), AC026539 (exons 2-4)). The full-length coding region of the human MARS cDNA was subsequently cloned from human thymus cDNA with gene-specific PCR primers. The 783 base pair cDNA encodes a putative protein of 261 amino acids, two amino acids longer than the murine counterpart (FIG. 9A). Using both the mouse and human cDNA sequences as a guide, the genomic structure of the coding region of the human MARS gene was deduced and the exon/intron boundaries determined from the various human genomic clones. The coding region of the human MARS gene consists of 7 exons and 6 introns, with all exon/intron splice sites conforming to the eukaryotic GTIAG splice rule (Mount 1982). Exons 2 and 3 encode the SH3 domain, while exons 4 and 5 encode the SH2 domain (FIG. 9B). The intra-SH2 intron located between exons 4 and 5 is very large (~17 Kb), and the 7 exons span approximately 28 Kb. This genomic structure is similar to that for murine and human SLAP (Kratchmarova et al., 2001) suggesting a common ancestry of these two closely related genes.

Figure 10:
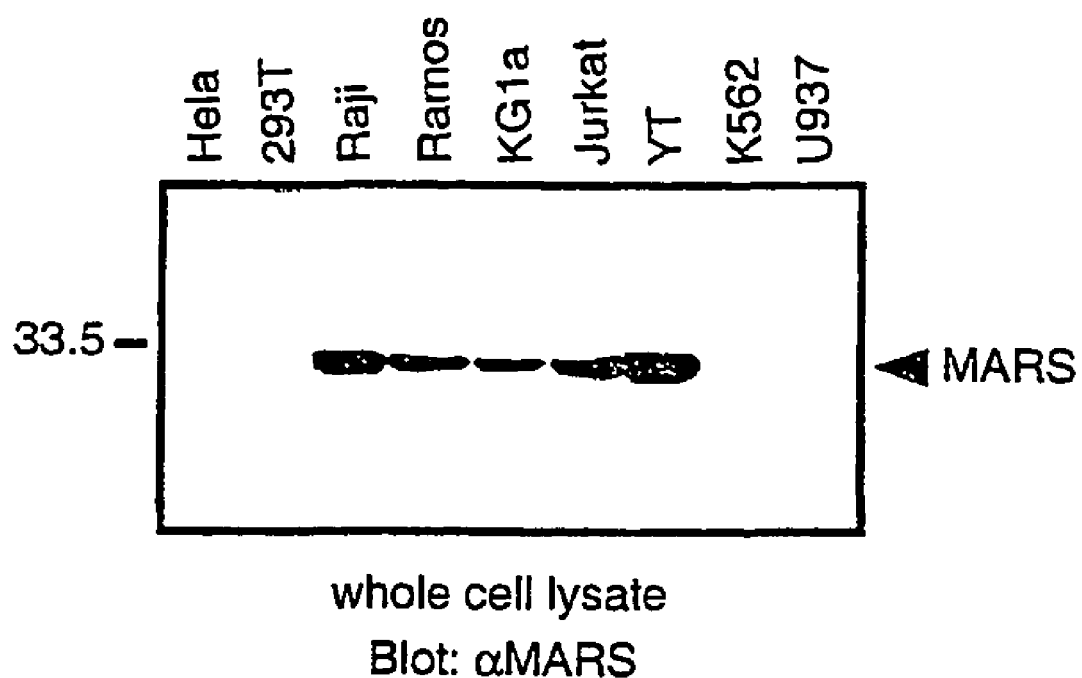
FIG. 10 shows a western blot illustrating expression of MARS protein in human cell lines.

To study human MARS protein expression, immunoblots were performed on protein extracts from a number of human hematopoietic and non-hematopoietic cell lines using the MARS-specific antibody generated against the C-terminus of murine MARS (FIG. 10). Consistent with the expression profile of the murine protein, human MARS protein was observed predominantly in hemotopoietic cells. MARS protein was detected in the B-cell lines Raji and Ramos, the Jurkat T-cell line and the natural killer cell line, Yt. Additionally, human MARS protein expresssion was observed in the myeloid cell line, KG1a, indicating that MARS is expressed in hematopoietic cells of both myeloid and lymphoid lineages. Subsequently, MARS protein expresssion has been observed in other myeloid cell lines (OCI, AML-2, 3 and 5), further supporting this conclusion (data not shown). Human MARS protein expression was not observed in either of the two non-hematopoietic cell lines studied, Hela and 293T.

Figure 11:
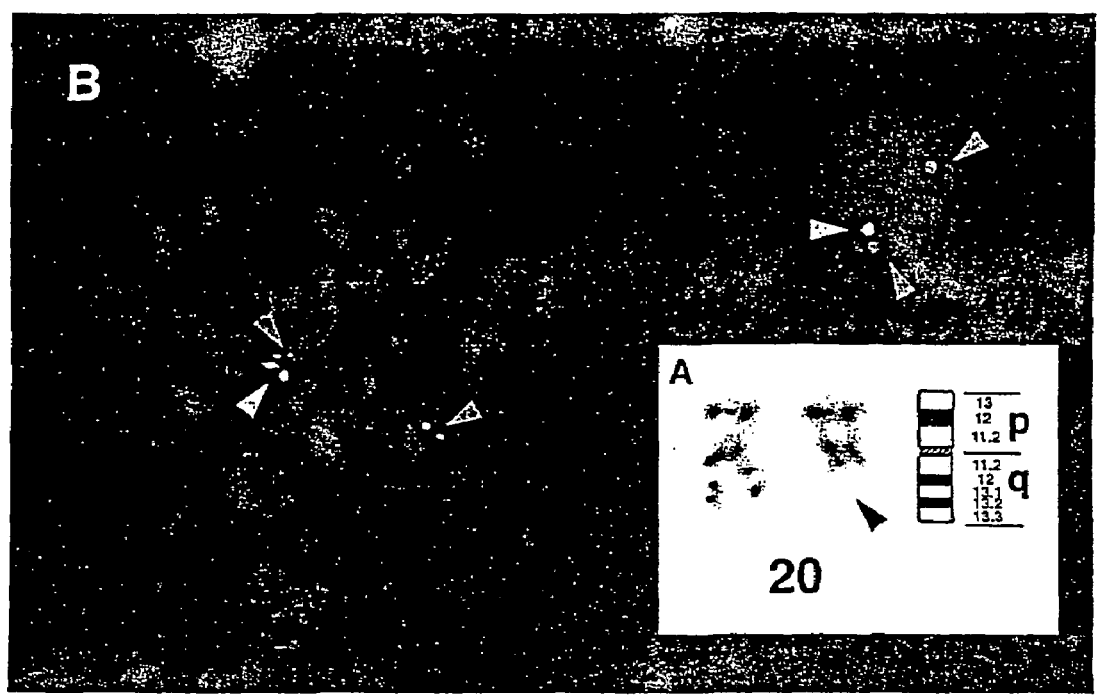
FIG. 11A shows a G-banded chromosome 20 composite of a patient with a deletion at 20q11.
FIG. 11B shows fluorescence in situ hybridization of metaphase chromosomes from patient in FIG. 11A with a 20q11 deletion probed with MARS.

One of the genomic clones used to determine the structure of the MARS gene was annotated as mapping to chromosome 20q11.21-23. A search of the NCBI's Cancer Genome Aberration Project (CGAP) database for recurrent chromosomal abnormalities in human malignancies, indicated that this region of chromosome 20 is frequently deleted in myeloproliferative disorders. It has been hypothesized that one or perhaps several genes exhibiting tumour suppressor activity may be localized in the vicinity of 20q11 contributing to the etiology of a group of premalignant hyperproliferative disorders of the myeloid cell population (Roulston et al., 1993). The chromosomal localization of MARS was confirmed by fluorescence in situ hybridization (FISH) with the MARS genomic clone harbouring exons 3 through 7 (AL050318) as a gene-specific probe. Fixed cells from a cohort of patients with monoallelic deletions of 20q11 were assessed for the presence of MARS. In this analysis, a significant proportion of these patients were found to have deletions of the MARS gene (FIG. 11, and data not shown). In a survey of human cell lines, MARS protein expression was not observed in either the K562 or U937 myeloid leukemia cell lines. This is of particular interest given that both of these cell lines have been described cytogenetically as having deletions of chromosome 20 q (Mac Grogan et zal., 2001).

Figure 12:
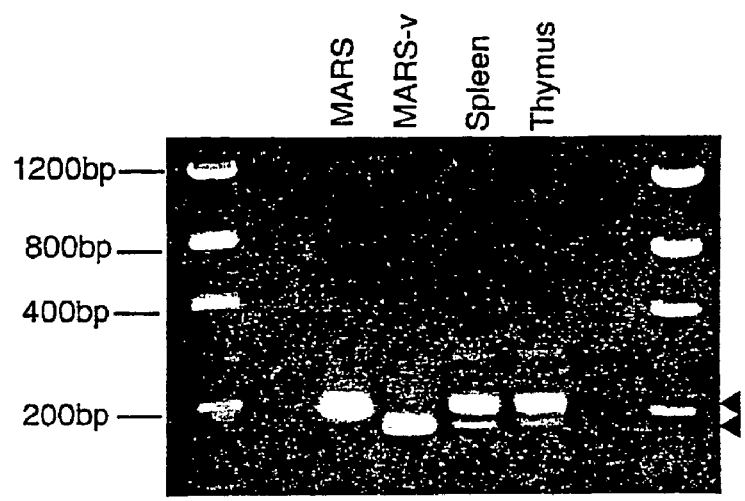
FIG. 12A shows an amino acid alignment of the predicted unique carboxy terminal regions of the human MARS and MARS-v proteins. Conserved amino acid residues are indicated by capital letters while similar residues are denoted by '+'.
FIG. 12B shows a schematic representation of the alternative splice acceptor in exon 6 which gives rise to the MARS-v transcript.
FIG. 12C shows intron-exon table illustrating the internal splice acceptor site in exon 6.
FIG. 12D shows the PCR detection of MARS-v transcript expression in human spleen and thymus.

In addition to the expected full-length human MARS cDNA, PCR-based cloning from human thymus cDNA also yielded a shorter MARS cDNA (FIG. 12). Based on the deduced genomic structure of the human MARS gene, it was apparent that the shorter cDNA represented a MARS isoform derived from alternative splicing. This alternative form of MARS is designated herein as "MARS-v" (MARS-variant). In the variant, exon 5 (which completes the SH2 domain), is spliced to exon 6 at an internal splice acceptor site (FIG. 12B, C). This alternative splicing removes 50 base pairs of exon 6, and results in the introduction of an alternative reading frame, and translation termination early in exon 7. This unique cDNA, therefore, has a predicted open-reading frame that would encode a protein of 210 amino acids, with a unique carboxy-terminal amino acid sequence (FIG. 12A, B). Expression of the alternatively spliced isoform has been confirmed by RT-PCR from a number of RNA sources (FIG. 12D and data not shown). The MARS antibody used to establish the expression profile of both the murine and human MARS protein was generated against a GST fusion of the murine MARS carboxy terminus, and therefore, would not be capable of detecting the protein encoded by the splice variant.

Figure 13:
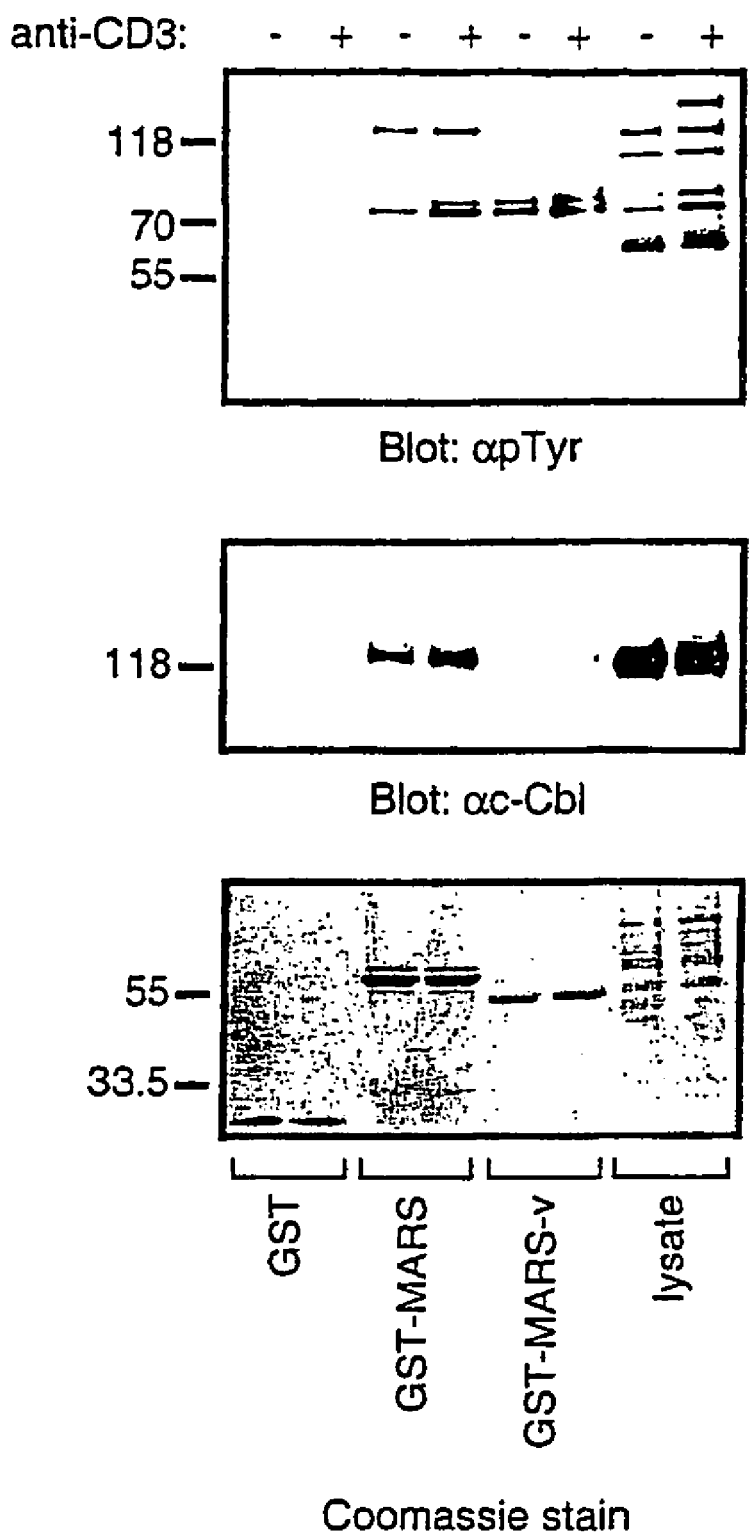
FIG. 13 shows western blots illustrating MARS and MARS-v non-binding to c-Cbl in T-cells.

The inhibitory effect of MARS on signaling downstream of the activated TCR is dependent upon an interaction with c-Cbl via its C-terminal region. In order to assess the ability of the MARS splice variant to interact with c-Cbl, MARS and MARS-v were expressed as GST fusion proteins and in vitro binding experiments were conducted (FIG. 13). The results demonstrated that the MARS-v protein does not interact with c-Cbl in vitro.

To summarize, a murine MARS adaptor gene has been cloned and characterized. The murine MARS adaptor protein is involved in c-Cbl mediated negative regulation of T-cell receptor signaling. MARS promotes the degradation of the SYK and ZAP-70 tyrosine kinases and decreases levels of CD3ϵ at the cell surface. These results indicate that MARS functions in concert with c-Cbl to down-regulate signaling and promote lysosomal targeting and degradation of activated receptor complexes. The related protein SLAP, likely functions in a similar mechanism.

Further, the human MARS gene has been cloned and characterized and a splice variant for the human homologue of the MARS protein, has been characterized and identified as MARS-v. The functional characterization of MARS as a negative regulator of mitogenic signaling in T-cells, coupled with its expression in myeloid lineage cells and its localization to a region of the human genome that is commonly deleted in myeloproliferative disorders, indicates that the loss of MARS (i.e. a loss or decrease in MARS activity) may be associated with the etiology of such diseases. Further, the alternative splice variant does not appear to interact wth c-Cbl, further highlighting the complexity of the MARS' role in cell signaling.

The identification and characterization of the MARS gene and product function provides various different uses of these molecules.

In one embodiment, MARS protein and peptides may be used for diagnosis of neoplastic conditions on the basis of the alteration of normal (wild-type) MARS polypeptide. Such alterations can be determined by sequence analysis in accordance with conventional techniques. More preferably, antibodies (polyclonal or monoclonal) are used to detect differences in or the absence of MARS peptides. In a preferred embodiment of the invention, antibodies may immunoprecipitate MARS proteins from a sample as well as react with MARS protein on immunoblots of polyacrylamide gels. In another preferred embodiment, antibodies may detect MARS proteins in paraffin or frozen tissue sections, using immunocytochemical techniques. Techniques for raising and purifying antibodies are well known in the art, and are described supra.

Methods for detecting MARS or a mutation thereof or variant may also include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530.

In a further embodiment of the invention, the invention is particularly useful for screening compounds by using the MARS polypeptide or binding fragment thereof in any of a variety of drug screening techniques, such as those described herein and in published PCT application WO 97/02048. The MARS polypeptide or fragment employed in such a test may either be free in solution or affixed to a solid support. One method of drug screening utilizes eukaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a MARS polypeptide or fragment and the agent being tested, or examine the degree to which the formation of a complex between a MARS polypeptide or fragment and a known ligand is aided or interfered with by the agent being tested. Functional protein-protein interaction assays are within the scope of the invention.

Thus, the present invention provides methods of screening for drugs comprising contacting such an agent with a MARS polypeptide or fragment thereof and assaying (i) for the presence of a complex between the agent and the MARS polypeptide or fragment, or (ii) for the presence of a complex between the MARS polypeptide or fragment and a ligand, by methods well known in the art. In such competitive binding assays the MARS polypeptide or fragment is typically labeled. Free MARS polypeptide or fragment is separated from that present in a protein:protein complex, and the amount of free (i.e., uncomplexed) label is a measure of the binding of the agent being tested to MARS or its interference with or promotion of MARS:ligand binding, respectively. One may also measure the amount of bound, rather than free, MARS. It is also possible to label the ligand rather than the MARS and to measure the amount of ligand binding to MARS in the presence and in the absence of the drug being tested. Another technique for drug screening provides high throughput screening for compounds having suitable binding affinity to the MARS polypeptides and is described in detail in published PCT application WO 84/03564.

Purified MARS can be coated directly onto plates for use in the aforementioned drug screening techniques. However, non-neutralizing antibodies to the polypeptide can be used to capture antibodies to immobilize the MARS polypeptide on the solid phase.

The invention also contemplates the use of competitive drug screening assays in which neutralizing antibodies capable of specifically binding the MARS polypeptide compete with a test compound for binding to the MARS polypeptide or fragments thereof. In this manner, the antibodies can be used to detect the presence of any peptide which shares one or more antigenic determinants of the MARS polypeptide.

The above screening methods are not limited to assays employing only MARS but are also applicable to studying MARS-protein complexes. The effect of drugs on the activity of such complexes, especially when either the MARS protein or other protein contains a mutation, is analyzed.

In accordance with these methods, several representative assays are can be used for screening for drug candidates. For example, a mutant MARS (per se or as part of a fusion protein) is mixed with a wild-type protein (per se or as part of a fusion protein) to which wild-type MARS binds. This mixing is performed in both the presence of a drug and the absence of the drug, and the amount of binding of the mutant MARS with the wild-type protein is measured, If the amount of the binding is more in the presence of said drug than in the absence of said drug, the drug is a candidate for treating cancer resulting from a mutation in MARS. In a further example, a mutant protein, which acts as a wild-type protein binds to MARS (per se or as part of a fusion protein) is mixed with a wild-type MARS (per se or as part of a fusion protein). This mixing is performed in both the presence of a drug and the absence of the drug, and the amount of binding of the mutant protein with the wild-type MARS is measured. If the amount of the binding is more in the presence of said drug than in the absence of said drug, the drug is a drug candidate for treating cancer resulting from a mutation in the gene encoding the protein.

The polypeptide and fragments thereof of the invention may also be used for screening compounds developed as a result of combinatorial library technology. Combinatorial library technology provides a way of testing a potential vast number of different substances for ability to modulate activity of a polypeptide. Such libraries and their use are known in the art, see for example, WO 97/02048.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et al., 1993). This system may be used as a coarse screen prior to testing a substance for actual ability to modulate activity of the polypeptide. Alternatively, the screen could be used to screen test substances for binding to a MARS specific binding partner, or to find mimetics of the MARS polypeptide.

Once a substance which modulates or affects polypeptide activity is identified, the substance may be investigated further. Furthermore, it may be manufactured and/or used in preparation, i.e., manufacture or formulation, or a composition such as a medicament, pharmaceutical composition or drug. These may be administered to individuals.

In further embodiments of the present invention, are pharmaceutical compositions, medicaments, drugs or other compositions comprising a MARS nucleic acid or protein/polypeptide, a method comprising administration of such a composition comprising such a MARS nucleic acid, protein or peptide, a method comprising administration of such a composition to a patient, e.g., for treatment (which may include preventative treatment) of cancer, use of such a substance in the manufacture of a composition for administration, e.g., for treatment of cancer, and a method of making a pharmaceutical composition comprising admixing such a substance with a pharmaceutically acceptable excipient, vehicle or carrier, and optionally other ingredients.

A substance identified using as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process. In a variation of this approach, the three-dimensional structure of the ligand and its binding partner are modeled. This can be especially useful where the ligand and/or binding partner change conformation on binding, allowing the model to take account of this in the design of the mimetic. A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

In a further embodiment of the invention is rational drug design to produce structural analogs of biologically active polypeptides of interest or of small molecules with which they interact (e.g., agonists, antagonists, inhibitors or enhancers) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., MARS) or, for example, of a MARS-substrate or MARS-ligand complex, by x-ray crystallography, by computer modeling or most typically, by a combination of approaches. Less often, useful information regarding the structure of a polypeptide may be gained by modeling based on the structure of homologous proteins. In addition, peptides (e.g., MARS) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide. It is also possible to isolate a target-specific antibody, selected by a functional assay, and then to solve its crystal structure.

Drugs may be designed which have, e.g., improved MARS activity or stability or which act as enhancers, inhibitors, agonists, antagonists, etc. of MARS activity. By virtue of the availability of cloned MARS sequences, sufficient amounts of the MARS polypeptide may be made available to perform such analytical studies as x-ray crystallography. In addition, the knowledge of the MARS protein sequence provided herein will guide those employing computer modeling techniques in place of, or in addition to x-ray crystallography.

In yet a further embodiment of the invention, a method is also provided of supplying wild-type MARS function to a cell which carries a mutant MARS allele. Supplying such a function should suppress neoplastic growth of the recipient cells. The wild-type MARS gene or a part of the gene may be introduced into the cell in a vector such that the gene remains extra-chromosomal. In such a situation, the gene will be expressed by the cell from the extra-chromosomal location. If a gene portion is introduced and expressed in a cell carrying a mutant MARS allele, the gene portion should encode a part of the MARS protein which is required for regulation of cell proliferation. More preferred is the situation where the wild-type MARS gene or a part thereof is introduced into the mutant cell in such a way that it recombines with the endogenous mutant MARS gene present in the cell. Such recombination requires a double recombination event which results in the correction of the MARS gene mutation. Vectors for introduction of genes both for recombination and for extra-chromosomal maintenance are known in the art, and any suitable vector may be used. Methods for introducing DNA into cells such as electroporation, calcium phosphate co-precipitation and viral transduction are known in the art, and the choice of method is within the competence of the practitioner. Cells transformed with the wild-type MARS gene can be used as model systems to study cancer remission and drug treatments which promote such remission.

As generally discussed above, the MARS gene or fragment, where applicable, may be employed in gene therapy methods in order to increase the amount of the expression products of such genes in cancer cells. Such gene therapy is particularly appropriate for use in both cancerous and pre-cancerous cells, in which the level of MARS polypeptide is absent or diminished compared to normal cells. It may also be useful to increase the level of expression of a given MARS gene even in those tumor cells in which the mutant gene is expressed at a "normal" level, but the gene product is not fully functional.

Gene therapy would be carried out according to generally accepted methods, for example, as described by Friedman (1991) or Culver (1996). Cells from a patient's tumor would be first analyzed by the diagnostic methods described above, to ascertain the production of MARS polypeptide in the tumor cells. A virus or plasmid vector, containing a copy of the MARS gene linked to expression control elements is prepared. The vector may be capable of replicating inside the tumor cells. Suitable vectors are known, such as disclosed in U.S. Pat. No. 5,252,479, PCT published application WO 93/07282 and U.S. Pat. No. 5,691,198. The vector is then injected into the patient, either locally at the site of the tumor or systemically (in order to reach any tumor cells that may have metastasized to other sites). If the transfected gene is not permanently incorporated into the genome of each of the targeted tumor cells, the treatment may have to be repeated periodically.

Gene transfer systems known in the art may be useful in the practice of the gene therapy methods of the present invention. These include viral and nonviral transfer methods. A number of viruses have been used as gene transfer vectors or as the basis for preparing gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990; Schneider et al., 1998), vaccinia virus (Moss, 1992; Moss, 1996), adeno-associated virus (Muzyczka, 1992; Ohi et al., 1990; Russell and Hirata, 1998), herpesviruses including HSV and EBV (Margolskee, 1992; Johnson et al., 1992; Fink et al., 1992; Breakefield and Geller, 1987; Freese et al., 1990; Fink et al., 1996), lentiviruses (Naldini et al., 1996), Sindbis and Semliki Forest virus (Berglund et al., 1993), and retroviruses of avian (Bandyopadhyay and Temin, 1984; Petropoulos et al., 1992; murine (Miller, 1992; Miller et al., 1985; Sorge et al., 1984; Mann and Baltimore, 1985; Miller et al., 1988), and human (Shimada et al., 1991; Helseth et al., 1990; Page et al., 1990; Buchschacher and Panganiban, 1992) origin. Most human gene therapy protocols have been based on disabled murine retroviruses, although adenovirus and adeno-associated virus are also being used.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinsier et al., 1981; Costantini and Lacy, 1981); membrane fusion-mediated transfer via liposomes (Feigner et al., 1987; Wang and Huang, 1989; Kaneda et al, 1989; Stewart et al., 1992; Nabel et al., 1990; Lim et al., 1991); and direct DNA uptake and receptor-mediated DNA transfer (Wolff et al., 1990; Wu et al., 1991; Zenke et al., 1990; Wu et al., 1989; Wolff et al., 1991; Wagner et al., 1990; Wagner et al., 1991; Cotten et al., 1990; Curiel et al., 1991; Curiel et al., 1992). Viral-mediated gene transfer can be combined with direct in vivo gene transfer using liposome delivery, allowing one to direct the viral vectors to the tumor cells and not into the surrounding nondividing cells. Alternatively, a retroviral vector producer cell line can be injected into tumors (Culver et al., 1992). Injection of producer cells would then provide a continuous source of vector particles.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors, see Schneider et al. (1998) and U.S. Pat. No. 5,691,198.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes MARS, expression will produce MARS. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

Gene transfer techniques which target DNA directly to hematopoeitic tissue and cells is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function. Patients who carry a MARS susceptibility allele are treated with a gene delivery vehicle such that some or all of their precursor cells receive at least one additional copy of a functional normal MARS allele. In this step, the treated individuals have reduced risk of cancer to the extent that the effect of the susceptible allele has been countered by the presence of the normal allele.

In a further embodiment of the invention, peptides which have MARS activity can be supplied to cells which carry mutant or missing MARS alleles. The sequence of the MARS protein is disclosed (SEQ ID NO:2, SEQ ID NO:4). Protein can be produced by expression of the cDNA sequence in bacteria, for example, using known expression vectors. Alternatively, MARS polypeptide can be extracted from MARS-producing mammalian cells. In addition, the techniques of synthetic chemistry can be employed to synthesize MARS protein or peptides. Any of such techniques can provide the preparation of the present invention which comprises the MARS protein. The preparation is substantially free of other human proteins. This is most readily accomplished by recombinant expression in a microorganism or by chemical synthesis. Once substantially purified protein or peptide is provided it is understood by one of skill in the art that any further suitable stabilizer may be added thereto as desired for a particular use.

Active MARS molecules can be introduced into cells by microinjection or by use of liposomes, for example. Alternatively, some active molecules may be taken up by cells, actively or by diffusion. Extracellular application of the MARS gene product may be sufficient to affect tumor growth. Supply of molecules with MARS activity should lead to partial reversal of the neoplastic state. Other molecules with MARS activity (for example, peptides, drugs or organic compounds) may also be used to effect such a reversal. Modified polypeptides having substantially similar function are also useful for peptide therapy.

In a further embodiment of the invention are model systems to study and test for substances which have potential as therapeutic agents. The cells are typically cultured cells isolated from individuals with MARS mutations. Alternatively, the cell line can be engineered to carry the mutation in the MARS allele, as described above. Any cell line that carry a MARS allele is suitable. After a test substance is applied to the cells, the neoplastically transformed phenotype of the cell is determined. Any trait of neoplastically transformed cells can be assessed, including proliferation, anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant MARS alleles, usually from a second animal species, as well as insertion of disrupted homologous genes. Alternatively, the endogenous MARS gene of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). After test substances have been administered to the animals, the growth of cancerous cells and tumors may be assessed. If the test substance prevents or suppresses the growth of tumors, then the test substance is a candidate therapeutic agent for the treatment of the cancers identified herein. Animal models provide an extremely important testing vehicle for potential therapeutic products.

The identification of the association between the MARS gene deletion and mutations and lymphoproliferative cancer permits the early presymptomatic screening of individuals to identify those at risk for developing cancer. To identify such individuals, MARS alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucleotide sequence of both the cloned alleles and normal MARS gene or appropriate fragment (coding sequence or genomic sequence) are determined and then compared, or (2) the RNA transcripts of the MARS gene or gene fragment are hybridized to single stranded whole genomic DNA from an individual to be tested, and the resulting heteroduplex is treated with ribonuclease A (RNase A) and run on a denaturing gel to detect the location of any mismatches. Alternatively, polymerase chain reactions (PCRs) are performed with primer pairs for the 5' region or the exons of the MARS gene. PCRs can also be performed with primer pairs based on any sequence of the normal MARS gene. For example, primer pairs for one of the introns can be prepared and utilized. Finally, RT-PCR can also be performed on the mRNA. The amplified products are then analyzed by single stranded conformation polymorphisms (SSCP) using conventional techniques to identify any differences and these are then sequenced and compared to the normal gene sequence. Individuals can be quickly screened for common MARS gene variants by amplifying the individual's DNA using suitable primer pairs and analyzing the amplified product, e.g., by dot-blot hybridization using allele-specific oligonucleotide probes.

Any differences which are found, will identify an individual as having a molecular variant of the MARS gene and the consequent enhanced risk of or presence of cancer. Genetic testing will enable practitioners to identify individuals at risk for cancer at, or even before, birth.

In yet a further embodiment of the invention, MARS polypeptides, antibodies, peptides and nucleic acids of the present invention can be formulated in pharmaceutical compositions, which are prepared according to conventional pharmaceutical compounding techniques. See, for example, Remington's Pharmaceutical Sciences, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral. For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example; preservatives, suspending agents, solubilizing agents, buffers and the like. When the compounds are being administered intrathecally, they may also be dissolved in cerebrospinal fluid.

The active agent is preferably administered in an therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Remington's Pharmaceutical Sciences.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Methods of synthetic chemistry, protein and peptide biochemistry, molecular biology, histology and immunology referred to but not explicitly described in this disclosure and examples are reported in the scientific literature and are well known to those skilled in the art.

Example 1

Cloning of Murine MARS cDNA

An in silico screen of high throughput genomic sequence (htgs) on the Genbank sequence database was conducted in an attempt to identify novel SH2 domain-containing proteins. Using the amino acid sequence of the GADS SH2 domain and the NCBI's tBLASTn search algorithm, a large genomic clone containing the partial sequence of a novel SH2 domain-containing protein bearing weak homology to GADS was identified (Accession #AL050318). Subsequently, the human genomic clone was used with the BLASTn search algorithm to search the mouse expressed sequence tag (EST) database, leading to the identification of two overlapping EST's encoding the 5' end of a novel murine cDNA. Nested primers were designed in the 5' untranslated region (UTR) of the cDNA sequence and used to do 3' rapid amplification of cDNA ends (RACE) on Marathon Ready mouse Day 15 embryo (Clontech). A single RACE product of 1348 bp (SEQ ID NO:1) was amplified using the PCR primers: 5'cacgctctttgtccctgctgt-gctg-3' (sense) (SEQ ID NO:8) and 5'-ggcccaatctggfttctct-gagaagc-3' (nested sense) (SEQ ID NO:9).

Cell Lines

COS1, COS7, Raw264.7, RBL-2H3, MEF, and NIH3T3 cells were cultured in Dulbecco's Modified Eagle Medium (DMEM) supplemented with 10% (v/v) fetal bovine serum (Gibco BRL), 200 mM L-glutamine, 5 U/ml penicillin C, and 5 mg/ml streptomycin sulfate. Jurkat E6.1, WEHI, DO11.10 and P815 cells were cultured in RPMI 1640 medium supplemented as above. BaF3 cells were maintained in RPMI 1640 supplemented as above with the addition of 10 ml WEHI cell supernatant (IL-3), while CTLL-2 cells were maintained in RPMI 1640 supplemented as above with the addition of recombinant IL-2 (2 U/ml Roche). Primary mouse thymocytes from a six-week old female mouse were cultured in RPMI 1640, supplemented as above.

Mammalian Expression Constructs and GST Fusion Proteins.

Wild-type and mutant MARS cDNAs were cloned in-frame into pcDNA3.1-myc/His (EcoRI/BamHI), pEF-myc/His (ClaI/XbaI), and pEGFP-IRES2 (EcoRI/BamHI) mammalian expression vectors. Both the pcDNA3.1 and pEF constructs possess C-terminal myc/His-epitope tags so as to avoid interfering with the N-terminal myristoylation of the MARS protein. Similarly, wild-type and mutant MARS cDNAs were cloned in-frame into pGEX-4T1 (EcoRI/XhoI) in order to produce GST fusion proteins in bacteria. All MARS mutants were generated by PCR-based mutagenesis; myristoylation mutant (G2A): glycine at amino acid position 2 mutated to alanine, methionine mutant #1 (M1V): methionine at amino acid position 1 mutated to valine, methionine mutant #2 (M27V): methionine at amino acid position 27 mutated to valine, SH2 inactivating mutant (SH2*): arginine residue at amino acid position 120 mutated to lysine, AC: contains a deletion of the carboxy-terminal 70 amino acids. All MARS expression constructs were confirmed by DNA sequencing.

Transient Transfections and NFAT-Luciferase Assays

COS 1, COS7 and Hela cells were grown to ~60% confluence in 10 cm tissue culture dishes and transfected with 24 μg of each expression vector using Lipofectin reagent (Gibco-BRL), according to the manufacturer's instructions. For NFAT luciferase assays, Jurkat E6.1 cells ($20 \times 10^6$) were electorporated (250V, 960° F.) with 20 μg 40 μg of empty vector, Cbl, or MARS expression constructs and 10 μg of NFAT-luciferase reporter construct. NFAT luciferase assays were conducted as previously described (7, 49).

In Vitro Binding Assays

GST fusion proteins were produced in bacteria and purified on glutathione-sepharose beads (Pharmacia). In vitro binding assays were done using Jurkat T-cell lysates ($20 \times 10^6$ cells) either unstimulated or stimulated with anti-CD3 antibody (anti-CD3s mAb, clone UCHT1, Pharmingen). Lysates were incubated with ~4 μg of GST fusion proteins for 90 min. at 4° C. Following several washes, bound proteins were eluted in 2×SDS sample buffer and resolved by SDS-PAGE. Membranes were stained with Coomassie blue dye to quantitate GST fusions.

Cell Stimulation

Jurkat E6.1 cells were stimulated with anti-CD3 antibody (mAb clone UCHT1, Pharmingen, 2 μg) for 2 minutes at 37° C. Mouse thymocytes ($5 \times 10^7$) were stimulated with anti-CD3E alone (mAb clone 145-2C11, Pharmingen, 10 jig), anti-CD28 alone (mAb clone 37.51, Pharmingen, 10 jig), or co-stimulated with anti-CD3 and anti-CD28 antibodies for either 2, 5, or 15 mins., in the presence of a rabbit anti-mouse secondary reagent. Following stimulation, Jurkat T-cells and mouse primary thymocytes were lysed in NP-40 lysis buffer containing complete protease inhibitors (Roche) and 1 mM sodium orthovanadate.

Antibodies

Polyclonal MARS antisera were produced by immunizing rabbits with a GST fusion protein containing the C-terminal domain of murine MARS. 5 μl of crude sera and pre-immune serum was used for immunoprecipitation, and crude serum was used at a 1:500 dilution for blotting, or 3 μl of affinity purified MARS antibody was used in immunoprecipitation experiments, and a 1:1000 dilution was used for immunoblotting. Affinity purified GADS antibody was used at a 1:1000 dilution for immunoblotting as previously described (38). Anti-myc 9E 10 monoclonal antibody was purchased from the Developmental Studies Hybridoma Bank (University of Iowa), and 2 μg was used for immunoprecipitation at a dilution of 1:1000 for immunoblotting. Monoclonal anti-ZAP-70 antibody was purchased from Transduction laboratories and used at a dilution of 1:1000 for immunoblotting. Rabbit polyclonal anti-SYK/ZAP-70 pan-antibody was a kind gift from Andre Veillette (McGill University, Montreal, Quebec). 5 μl was used in immunoprecipitation experiments, and a dilution of 1:500 was used for immunoblotting. Anti-phosphotyrosine (4G10) monoclonal antibody was purchased from UBI and used at a dilution of 1:1000 for immunoblotting. Rabbit anti-c-Cbl polyclonal antibody was purchased from Santa Cruz Biotechnology (Santa Cruz, Calif.). 10 µl of anti-cCbl antibody was used in immunoprecipitation experiments, and a 1:1000 dilution was used for immunoblotting. Anti-TCR-zeta antibody was purchased from Zymed and used at a 1:500 dilution for immunoblotting. Sheep anti-mouse antibody (1:6000 dilution) and protein-A (1:3000 dilution) conjugated to horseradish peroxidase (HRP), were used to detect bound primary mouse monoclonal and polyclonal antibodies, respectively.

Immunoprecipitation and Western Blotting

Cells and murine tissue samples were lysed in 1 ml of PLC lysis buffer (50 mM HEPES pH 7.5, 150 mM NaCl, 10% v/v glycerol, 1% v/v Triton X-100, 1.5 mM $MgCl_2$, 1 mM EDTA, 10 mM NaPPi, 100 mM NaF) or 1 ml of Nonidet-P40 (NP-40) lysis buffer (50 mM HEPES pH 7.5, 150 mM NaCl, 10% v/v glycerol, 1% v/v Nonidet P40, 0.1 mM $ZnCl_2$, 2 mM EDTA) containing complete protease inhibitors (Roche) and 1 mM sodium orthovanadate. Cell lysates were cleared by centrifigation at 14000 r.p.m. at 4° C. for 10 mins., and precleared by incubation with 50 µl of 20% v/v protein G-sepharose beads (Sigma, for immunoprecipitation with monoclonal antibodies) or with protein A-sepharose beads (Sigma) and 2 µg of rabbit anti-mouse IgG (for immunoprecipitations with polyclonal antibodies), at 4° C. for 30 mins. Precleared lysates were incubated with antibodies and either protein G- or protein A sepharose beads as described, and incubated at 4° C. with gentle rotation for 90 mins. or overnight. Immune complexes were washed four times in 1 ml cold 0.1% NP-40 lysis buffer, and bound proteins were eluted by boiling for 5 mins. in 2×SDS sample buffer. Eluted proteins were resolved by SDS-PAGE on 10% gels. Proteins were electrophoretically transferred to PVDF membrane (NEN Life Science), and incubated in a blocking solution of either 5% w/v skim milk powder in 1×TBST or in 1% BSA (w/v) in 1×TBST (anti-phosphotyrosine blotting) for a minimum of 30 mins. prior to the addition of antibody. Blocked membranes were incubated with primary antibodies at room temperature for 1 hr. or at 4° C. overnight. Membranes were incubated for 45 mins. with an appropriate secondary antibody conjugated to HRP. Bound antibody was detected using enhanced chemiluminescence reagent (NEN Life Science).

RNA Isolation from Murine Tissues and RT-PCR Analysis

Total RNA was isolated from the tissues of an 8-week-old mouse using 1 ml of Trizol reagent (Gibco BRL) per 100 mg of tissue as per the manufacturer's instructions. Total RNA samples were re-suspended in DEPC-water and stored at −80° C. 1 µg of total RNA was DNaseI treated and reverse transcribed into cDNA using SuperScript II reverse transcriptase (Gibco BRL). 1/10 of the resulting cDNA was subjected to 30 cycles of PCR amplification using murine MARS-specific primers: 5'-TGTACATCTCACCTCGCCT-CACC-3'(sense) (SEQ ID NO:10); 5'-TCAGCGGAGTT-GGAGCTCTCGG-3' (antisense) (SEQ ID NO:11), or murine 13-actin specific control primers: 5'-GTCGTACCA-CAGGCATTGTGATGG-3' (sense) (SEQ ID NO:12); 5' GCAATGCCTGGGTACATGGTGG-3' (antisense) (SEQ ID NO:13) The resulting PCR products were electrophoresed on 1.2% agarose gels stained with ethidium bromide, and visualized under UV light.

Subcellular Fractionation.

DO 11.10 cells ($2.5 \times 10^7$) were washed with 1×PBS and lysed in 1 ml of hypotonic lysis buffer (10 mM Tris-HCl pH 8.0, 1 mM $MgCl_2$) containing complete protease inhibitors and 1 mM sodium orthovanadate. Cells were sufficiently lysed upon vortexing as checked by tyrpan blue staining. Lysed cells were adjusted back to isotonic conditions by the addition of 5 M NaCl to a final concentration of 150 mM. Lysate was centrifuged at 3,000 r.p.m. for 10 mins. at 4° C. Pellet representing the nuclear fraction was resuspended in extraction buffer (1% SDS, 1% Triton-X100, 1% sodium deoxycholate) in TBS (10 mM Tris-HCl pH 8.0, 150 mM NaCl, 1 mM $MgCl_2$). Supernatant from the first spin was centrifuged in a Beckman tabletop ultracentrifuge using the TLA-45 rotor at 43,000 r.p.m ($100,000 \times g$) for 30 mins. at 4° C. Pellet representing the membrane fraction was resuspended in extraction buffer as described above. Supernatant representing the soluble/cytoplasmic fraction was adjusted to 0.1% SDS, 0.1% Triton-X-100, and 0.1% sodium deoxycholate. 250 µg of protein lysate was immunoprecipitated and immunoblotted with affinity purified anti-MARS antibody. To confirm the integrity of the individual fraction, 40 µg of lysates were resolved by SDS-PAGE and immunoblotted with both anti-GADS (soluble protein control) and anti-TCRzeta (membrane protein control) antibodies.

Immunofluorescence.

Hela cells were transiently transfected with myc-tagged wild-type MARS or G2A mutant MARS expression constructs as described. Transfected cells were seeded onto glass coverslips and washed 2 times with 1× phosphate buffered saline (PBS) plus Ca/Mg. Cells were fixed with 4% paraformaldehyde for 30 mins. at room temperature, and permeabilized with 0.2% Triton-X-100 in PBS for 10 mins. Permeabilized cells were incubated with primary anti-myc (9E10) monoclonal antibody (1:1000), and subsequently with Alexa488-labeled (green fluorescence) anti-mouse secondary antibody (1:500) at 37° C. for 30 mins. Cell nuclei were stained with propidium iodide (red fluorescence). Coverslips were mounted onto glass slides and visualized by confocal microscopy.

Flow Cytometry

Jurkat E6.1 cells were electroporated as previously described, with either empty pEGFP-IRES2 vector or pEGFP-IRES2 vector containing the wild-type MARS coding region. 24 hours after electroporation, cells were harvested and either left unstimulated or stimulated with anti-human CD3 antibody for 1 hr. at 37° C. $1 \times 10^6$ were subsequently stained with 2 µg of anti-human CD3E primary antibody, and 1 µg of phycoeiythrin (PE)-labeled anti-mouse IgG (Pharmingen). Stained cells were analyzed by flow cytometry with CellQuest software. CD3 expression was determined on cells that received the plasmids and expressed green fluorescent protein (GFP+). Dead cells were excluded from the analysis by staining with propidium iodide. Data from a representative experiment are shown. Expression of transfected MARS protein was confirmed by immunoprecipitation and western blotting using the affinity purified anti-MARS-C antibody.

Example Two

Cloning of Human MARS Sequence

Gene-specific PCR primers designed based on MARS exon sequences were used to amplify the full-length human MARS cDNA from human thymus cDNA (Clontech). Primers used for PCR were: 5'-atgggaagtctgcccagcagaag-3' (sense) (SEQ ID NQ:14) and 5'-ctaggcatcatccaaagagacagcc-3' (anti-sense) (SEQ ID NO:15). These sequence data have been submitted to Genbank and are available under the accession number AF290985. FIG. 9 shows a schematic representation of the genomic structure of the coding region of the human MARS gene. Screening of high-throughput genome sequence databases using the NCBI BLAST algorithm was used to identify genomic clones harboring fragments of the human MARS coding region. Exon-intron boundaries were determined by deduction from the cDNA sequences of mouse and human MARS. The numbering refers to coding exons (I-VII) and the numbers within the boxes denote the number of amino acids encoded by each of the exons. The number of base pairs for each of the respective introns is also indicated. (C) Intron-exon table highlighting the sequence context of the splice junctions of the human MARS gene and the adherence to the GT/AG rule for eukaryotic splicing.

Expression of MARS Protein in Human Cell Lines

Hela and 293T cells were cultured in Dulbecco's Modified Eagle Medium (DMEM) supplemented with 10% (v/v) fetal bovine serum (Gibco BRL), 200 mM L-glutamine, 5 U/ml penicillin C, and 5 mg/ml streptomycin sulfate. Raji, Ramos, Jurkat, YT, K562 and U937 cells were cultured in RPMI 1640 medium supplemented as above. KG1a cells were cultured in Iscove's Media supplemented with 20% (v/v) fetal bovine serum, 200 mM L-glutamine, 5 U/ml penicillin C, and 5 mg/ml streptomycin sulfate. Cells were lysed in 1 ml of PLC lysis buffer (50 mM HEPES pH 7.5, 150 mM NaCl, 10% v/v glycerol, 1% v/v Triton X-100, 1.5 mM MgCl, 1 mM EDTA, 10 mM NaPPi, 100 mM NaF, 1 mM Na3VO4) containing complete protease inhibitors (Roche). Cell lysates were quantified by Bradford Protein Assay, and 50 µg of protein lysate was diluted in 2×SDS sample buffere and denatured by boiling for 5 min. Denatured proteins were resolved by SDS-PAGE on 10% gels. Proteins were electrophoretically transferred to PVDF membrane, and incubated in a blocking solution of 5% w/v skim milk powder in TBST for 30 min. Blocked membranes were incubated with affinity purified rabbit anti-mouse MARS antibody as described (Loretto et al., submitted) at room temperature for 1 hr. Membranes were washed 3 times for 10 minutes with TBST at room temperature and incubated for 45 mins with Protein A-HRP conjugate. Following incubation with Protein A-HRP, membranes were washed 3 times for 10 minutes with TBST at room temperature and developed using ECL reagent (Amersham).

Localization of the MARS Gene to Chromosome 20q11

Chromosomes were fixed and G-banded using established protocols (FIG. 11A). An idiogram of chromosome 20 was presented. Fluorescence in situ hybridization (FISH) was done of the metaphase chromosomes from the same patient with a 20q11 deletion probed with MARS. A BAC clone of MARS containing exons 3 to 7 was labeled with Spectrum Green and a 20pter PAC (dj1061i1) CLONE (used as an internal control) was labeled with Spectrum Orange. The nick translation kit used for labeling was purchased from Vysis. Both probes were co-denatured on a previously G-banded slide and hybridized-overnight. The slides were washed and counterstained with DAPI using established protocols. The slides were analyzed on an epi-fluorescent microscope (Zeiss Axioscope 2) using image analysis software provided by Applied Imaging. The green arrows indicate the 20pter signal on the short arm of each chromosome 20 (FIG. 11B). The orange arrow indicates the MARS signal on the normal chromosome 20q; there is no MARS signal on the deleted chromosome 20.

Identification of a Human MARS Splice Isoform

The MARS-v cDNA was cloned during the PCR-based cloning of the full-length human MARS cDNA using the PCR primers indicated for FIG. 9. The nucleotide and amino acid sequences for MARS-v have been submitted to Genbank and are available under the accession number AF290986). FIG. 12 shows a schematic representation of the alternative splice acceptor in exon 6 which gives rise to the MARS-v transcript. The splice acceptor site was identified by comparing the coding sequence of the MARS-v cDNA with the MARS genomic sequence. For PCR detection of MARS-v transcript expression in human spleen and thymus, cDNA was subjected to 30 rounds of PCR using gene-specific primers hybridizing near the 3' end of the coding region of the human MARS cDNA and flanking the region of the transcript deleted by the alternative splicing. The PCR primers used were 5'-aggagaggctcttactctctgtcag-3' (sense) (SEQ ID NO:16) and 5'-ctaggcatcatccaaagagacagcc-3' (anti-sense) (SEQ ID NO:17). MARS-v Protein and c-Cbl Binding in T-cells Full-length MARS and MARS-v coding regions were fused in-frame to glutathione-S-transferase, in PGEX4T1. Recombinant GST fusion proteins were expressed in bacteria and purified on glutathione sepharose (GS) (Pharmacia). Jurkat T-cells (20×10⁶) were either left unstimulated (−) or stimulated with anti-CD3 (+); (anti-human CD3ε, clone UCGT1, Pharmingen) for 2 minutes. Cells were lysed in 1% NP-40 lysis buffer containing 1 mM sodium orthovanadate and complete protease inhibitors (Roche). Cell lysates were incubated with 4 µg of GS bound GST fusion proteins for 90 minutes at 4° C. and washed 4 times for 10 minutes with 0.1% NP-40 lysis buffer. Bound proteins were eluted by boiling in 2×SDS sample buffer and were resolved by SDS-PAGE on 10% polyacrylamide gels. Proteins were subsequently transferred to PVDF membrane (NEN) and blotted with anti-phosphotyrosine antibody (clone 4G10, UBI; top panel, FIG. 13). Membranes were stripped and reprobed with anti-c-Cbl antibody (Santa Cruz; middle panel, FIG. 13), and subsequently stained with Coomassie blue dye to check for equal loading of the respective fusions (bottom panel, FIG. 13).

Although preferred embodiments of the invention have been described herein in detail, it will be understood by those skilled in the art that variations may be made thereto without departing from the spirit of the invention or the scope of the appended claims.

TABLE 1

SEQ ID NO:1: Nucleotide sequence of the full-length mouse MARS cDNA. (1348 bp)

|  |  |  |  |  |  |
|---|---|---|---|---|---|
| 1 | GGCCCAATCT | GGTTTCTCTG | AGAAGCAAAG | GACTGCTGTA | CTAGTTTCGT |
| 51 | GGAGATTGTC | TGCTGACAAA | GAAGCTTGAT | CACAGTACCT | CAGCCTACTC |
| 101 | TGACTCCTTT | CTGGTGACCG | ATCCTCCAGG | CTGCTGGGGC | CTGAGATGCC |
| 151 | GACTACCTTA | GGACCTGCAA | AGGCCTGACC | TGTCGGGTCA | GTGTGCACAT |
| 201 | TGGCTGACTA | CCCTCATCAA | ACGTCTG | ATGGCAAACCTTT | CCCTTTCCAG |
| 251 | GTTCAGTGTG | CTTGTGAGCG | TCTGCTGAGT | GATGGGAAGT | TTGTCCAGCA |
| 301 | GAGGGAAAAC | CTCCAGCCCC | AGCCCCAGCT | CCTCTGGTCC | AGACCAGGAA |

TABLE 1-continued

SEQ ID NO:1: Nucleotide sequence of the full-length mouse MARS cDNA. (1348 bp)

```
 351 CCCGTGTCCA TGCAACCAGA AAGACACAAG GTCACAGCTG TGGCCCTGGG
 401 CAGTTTCCCA GCAGGTGAAC AGGCCAGACT ATCTCTGAGA CTCGGGGAGC
 451 CGCTGACCAT CATCTCTGAG GATGGAGATT GGTGGACAGT CCAGTCGGAA
 501 GTCTCAGGCA GAGAGTACCA CATGCCCAGT GTGTATGTGG CTAAAGTCGC
 551 CCACGGGTGG CTGTACGAGG GCCTGAGCCG GGAGAAAGCC GAGGAACTAC
 601 TCCTGTTACC TGGGAACCCC GGAGGGGCCT TCCTCATCCG GGAGAGCCAG
 651 ACCAGGAGAG GCTGCTATTC CCTGTCCGTC CGACTCAGCC GCCCTGCATC
 701 TTGGGACCGG ATCAGACACT ACAGGATACA GCGTCTTGAC AATGGCTGGC
 751 TGTACATCTC ACCTCGCCTC ACCTTCCCCT CACTCCACGC CTTGGTGGAG
 801 CATTACTCTG AGCTAGCAGA TGGCATCTGC TGTCCCCTCA GGGAGCCGTG
 851 TGTCCTGCAG AAGCTTGGGC CACTACCTGG CAAAGATACA CCTCCACCTG
 901 TGACTGTGCC AACATCATCA CTAAATTGGA AAAAGCTGGA CCGCAGCCTC
 951 CTGTTTCTGG AAGCACCTGC GAGTGGGGAG GCATCTCTGC TCAGTGAGGG
1001 GCTCCGAGAG TCCCTCAGTT CCTACATCAG CCTGGCTGAG GACCCCTTGG
1051 ATGATGCTTA GCCCTGGAAC ACAAAGAGAA AGGGAACCAA GACTGTGGCA
1101 CCGAGAGCTC CAACTCCGCT GACCCTGACA AGCTCCAGG AGGCAAGGCT
1151 GGGAGAACAG AGACGGCTGG GGTGGGGCAC AGACACTCGG GGCCTCACCT
1201 GGGCTTTCTG ATAAGTCATG TATCTCCTAA GGCCTCACCC CTACCTACTA
1251 CTTCTAGTCC ATGTGCAGTG CAGTTCAAAG CAGGGCTGGC CTCTACAGAG
1301 AATAAAATAC TTCTGAGGTC AAAAAAAAA AAAAAAAAA AAAAAAA
```

TABLE 2

SEQ ID NO:2: Nucleic acid sequence of mouse MARS coding region (777 bp)

```
ATGGGAAGT TTGTCCAGCA GAGGGAAAAC CTCCAGCCCC
AGCCCCAGCT CCTCTGGTCC AGACCAGGAA CCCGTGTCCA
TGCAACCAGA AAGACACAAG GTCACAGCTG TGGCCCTGGG
CAGTTTCCCA GCAGGTGAAC AGGCCAGACT ATCTCTGAGA
CTCGGGGAGC CGCTGACCAT CATCTCTGAG GATGGAGATT
GGTGGACAGT CCAGTCGGAA GTCTCAGGCA GAGAGTACCA
CATGCCCAGT GTGTATGTGG CTAAAGTCGC CCACGGGTGG
CTGTACGAGG GCCTGAGCCG GGAGAAAGCC GAGGAACTAC
TCCTGTTACC TGGGAACCCC GGAGGGGCCT TCCTCATCCG
GGAGAGCCAG ACCAGGAGAG GCTGCTATTC CCTGTCCGTC
CGACTCAGCC GCCCTGCATC TTGGGACCGG ATCAGACACT
ACAGGATACA GCGTCTTGAC AATGGCTGGC TGTACATCTC
ACCTCGCCTC ACCTTCCCCT CACTCCACGC CTTGGTGGAG
CATTACTCTG AGCTAGCAGA TGGCATCTGC TGTCCCCTCA
GGGAGCCGTG TGTCCTGCAG AAGCTTGGGC CACTACCTGG
CAAAGATACA CCTCCACCTG TGACTGTGCC AACATCATCA
CTAAATTGGA AAAAGCTGGA CCGCAGCCTC CTGTTTCTGG
AAGCACCTGC GAGTGGGGAG GCATCTCTGC TCAGTGAGGG
GCTCCGAGAG TCCCTCAGTT CCTACATCAG CCTGGCTGAG
GACCCCTTGG ATGATGCT
```

TABLE 3

SEQ ID NO:3: Amino acid sequence of the mouse MARS protein. (259 amino acids)

```
  1 MGSLSSRGKT SSPSPSSSGP DQEPVSMQPE RHKVTAVALG SFPAGEQARL
 51 SLRLGEPLTI ISEDGDWWTV QSEVSGREYH MPSVYVAKVA HGWLYEGLSR
101 EKAEELLLLP GNPGGAFLIR ESQTRRGCYS LSVRLSRPAS WDRIRHYRIQ
151 RLDNGWLYIS PRLTFPSLHA LVEHYSELAD GICCPLREPC VLQKLGPLPG
201 KDTPPPVTVP TSSLNWKKLD RSLLFLEAPA SGEASLLSEG LRESLSSYIS
251 LAEDPLDDA
```

TABLE 4

SEQ ID NO:4: Nucleotide sequence for the coding region of human MARS cDNA. (786 bp)

```
  1 ATGGGAAGTC TGCCCAGCAG AAGAAAATCT CTGCCAAGCC CAAGCTTGAG
 51 TTCCTCTGTC CAAGGCCAGG GACCTGTGAC CATGGAAGCA GAGAGAAGCA
101 AGGCCACAGC CGTGGCCCTG GGCAGTTTCC CGGCAGGTGG CCCGGCCGAG
151 CTGTCGCTGA GACTCGGGGA GCCATTGACC ATCGTCTCTG AGGATGGAGA
201 CTGGTGGACG GTGCTGTCTG AAGTCTCAGG CAGAGAGTAT AACATCCCCA
251 GCGTCCACGT GGCCAAAGTC TCCCATGGGT GGCTGTATGA GGGCCTGAGC
301 AGGGAGAAAG CAGAGGAACT GCTGTTGTTA CCTGGGAACC CTGGAGGGGC
351 CTTCCTCATC CGGGAGAGCC AGACCAGGAG AGGCTCTTAC TCTCTGTCAG
401 TCCGCCTCAG CCGCCCTGCA TCCTGGGACC GGATCAGACA CTACAGGATC
451 CACTGCCTTG ACAATGGCTG GCTGTACATC TCACCGCGCC TCACCTTCCC
501 CTCACTCCAG GCCCTGGTGG ACCATTACTC TGAGCTGGCG GATGACATCT
551 GCTGCCTACT CAAGGAGCCC TGTGTCCTGC AGAGGGCTGG CCCGCTCCCT
601 GGCAAGGATA TACCCCTACC TGTGACTGTG CAGAGGACAC CACTCAACTG
651 GAAAGAGCTG ACAGCTCCC TCCTGTTTTC TGAAGCTGCC ACAGGGGAGG
701 AGTCTCTTCT CAGTGAGGGT CTCCGGGAGT CCCTCAGCTT CTACATCAGC
751 CTGAATGACG AGGCTGTCTC TTTGGATGAT GCCTAG
```

TABLE 5

SEQ ID NO:5: Amino acid sequence of the human MARS protein. (261 amino acids)

```
  1 MGSLPSRRKS LPSPSLSSSV QGQGPVTMEA ERSKATAVAL GSFPAGGPAE
 51 LSLRLGEPLT IVSEDGDWWT VLSEVSGREY NIPSVHVAKV SHGWLYEGLS
101 REKAEELLLL PGNPGGAFLI RESQTRRGSY SLSVRLSRPA SWDRIRHYRI
151 HCLDNGWLYI SPRLTFPSLQ ALVDHYSELA DDICCLLKEP CVLQRAGPLP
201 GKDIPLPVTV QRTPLNWKEL DSSLLFSEAA TGEESLLSEG LRESLSFYIS
251 LNDEAVSLDD A
```

TABLE 6

SEQ ID NO:6: Nucleotide sequence for the coding
region (and partial 3-UTR of human MARS (short
isoform = putative splice variant; 737 bp)

```
  1 ATGGGAAGTC TGCCCAGCAG AAGAAAATCT CTGCCAAGCC CAAGCTTGAG
 51 TTCCTCTGTC CAAGGCCAGG GACCTGTGAC CATGGAAGCA GAGAGAAGCA
101 AGGCCACAGC CGTGGCCCTG GCAGTTTCC CGGCAGGTGG CCCGGCCGAG
151 CTGTCGCTGA GACTCGGGGA GCCATTGACC ATCGTCTCTG AGGATGGAGA
201 CTGGTGGACG GTGCTGTCTG AAGTCTCAGG CAGAGAGTAT AACATCCCCA
251 GCGTCCACGT GGCCAAAGTC TCCCATGGGT GGCTGTATGA GGGCCTGAGC
301 AGGGAGAAAG CAGAGGAACT GCTGTTGTTA CCTGGGAACC CTGGAGGGGC
351 CTTCCTCATC CGGGAGAGCC AGACCAGGAG AGGCTCTTAC TCTCTGTCAG
401 TCCGCCTCAG CCGCCCTGCA TCCTGGGACC GGATCAGACA CTACAGGATC
451 CACTGCCTTG ACAATGGCTG GCTGTACATC TCACCGCGCC TCACCTTCCC
501 CTCACTCCAG GCCCTGGTGG ACCATTACTC TGAGGGCTGG CCCGCTCCCT
551 GGCAAGGATA TACCCCTACC TGTGACTGTG CGGAGGACAC CACTCAACTG
601 GAAAGAGCTG GACAGCTCCC TCCTGTTTTC TGAAGCTGCC ACAGGGGAGG
651 AGTCTCTTCT CAGTGAGGGT CTCCGGGAGT CCCTCAGCTT CTACATCAGC
701 CTGAATGAGC GAGGCTGTCT CTTTGGATGA TGCCTAG
```

TABLE 7

SEQ ID NO:7: Amino acid sequence of the human
MARS protein, short isoform. (210 amino acids)

```
  1 MGSLPSRRKS LPSPSLSSSV QGQGPVTMEA ERSKATAVAL GSFPAGGPAE
 51 LSLRLGEPLT IVSEDGDWWT VLSEVSGREY NIPSVHVAKV SHGWLYEGLS
101 REKAEELLLL PGNPGGAFLI RESQTRRGSY SLSVRLSRPA SWDRIRHYRI
151 HCLDNGWLYI SPRLTFPSLQ ALVDHYSEGW PAPWQGYTPT CDCAEDTTQL
201 ERAGQLPPVF
```

TABLE 8

| Primer Sequences Mouse | |
|---|---|
| 5'-cacgctctttgtccctgctgtgctg-3' | SEQ ID NO:8 |
| 5'-ggcccaatctggtttctctgagaagc-3' | SEQ ID NO:9 |
| 5'-tgtacatctcacctcgcctcacc-3' | SEQ ID NO:10 |
| 5'-tcagcggagttggagctctcgg-3' | SEQ ID NO:11 |
| 5'-gtcgtaccacaggcattgtgatgg-3' | SEQ ID NO:12 |
| 5'-gcaatgcctgggtacatggtgg-3' | SEQ ID NO:13 |
| Primer Sequences Human | |
| 5'-atgggaagtctgcccagcagaag-3' | SEQ ID NO:14 |
| 5'-ctaggcatcatccaaagagacagcc-3' | SEQ ID NO:15 |
| 5'-aggagaggctcttactctctgtcag-3' | SEQ ID NO:16 |
| 5'-ctaggcatcatccaaagagacagcc-3' | SEQ ID NO:17 |

REFERENCES

1. Cantrell, D. (1996) T cell antigen receptor signal transduction pathways, *Annu. Rev. Immunol.* 14, 259-274.
2. Latour, S. & Veillette, A. (2001) Proximal protein tyrosine kinases in immunoreceptor signaling, *Curr Opin Immunol.* 13, 299-306.
3. van Leeuwen, J. E. & Samelson, L. E. (1999) T cell antigen-receptor signal transduction, *Curr Opin Immunol.* 11, 242-8.
4. Clements, J. L., Boerth, N. J., Lee, J. R. & Koretzky, G. A. (1999) Integration of T cell receptor-dependent signaling pathways by adapter proteins, *Annu Rev Immunol.* 17, 89-108.
5. Rudd, C. E. (1999) Adaptors and molecular scaffolds in immune cell signaling, *Cell.* 96, 5-8.
6. Zhang, W., Sloan-Lancaster, J., Kitchen, J., Trible, R. P. & Samelson, L. E. (1998) LAT: the ZAP-70 tyrosine kinase substrate that links T cell receptor to cellular activation, *Cell.* 92, 83-92.
7. Liu, S. K., Fang, N., Koretzky, G. A. & McGlade, C. J. (1999) The hematopoietic-specific adaptor protein gads 7. functions in T-cell signaling via interactions with the SLP-76 and LAT adaptors, *Curr. Biol.* 9, 67-75.
8. Weiss, A. & Littman, D. R. (1994) Signal transduction by lymphocyte antigen receptors, *Cell.* 76, 263-274.
9. Rudd, C. E. & Schneider. H. (2000) Lymphocyte signaling: Cbl sets the threshold for autoimmunity, *Curr Biol.* 10, R344-7.
10. Leo, A. & Schraven, B. (2001) Adapters in lymphocyte signaling, *Curr Opin Immunol.* 13, 307-16.
11. Brdicka, T., Pavlistova, D., Leo, A., Bruyns, E., Korinek, V., Angelisova, P., Scherer, J., Shevchenko, A., Hilgert, I., Cerny, J., Drbal, K., Kuramitsu, Y., Kornacker, B., Horejsi, V. & Schraven, B. (2000) Phosphoprotein associated with glycosphingolipid-enriched microdomains (PAG), a novel ubiquitously expressed transmembrane adaptor protein, binds the protein tyrosine kinase csk and is involved in regulation of T cell activation, *J Exp Med.* 191, 1591-604.
12. Pfrepper, K. I., Marie-Cardine, A., Simeoni, L., Kuramitsu, Y., Leo, A., Spicka, J., Hilgert, I., Scherer, J. & Schraven, B. (2001) Structural and functional dissection of the cytoplasmic domain of the transmembrane adaptor protein SIT (SHP2-interacting transmembrane adaptor protein), *Eur J Immunol.* 31, 1825-36.
13. Chow, L. M., Fournel, M., Davidson, D. & Veillette, A. (1993) Negative regulation of T-cell receptor signaling by tyrosine protein kinase p50csk, *Nature.* 365, 156-60.
14. Okada, M., Nada, S., Yamanashi, Y., Yamamoto, T. & Nakagawa, H. (1991) CSK: a protein-tyrosine kinase involved in regulation of src family kinases, *J Biol. Chem.* 266, 24249-52.
15. Lemay, S., Davidson, D., Latour, S. & Veillette, A. (2000) Dok-3, a novel adapter molecule involved in the negative regulation of immunoreceptor signaling, *Mol Cell Biol.* 20, 2743-54.
16. Thien, C. B. & Langdon, W. Y. (2001) Cbl: many adaptations to regulate protein tyrosine kinases, *Nat Rev Mol Cell Biol.* 2, 294-3 07.
17. Lupher, M. L., Jr., Rao, N., Eck, M. J. & Band, H. (1999) The Cbl protooncoprotein: a negative regulator of immune receptor signal transduction, *Immunol Today.* 20, 3 75-82.
18. Zheng, N., Wang, P., Jeffrey, P. D. & Pavietich, N. P. (2000) Structure of a c-Cbl-UbCH7 complex: RING domain function in ubiquitin-protein ligases, *Cell.* 102, 53 3-9.
19. Joazeiro, C. A., Wing, S. S., Huang, H., Leverson, J. D., Hunter, T. & Liu, Y. C. (1999) The tyrosine kinase negative regulator c-Cbl as a RiNG-type, E2-dependent ubiquitin-protein ligase, *Science.* 286, 309-312.
20. Donovan JA, Wange RL, Langdon WY & Samelson L E. (1994) The protein product of the c-cbl protooncogene is the 1 20-kDa tyrosine-phosphorylated protein in Jurkat cells activated via the T cell antigen receptor, *J. Biol. Chem.* 269, 2292 1-22924.
21. Fournel, M., Davidson, D., Weil, R. & Veillette, A. (1996) Association of tyrosine protein kinase Zap-70 with the protooncogene product pI2Oc-cbl in T lymphocytes., *I Exp. Med.* 183, 301-306.
22. Meng, W., Sawasdikosol, S., Burakoff, S. J. & Eck, M. J. (1999) Structure of the amino-terminal domain of Cbl complexed to its binding site on ZAP-70 kinase, *Nature.* 398, 84-90.
23. Lupher, M. L., Jr., Songyang, Z., Shoelson, S. E., Cantley, L. C. & Band, H. (1997) The Cbl phosphotyrosine-binding domain selects a D(N/D)XpY motif and binds to the Tyr292 negative regulatory phosphorylation site of ZAP-70, *J Biol. Chem.* 272, 33140-4.
24. Lupher, M. L., Jr., Rao, N., Lill, N. L., Andoniou, C. E., Miyake, S., Clark, E. A., Druker, B. & Band, H. (1998) Cbl-mediated negative regulation of the Syk tyrosine kinase. A critical role for Cbl phosphotyrosine-binding domain binding to Syk phosphotyrosine 323, *J Biol. Chem.* 273, 35273-81.
25. Murphy, M. A., Schnall, R. G., Venter, D. J., Bamett, L., Bertoncello, I., Thien, C. B., Langdon, W. Y. & Bowtell, D. D. (1998) Tissue hyperplasia and enhanced T-cell signaling via ZAP-70 in c-Cbl-deficient mice, *Mol. Cell. Biol.* 18, 4872-4882.
26. Rao, N., Lupher, M. L., Jr., Ota, S., Reedquist, K. A., Druker, B. J. & Band, H. (2000) The linker phosphorylation site Tyr292 mediates the negative regulatory effect of Cbl on ZAP-70 in T cells, *J Immunol.* 164, 4616-4626.
27. Ota, S., Hazeki, K., Rao, N., Lupher, M. L., Jr., Andoniou, C. E., Druker, B. & Band, H. (2000) The RING finger domain of Cbl is essential for negative regulation of the Syk tyrosine kinase, *J Biol. Chem.* 275, 414-22.
28. van Leeuwen, J. B., Paik, P. K. & Samelson, L. E. (1999) The oncogenic 70Z Cbl mutation blocks the phosphotyrosine binding domain-dependent negative regulation of ZAP-70 by c-Cbl in Jurkat T cells, *Mol Cell Biol.* 19, 6652-64.
29. Wang, H. Y., Altman, Y., Fang, D., Elly, C., Dai, Y., Shao, Y. & Liu, Y. C. (2001) Cbl Promotes Ubiquitination of the T Cell Receptor{zeta} through an Adaptor Function of Zap-70, *J Biol. Chem.* 15, 15.
30. Thien, C. B., Bowtell, D. D. & Langdon, W. Y. (1999) Perturbed regulation of ZAP-70 and sustained tyrosine phosphorylation of LAT and SLP-76 in c-Cbl-deficient thymocytes, *J. Immunol.* 162, 7133-9.
31. Levkowitz, G., Waterman, H., Zamir, E., Kam, Z., Oved, S., Langdon, W. Y., Beguinot, L., Geiger, 3. & Yarden, Y. (1998) c-Cbl/Sli-1 regulates endocytic sorting and ubiquitination of the epidermal growth factor receptor, *Genes Dev.* 12, 3663-3674.
32. Lee, P. 5., Wang, Y., Dominguez, M. G., Yeung, Y. G., Murphy, M. A., Bowtell, D. D. & Stanley, E. R. (1999) The Cbl protooncoprotein stimulates CSF-1 receptor multiubiquitination and endocytosis, and attenuates macrophage proliferation, *Embo* 1 18, 3616-3628.
33. Miyake, S., Muilane-Robinson, K. P., Liii, N. L., Douillard, P. & Band, H. (1999) Cbl mediated negative regulation of platelet-derived growth factor receptor-dependent cell proliferation. A critical role for Cbl tyrosine kinase-binding domain, *J Biol. Chem.* 274, 16619-28.
34. Sosinowski, T., Pandey, A., Dixit, V. M. & Weiss, A. (2000) Src-like adaptor protein (SLAP) is a negative regulator of T cell receptor signaling, *J Exp Med.* 191, 463474.
35. Roche 5, Alonso G, Kazlauskas A, Dixit Vm, Courtneidge Sa & Pandey A. (1998) Src-like adaptor protein (Slap) is a negative regulator of mitogenesis, *Curr Biol.* 8, 975-8.
36. Pandey A, Duan H & Dixit Vm. (1995) Characterization of a novel Src-like adapter protein that associates with the Eck receptor tyrosine kinase, *J Biol. Chem.* 270, 192014.
37. Sosinowski, T., Killeen, N. & Weiss, A. (2001) The Src-like adaptor protein downregulates the T cell receptor on CD4+CD8+ thymocytes and regulates positive selection, *Immunity.* 15, 457-66.
38. Liu, S. K. & McGlade, C. J. (1998) Gads is a novel SH2 and SH3 domain-containing adaptor protein that binds to tyrosine-phosphorylated Shc, *Oncogene.* 17, 3073-82.
39. Tang, J., Sawasdikosol, S., Chang, J. H. & Burakoff, S. J. (1999) SLAP, a dimeric adapter protein, plays a functional role in T cell receptor signaling, *Proc Natl Acad Sci USA.* 96, 9775-80.
40. Levkowitz, G., Waterman, H., Ettenberg, S. A., Katz, M., Tsygankov, A. Y., Alroy, I., Lavi, S., Iwai, K., Reiss, Y., Ciechanover, A., Lipkowitz, S. & Yarden, Y. (1999) Ubiquitin ligase activity and tyrosine phosphorylation underlie suppression of growth factor signaling by cCbl/Sli-1, *Mol Cell.* 4, 1029-40.
41. Manes G, Bello P & Roche 5. (2000) Slap negatively regulates Src mitogenic function but does not revert Src-induced cell morphology changes, *Mol Cell Biol.* 20, 3396-406.
42. Sinha, S., Jancarik, J., Roginskaya, V., Rothermund, K., Boxer, L. M. & Corey, S. J. (2001) Suppression of apoptosis and granulocyte colony-stimulating factor-induced differentiation by an oncogenic form of Cbl, *Exp Hematol.* 29, 746-5 5.
43. Waterman, H., Levkowitz, G., Alroy, I. & Yarden, Y. (1999) The RING finger of c-Cbl mediates desensitization of the epidermal growth factor receptor, *J Biol. Chem.* 274, 22151-4.
44. Hicke, L. (2001) A new ticket for entry into budding vesicles-ubiquitin, *Cell.* 106, 527-3 0.
45. Alcover, A. & Alarcon, B. (2000) Internalization and intracellular fate of TCR-CD3 complexes, *Crit Rev Immunol.* 20, 325-46.
46. Liu, H., Rhodes, M., Wiest, D. L. & Vignali, D. A. (2000) On the dynamics of TCR:CD3 complex cell surface expression and downmodulation, *Immunity.* 13, 665-75.
47. Lill, N. L., Douillard, P., Awwad, R. A., Ota, S., Lupher, M. L., Jr., Miyake, S., MeissnerLula, N., Hsu, V. W. & Band, H. (2000) The evolutionarily conserved N-terminal region of Cbl is sufficient to enhance down-regulation of the epidermal growth factor receptor, *J Biol. Chem.* 275, 367-77.
48. Yoon, C. H., Chang, C., Hopper, N. A., Lesa, G. M. & Sternberg, P. W. (2000) Requirements of multiple domains of SLI-1, a *Caenorhabditis elegans* homologue of c-Cbl, and an inhibitory tyrosine in LET-23 in regulating vulval differentiation, *Mol Biol Cell.* 1], 4019-31.
49. Berry, D. M., Benn, S. J., Cheng, A. M. & McGlade, C. J. (2001) Caspase-dependent cleavage of the hematopoietic specific adaptor protein Gads alters signaling from the T cell receptor, *Oncogene.* 20, 1203-11.
50. Kratchmarova, I., Sosinowski, T., Weiss, A., Witter, K., Vincenz, C. and Pandey, A. (2001). Characterization of promoter region and genomic structure of the murine and human genes encoding Src like adapter protein. *Gene,* 262, 267-273.
51. MacGrogan, D., Alvarez, S., DeBlasio, T., Jhanwar, S. C. and Nimer, S. D. (2001). Identification of candidate genes on chromosome band 20q12 by physical mapping of translocation breakpoints found in myeloid leukemia cell lines. *Oncogene,* 20, 4150-4160.
52. Miyake, S., Lupher, M. L., Druker, B. and Band, H. (1998) The tyrosine kinase regulator Cbl enhances the ubiquitination and degradation of the platelet-derived growth factor receptor alpha. *Proc. Natl. Acad. Science.* 95, 7927-7932.
53. Mount, S. M. (1982). A catalogue of splice junction sequences. *Nucleic Acids Res,* 10, 459-472.
54. Roulston, D., Espinosa, R., Stoffel, M., Bell, G. I. and Le Beau, M. M. (1993). Molecular genetics of myeloid leukemia: identification of the commonly deleted segment of chromosome 20. *Blood,* 82, 3424-3429.

The invention claimed is:

1. An isolated nucleic acid encoding a wild-type MARS protein, wherein the nucleic acid is selected from the group consisting of:
   (a) a nucleic acid sequence encoding a protein comprising the human MARS amino acid sequence of SEQ ID NO:5; and
   (b) a nucleic acid sequence encoding a protein comprising the mouse MARS amino acid sequence of SEQ ID NO:3.

2. An isolated nucleic acid encoding a mutant MARS protein having the nucleotide sequence of SEQ ID NO:7.

3. An isolated nucleic acid encoding a mutant MARS protein, said nucleic acid sequence having the nucleotide sequence of SEQ ID NO:6.

4. An isolated nucleic acid comprising the nucleotide sequence of SEQ ID NO: 1.

5. An isolated nucleic acid in comprising the nucleotide sequence of SEQ ID NO:2.

6. An isolated nucleic acid comprising the nucleotide sequence of SEQ ID NO:4.

7. An isolated nucleic acid comprising the nucleotide sequence of SEQ ID NO:6.

8. An isolated oligonucleotide consisting of a nucleic acid sequence, wherein the nucleic acid sequence is selected from the group consisting of SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17.

* * * * *

UNITED STATES PATENT AND TRADEMARK OFFICE
CERTIFICATE OF CORRECTION

PATENT NO. : 7,507,801 B2  Page 1 of 1
APPLICATION NO. : 10/432746
DATED : March 24, 2009
INVENTOR(S) : McGlade et al.

It is certified that error appears in the above-identified patent and that said Letters Patent is hereby corrected as shown below:

On Title Page:
Item 87, PCT Pub. Date: Please correct "Mar. 30, 2002"
to read -- May 30, 2002 --

Column 62, Claim 5, Line 25: After "nucleic acid" please delete "in"

Signed and Sealed this

Second Day of June, 2009

JOHN DOLL
*Acting Director of the United States Patent and Trademark Office*

SEQUENCE LISTING

<160> NUMBER OF SEQ ID NOS: 17

<210> SEQ ID NO 1
<211> LENGTH: 1348
<212> TYPE: DNA
<213> ORGANISM: Mus musculus

<400> SEQUENCE: 1

| | | | | | |
|---|---|---|---|---|---|
| ggcccaatct | ggtttctctg | agaagcaaag | gactgctgta | ctagtttcgt | ggagattgtc | 60 |
| tgctgacaaa | gaagcttgat | cacagtacct | cagcctactc | tgactccttt | ctggtgaccg | 120 |
| atcctccagg | ctgctgggc | ctgagatgcc | gactaccta | ggacctgcaa | aggcctgacc | 180 |
| tgtcgggtca | gtgtgcacat | tggctgacta | ccctcatcaa | acgtctgatg | gcaaacctt | 240 |
| cccttttccag | gttcagtgtg | cttgtgagcg | tctgctgagt | gatgggaagt | ttgtccagca | 300 |
| gagggaaaac | ctccagcccc | agcccagct | cctctggtcc | agaccaggaa | cccgtgtcca | 360 |
| tgcaaccaga | aagacacaag | gtcacagctg | tggccctggg | cagtttccca | gcaggtgaac | 420 |
| aggccagact | atctctgaga | ctcggggagc | cgctgaccat | catctctgag | gatggagatt | 480 |
| ggtggacagt | ccagtcggaa | gtctcaggca | gagagtacca | catgcccagt | gtgtatgtgg | 540 |
| ctaaagtcgc | ccacgggtgg | ctgtacgagg | gcctgagccg | ggagaaagcc | gaggaactac | 600 |

-continued

```
tcctgttacc tgggaaccccc ggaggggcct tcctcatccg ggagagccag accaggagag    660
gctgctattc cctgtccgtc cgactcagcc gccctgcatc ttgggaccgg atcagacact    720
acaggataca gcgtcttgac aatggctggc tgtacatctc acctcgcctc accttcccct    780
cactccacgc cttggtggag cattactctg agctagcaga tggcatctgc tgtcccctca    840
gggagccgtg tgtcctgcag aagcttgggc cactacctgg caaagataca cctccacctg    900
tgactgtgcc aacatcatca ctaaattgga aaaagctgga ccgcagcctc ctgtttctgg    960
aagcacctgc gagtggggag gcatctctgc tcagtgaggg gctccgagag tccctcagtt   1020
cctacatcag cctggctgag gacccctgg atgatgctta gccctggaac acaaagagaa    1080
agggaaccaa gactgtggca ccgagagctc caactccgct gaccctgaca agctccagg    1140
aggcaaggct gggagaacag agacggctgg ggtggggcac agacactcgg ggcctcacct   1200
gggctttctg ataagtcatg tatctcctaa ggcctcaccc ctacctacta cttctagtcc   1260
atgtgcagtg cagttcaaag cagggctggc ctctacagag aataaaatac ttctgaggtc   1320
caaaaaaaaa aaaaaaaaaa aaaaaaaa                                     1348
```

<210> SEQ ID NO 2
<211> LENGTH: 777
<212> TYPE: DNA
<213> ORGANISM: Mus musculus

<400> SEQUENCE: 2

```
atgggaagtt tgtccagcag agggaaaacc tccagcccca gccccagctc ctctggtcca     60
gaccaggaac ccgtgtccat gcaaccagaa agacacaagg tcacagctgt ggccctgggc    120
agtttcccag caggtgaaca ggccagacta tctctgagac tcggggagcc gctgaccatc    180
atctctgagg atggagattg gtggacagtc cagtcggaag tctcaggcag agagtaccac    240
atgcccagtg tgtatgtggc taaagtcgcc cacgggtggc tgtacgaggg cctgagccgg    300
gagaaagccg aggaactact cctgttacct gggaaccccg gagggccttt cctcatccgg    360
gagagccaga ccaggagagg ctgctattcc ctgtccgtcc gactcagccg ccctgcatct    420
tgggaccgga tcagacacta caggatacag cgtcttgaca atggctggct gtacatctca    480
cctcgcctca ccttcccctc actccacgcc ttggtggagc attactctga gctagcagat    540
ggcatctgct gtcccctcag ggagccgtgt gtcctgcaga agcttgggcc actacctggc    600
aaagatacac ctccacctgt gactgtgcca acatcatcac taaattgaa aaagctggac    660
cgcagcctcc tgtttctgga agcacctgcg agtggggagg catctctgct cagtgagggg    720
ctccgagagt ccctcagttc ctacatcagc ctggctgagg accccttgga tgatgct      777
```

<210> SEQ ID NO 3
<211> LENGTH: 259
<212> TYPE: PRT
<213> ORGANISM: Mus musculus

<400> SEQUENCE: 3

```
Met Gly Ser Leu Ser Ser Arg Gly Lys Thr Ser Ser Pro Ser Pro Ser
 1               5                  10                  15

Ser Ser Gly Pro Asp Gln Glu Pro Val Ser Met Gln Pro Glu Arg His
            20                  25                  30

Lys Val Thr Ala Val Ala Leu Gly Ser Phe Pro Ala Gly Glu Gln Ala
        35                  40                  45

Arg Leu Ser Leu Arg Leu Gly Glu Pro Leu Thr Ile Ile Ser Glu Asp
    50                  55                  60
```

Gly Asp Trp Trp Thr Val Gln Ser Glu Val Ser Gly Arg Glu Tyr His
65                  70                  75                  80

Met Pro Ser Val Tyr Val Ala Lys Val Ala His Gly Trp Leu Tyr Glu
                85                  90                  95

Gly Leu Ser Arg Glu Lys Ala Glu Glu Leu Leu Leu Leu Pro Gly Asn
            100                 105                 110

Pro Gly Gly Ala Phe Leu Ile Arg Glu Ser Gln Thr Arg Arg Gly Cys
        115                 120                 125

Tyr Ser Leu Ser Val Arg Leu Ser Arg Pro Ala Ser Trp Asp Arg Ile
    130                 135                 140

Arg His Tyr Arg Ile Gln Arg Leu Asp Asn Gly Trp Leu Tyr Ile Ser
145                 150                 155                 160

Pro Arg Leu Thr Phe Pro Ser Leu His Ala Leu Val Glu His Tyr Ser
                165                 170                 175

Glu Leu Ala Asp Gly Ile Cys Cys Pro Leu Arg Glu Pro Cys Val Leu
            180                 185                 190

Gln Lys Leu Gly Pro Leu Pro Gly Lys Asp Thr Pro Pro Val Thr
    195                 200                 205

Val Pro Thr Ser Ser Leu Asn Trp Lys Lys Leu Asp Arg Ser Leu Leu
210                 215                 220

Phe Leu Glu Ala Pro Ala Ser Gly Glu Ala Ser Leu Leu Ser Glu Gly
225                 230                 235                 240

Leu Arg Glu Ser Leu Ser Ser Tyr Ile Ser Leu Ala Glu Asp Pro Leu
            245                 250                 255

Asp Asp Ala

<210> SEQ ID NO 4
<211> LENGTH: 786
<212> TYPE: DNA
<213> ORGANISM: Homo sapiens

<400> SEQUENCE: 4
atgggaagtc tgcccagcag aagaaaatct ctgccaagcc caagcttgag ttcctctgtc     60
caaggccagg gacctgtgac catggaagca gagagaagca aggccacagc cgtggccctg    120
ggcagtttcc cggcagtgg cccggccgag ctgtcgctga ctcggggga gccattgacc     180
atcgtctctg aggatggaga ctggtggacg gtgctgtctg aagtctcagg cagagagtat    240
aacatcccca gcgtccacgt ggccaaagtc tcccatgggt ggctgtatga gggcctgagc    300
agggagaaag cagaggaact gctgttgtta cctgggaacc ctggaggggc cttcctcatc    360
cgggagagcc agaccaggag aggctcttac tctctgtcag tccgcctcag ccgccctgca    420
tcctgggacc ggatcagaca ctacaggatc cactgccttg acaatggctg gctgtacatc    480
tcaccgcgcc tcaccttccc ctcactccag gccctggtgg accattactc tgagctggcg    540
gatgacatct gctgcctact caaggagccc tgtgtcctgc agagggctgg cccgctccct    600
ggcaaggata taccctacc tgtgactgtg cagaggacac cactcaactg gaaagagctg    660
gacagctccc tcctgttttc tgaagctgcc acaggggagg agtctcttct cagtgagggt    720
ctccgggagt ccctcagctt ctacatcagc ctgaatgacg aggctgtctc tttggatgat    780
gcctag                                                               786

<210> SEQ ID NO 5
<211> LENGTH: 261
<212> TYPE: PRT

<213> ORGANISM: Homo sapiens

<400> SEQUENCE: 5

```
Met Gly Ser Leu Pro Ser Arg Arg Lys Ser Leu Pro Ser Pro Ser Leu
1               5                   10                  15
Ser Ser Ser Val Gln Gly Gln Gly Pro Val Thr Met Glu Ala Glu Arg
            20                  25                  30
Ser Lys Ala Thr Ala Val Ala Leu Gly Ser Phe Pro Ala Gly Gly Pro
        35                  40                  45
Ala Glu Leu Ser Leu Arg Leu Gly Glu Pro Leu Thr Ile Val Ser Glu
    50                  55                  60
Asp Gly Asp Trp Trp Thr Val Leu Ser Glu Val Ser Gly Arg Glu Tyr
65                  70                  75                  80
Asn Ile Pro Ser Val His Val Ala Lys Val Ser His Gly Trp Leu Tyr
                85                  90                  95
Glu Gly Leu Ser Arg Glu Lys Ala Glu Glu Leu Leu Leu Leu Pro Gly
            100                 105                 110
Asn Pro Gly Gly Ala Phe Leu Ile Arg Glu Ser Gln Thr Arg Arg Gly
        115                 120                 125
Ser Tyr Ser Leu Ser Val Arg Leu Ser Arg Pro Ala Ser Trp Asp Arg
130                 135                 140
Ile Arg His Tyr Arg Ile His Cys Leu Asp Asn Gly Trp Leu Tyr Ile
145                 150                 155                 160
Ser Pro Arg Leu Thr Phe Pro Ser Leu Gln Ala Leu Val Asp His Tyr
                165                 170                 175
Ser Glu Leu Ala Asp Asp Ile Cys Cys Leu Leu Lys Glu Pro Cys Val
            180                 185                 190
Leu Gln Arg Ala Gly Pro Leu Pro Gly Lys Asp Ile Pro Leu Pro Val
        195                 200                 205
Thr Val Gln Arg Thr Pro Leu Asn Trp Lys Glu Leu Asp Ser Ser Leu
210                 215                 220
Leu Phe Ser Glu Ala Ala Thr Gly Glu Glu Ser Leu Leu Ser Glu Gly
225                 230                 235                 240
Leu Arg Glu Ser Leu Ser Phe Tyr Ile Ser Leu Asn Asp Glu Ala Val
                245                 250                 255
Ser Leu Asp Asp Ala
            260
```

<210> SEQ ID NO 6
<211> LENGTH: 737
<212> TYPE: DNA
<213> ORGANISM: Homo sapiens

<400> SEQUENCE: 6

```
atgggaagtc tgcccagcag aagaaaatct ctgccaagcc caagcttgag ttcctctgtc    60
caaggccagg gacctgtgac catggaagca gagagaagca aggccacagc cgtggccctg   120
ggcagtttcc cggcaggtgg cccggccgag ctgtcgctga actcggggga gccattgacc   180
atcgtctctg aggatggaga ctggtggacg gtgctgtctg aagtctcagg cagagagtat   240
aacatcccca gcgtccacgt ggccaaagtc tcccatgggt ggctgtatga gggcctgagc   300
agggagaaag cagaggaact gctgttgtta cctgggaacc ctggaggggc cttcctcatc   360
cgggagagcc agaccaggag aggctcttac tctctgtcag tccgcctcag ccgccctgca   420
tcctgggacc ggatcagaca ctacaggatc cactgccttg acaatggctg gctgtacatc   480
```

```
tcaccgcgcc tcaccttccc ctcactccag gccctggtgg accattactc tgagggctgg      540
cccgctccct ggcaaggata taccgctacc tgtgactgtg cggaggacac cactcaactg      600
gaaagagctg acagctccc  tcctgttttc tgaagctgcc acaggggagg agtctcttct      660
cagtgagggt ctccgggagt ccctcagctt ctacatcagc ctgaatgagc gaggctgtct      720
ctttggatga tgcctag                                                    737
```

```
<210> SEQ ID NO 7
<211> LENGTH: 210
<212> TYPE: PRT
<213> ORGANISM: Homo sapiens

<400> SEQUENCE: 7

Met Gly Ser Leu Pro Ser Arg Arg Lys Ser Leu Pro Ser Pro Ser Leu
1               5                   10                  15

Ser Ser Ser Val Gln Gly Gln Gly Pro Val Thr Met Glu Ala Glu Arg
            20                  25                  30

Ser Lys Ala Thr Ala Val Ala Leu Gly Ser Phe Pro Ala Gly Gly Pro
        35                  40                  45

Ala Glu Leu Ser Leu Arg Leu Gly Glu Pro Leu Thr Ile Val Ser Glu
    50                  55                  60

Asp Gly Asp Trp Trp Thr Val Leu Ser Glu Val Ser Gly Arg Glu Tyr
65                  70                  75                  80

Asn Ile Pro Ser Val His Val Ala Lys Val Ser His Gly Trp Leu Tyr
                85                  90                  95

Glu Gly Leu Ser Arg Glu Lys Ala Glu Leu Leu Leu Leu Pro Gly
            100                 105                 110

Asn Pro Gly Gly Ala Phe Leu Ile Arg Glu Ser Gln Thr Arg Arg Gly
        115                 120                 125

Ser Tyr Ser Leu Ser Val Arg Leu Ser Arg Pro Ala Ser Trp Asp Arg
    130                 135                 140

Ile Arg His Tyr Arg Ile His Cys Leu Asp Asn Gly Trp Leu Tyr Ile
145                 150                 155                 160

Ser Pro Arg Leu Thr Phe Pro Ser Leu Gln Ala Leu Val Asp His Tyr
                165                 170                 175

Ser Glu Gly Trp Pro Ala Pro Trp Gln Gly Tyr Thr Pro Thr Cys Asp
            180                 185                 190

Cys Ala Glu Asp Thr Thr Gln Leu Glu Arg Ala Gly Gln Leu Pro Pro
        195                 200                 205

Val Phe
    210

<210> SEQ ID NO 8
<211> LENGTH: 25
<212> TYPE: DNA
<213> ORGANISM: Artificial sequence
<220> FEATURE:
<223> OTHER INFORMATION: Oligonucleotide primer

<400> SEQUENCE: 8
cacgctcttt gtccctgctg tgctg                                            25

<210> SEQ ID NO 9
<211> LENGTH: 26
<212> TYPE: DNA
<213> ORGANISM: Artificial sequence
<220> FEATURE:
<223> OTHER INFORMATION: Oligonucleotide primer
```

<400> SEQUENCE: 9
ggcccaatct ggtttctctg agaagc                                  26

<210> SEQ ID NO 10
<211> LENGTH: 23
<212> TYPE: DNA
<213> ORGANISM: Artificial sequence
<220> FEATURE:
<223> OTHER INFORMATION: Oligonucleotide primer

<400> SEQUENCE: 10
tgtacatctc acctcgcctc acc                                     23

<210> SEQ ID NO 11
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 11
tcagcggagt tggagctctc gg                                      22

<210> SEQ ID NO 12
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 12
gtcgtaccac aggcattgtg atgg                                    24

<210> SEQ ID NO 13
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 13
gcaatgcctg ggtacatggt gg                                      22

<210> SEQ ID NO 14
<211> LENGTH: 23
<212> TYPE: DNA
<213> ORGANISM: Artificial sequence
<220> FEATURE:
<223> OTHER INFORMATION: Oligonucleotide primer

<400> SEQUENCE: 14
atgggaagtc tgcccagcag aag                                     23

<210> SEQ ID NO 15
<211> LENGTH: 25
<212> TYPE: DNA
<213> ORGANISM: Artificial sequence
<220> FEATURE:
<223> OTHER INFORMATION: Oligonucleotide primer

<400> SEQUENCE: 15
ctaggcatca tccaaagaga cagcc                                   25

<210> SEQ ID NO 16

```
<211> LENGTH: 25
<212> TYPE: DNA
<213> ORGANISM: Artificial sequence
<220> FEATURE:
<223> OTHER INFORMATION: Oligonucleotide primer

<400> SEQUENCE: 16
aggagaggct cttactctct gtcag                                25

<210> SEQ ID NO 17
<211> LENGTH: 25
<212> TYPE: DNA
<213> ORGANISM: Artificial sequence
<220> FEATURE:
<223> OTHER INFORMATION: Oligonucleotide primer

<400> SEQUENCE: 17
ctaggcatca tccaaagaga cagcc                                25
```